(12) United States Patent
Engelhardt et al.

(10) Patent No.: US 8,207,179 B2
(45) Date of Patent: Jun. 26, 2012

(54) SUBSTITUTED INDOLINES AS TYROSINE KINASE INHIBITORS

(75) Inventors: Harald Engelhardt, Ebreichsdorf (AT); Bodo Betzemeier, Biberach (DE); Guido Boehmelt, Gaaden (AT); Ulrich Guertler, Vienna (AT); Thomas Karner, Vienna (AT); Oliver Kraemer, Vienna (AT); Daniel Kuhn, Vienna (AT); Jens Juergen Quant, Perchtoldsdorf (AT); Ulrich Reiser, Vienna (AT); Otmar Schaaf, Vienna (AT); Flavio Solca, Vienna (AT); Heinz Stadtmueller, Vienna (AT); Ulrike Tontsch-Grunt, Baden (AT); Matthias Treu, Vienna (AT); Stephan Karl Zahn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 20 days.

(21) Appl. No.: 12/664,162

(22) PCT Filed: Jun. 9, 2008

(86) PCT No.: PCT/EP2008/057150
§ 371 (c)(1),
(2), (4) Date: Mar. 18, 2010

(87) PCT Pub. No.: WO2008/152014
PCT Pub. Date: Dec. 18, 2008

(65) Prior Publication Data
US 2010/0222331 A1    Sep. 2, 2010

(30) Foreign Application Priority Data
Jun. 12, 2007 (EP) .................................. 07110049

(51) Int. Cl.
*A61K 31/517* (2006.01)
(52) U.S. Cl. ..................... 514/266.2; 544/284
(58) Field of Classification Search .................. 544/284
See application file for complete search history.

(56) References Cited

FOREIGN PATENT DOCUMENTS
WO    02074742 A2    9/2002
WO    03084951 A1    10/2003

OTHER PUBLICATIONS

Bolotov et al.; Condensation of Ethyl-2-Oxoindoline-3-Glyoxylate With o-Aminophenol and o-Phenylenediamine; Chemistry of Heterocyclic Compounds; vol. 40; No. 2; 2004; pp. 211-213.
Dandia et al.; Synthesis of Novel 3-Spiro Indolines Containing Benz(g) Indazole, Benz(h)Pyrazolo(3,4-b)Quinoline and Naphthisoxazol Moieties; Heterocyclic Communications; vol. 2; No. 3; 1996; pp. 281-286.
Lackey et al.; Synthesis of Substituted Quinoline-4-carboxylic Acids; Synthesis; vol. 10; 1993; pp. 993-997.
International Search Report, Form PCT/ISA/210, for corresponding PCT/EP2008/057150; date of mailing: Mar. 10, 2009.

*Primary Examiner* — James O Wilson
*Assistant Examiner* — Brian McDowell
(74) *Attorney, Agent, or Firm* — Michael P. Morris; Mary-Ellen M. Devlin

(57) ABSTRACT

The present invention encompasses compounds of general Formula (1) wherein $R^2$, $R^3$, Q, W, X, Y and Z are defined as in claim 1, which are suitable for the treatment of diseases characterized by excessive or abnormal cell proliferation, and the use thereof for preparing a medicament having the above-mentioned properties.

(1)

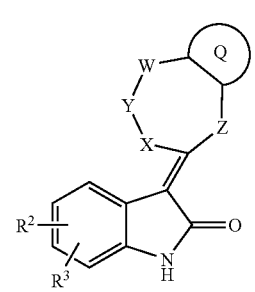

4 Claims, No Drawings

SUBSTITUTED INDOLINES AS TYROSINE KINASE INHIBITORS

The present invention relates to new indolinones of general formula (1)

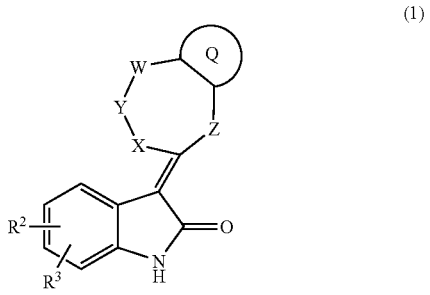

(1)

wherein the groups $R^2$, $R^3$, Q, W, X, Y and Z have the meanings given in the claims and specification, the isomers thereof, processes for preparing these indolinones and their use as medicaments.

The aim of the present invention is to discover new active substances which can be used for the prevention and/or treatment of diseases characterised by excessive or abnormal cell proliferation.

BACKGROUND TO THE INVENTION

Indolinones are described for example as receptor tyrosinekinases and cyclin/CDK-complex inhibiting compounds (WO02/081445, WO01/27081 or WO 2004/026829).

DETAILED DESCRIPTION OF THE INVENTION

It has now been found that, surprisingly, compounds of general formula (1), wherein the groups $R^2$, $R^3$, Q, W, X, Y and Z have the meanings given hereinafter act as inhibitors of specific cell cycle kinases. Moreover, certain forms also inhibit kinases that play an important part in intracellular signal transduction pathways. Thus, the compounds according to the invention may be used for example for the treatment of diseases connected with the activity of specific cell cycle kinases and characterised by excessive or abnormal cell proliferation. They may also be used to treat diseases characterised by abnormal activation of the corresponding signal transduction pathways.

The present invention relates to compounds of general formula (1)

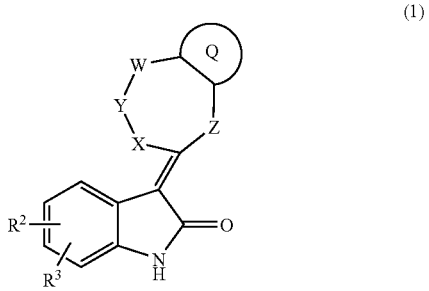

(1)

wherein

Q denotes $C_{6-10}$aryl or 5-12 membered heteroaryl, optionally substituted by one or more identical or different $R^1$, and W denotes a bond, —O—, —$NR^6$—, —$CR^6R^6$, and X denotes —O—, —S, —S(O), —S($O_2$), —$NR^4$—, —$CR^4R^4$— or —C(O)—; and Y denotes —O—, —$NR^5$—, —$CR^5R^5$— or —C(O)—; while optionally an $R^4$ may form, with an $R^5$, a 4-7 membered ring, optionally substituted by one or more $R^8$; or the substituents $R^4$ and $R^4$, $R^5$ and $R^5$ or $R^6$ and $R^6$ bound to the carbon atom may together form a 4-7-membered ring, which may optionally contain one or more heteroatoms selected from among N, O and S; and Z denotes —O—, —$NR^7$— or —$CR^7R^7$, or Y denotes a bond, X denotes —$NR^4$— and Z denotes —$NR^7$—, and at least one substituent selected from among X, Y and Z denotes a heteroatom; and $R^1, R^2, R^3, R^4, R^5, R^6, R^7$ und $R^8$ each independently of one another denote a group selected from among $R^a$, $R^b$ and $R^a$ substituted by one or more identical or different $R^b$ and/or $R^c$, wherein $R^2$ and/or $R^3$ is not hydrogen; and each $R^a$ independently of one another denotes hydrogen or is selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl; each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =NN($R^g$)C(O)$NR^cR^c$, —$NR^cR^c$, —$ONR^cR^c$, —N($OR^c$)$R^c$, —N($R^g$)$NR^cR^c$, halogen, —$CF_3$, —CN, —NC, —OCN, —SCN, —NO, —$NO_2$, =$N_2$, —$N_3$, —S(O)$R^c$, —S(O)$OR^c$, —S(O)$_2R^c$, —S(O)$_2OR^c$, —S(O)$NR^cR^c$, —S(O)$_2NR^cR^c$, —OS(O)$R^c$, —OS(O)$_2R^c$, —OS(O)$_2OR^c$, —OS(O)$NR^cR^c$, —OS(O)$_2NR^cR^c$, —C(O)$R^c$, —C(O)$OR^c$, —C(O)$SR^c$, —C(O)$NR^cR^c$, —C(O)N($R^g$)$NR^cR^c$, —C(O)N($R^g$)$OR^c$, —C($NR^g$)$NR^cR^c$, —C(NOH)$R^c$, —C(NOH)$NR^cR^c$, —OC(O)$R^c$, —OC(O)$OR^c$, —OC(O)$SR^c$, —OC(O)$NR^cR^c$, —OC($NR^g$)$NR^cR^c$, —SC(O)$R^c$, —SC(O)$OR^c$, —SC(O)$NR^cR^c$, —SC($NR^g$)$NR^cR^c$, —N($R^g$)C(O)$R^c$, —N[C(O)$R^c$]$_2$, —N($OR^g$)C(O)$R^c$, —N($R^g$)C($NR^g$)$R^c$, —N($R^g$)N($R^g$)C(O)$R^c$, —N[C(O)$R^c$]$NR^cR^c$, —N($R^g$)C(S)$R^c$, —N($R^g$)S(O)$R^c$, —N($R^g$)S(O)$OR^c$, —N($R^g$)S(O)$_2R^c$, N[S(O)$_2R^c$]$_2$, —N($R^g$)S(O)$_2OR^c$, —N($R^g$)S(O)$_2NR^cR^c$, —N($R^g$)[S(O)$_2$]$_2R^c$, N($R^g$)C(O)$OR^c$, —N($R^g$)C(O)$SR^c$, —N($R^g$)C(O)$NR^cR^c$, —N($R^g$)C(O)$NR^gNR^cR^c$, N($R^g$)N($R^g$)C(O)$NR^cR^c$, —N($R^g$)C(S)$NR^cR^c$, —[N($R^g$)C(O)]$_2R^c$, —N($R^g$)[C(O)]$_2R^c$, N{[C(O)]$_2R^c$}$_2$, —N($R^g$)[C(O)]$_2OR^c$, —N($R^g$)[C(O)]$_2NR^cR^c$, —N{[C(O)]$_2OR^c$}$_2$, —N{[C(O)]$_2$ $NR^cR^c$}$_2$, —[N($R^g$)C(O)]$_2$ $OR^c$, —N($R^g$)C($NR^g$)$OR^c$, —N($R^g$)C(NOH)$R^c$, N($R^g$)C($NR^g$)$SR^c$ and —N($R^g$)C($NR^g$)$NR^cR^c$, each $R^c$ independently of one another denotes hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =NN($R^g$)C(O)$NR^eR^e$, —$NR^eR^e$, —$ONR^eR^e$, —N($R^g$)$NR^eR^e$, halogen, —$CF_3$, —CN, —NC, —OCN, —SCN, —NO, —$NO_2$, =$N_2$, —$N_3$, —S(O)$R^e$, —S(O)$OR^e$, —S(O)$_2R^e$, —S(O)$_2OR^e$, —S(O)$NR^eR^e$, —OS(O)$R^e$, —OS(O)$_2R^e$, —OS(O)$_2OR^e$, —OS(O)$NR^eR^e$, —OS(O)$_2$ $NR^eR^e$, —C(O)$R^e$, —C(O)$OR^e$, —C(O)$SR^e$, —C(O)$NR^eR^e$, —C(O)N($R^g$)$NR^eR^e$, —C(O)N($R^g$)$OR^e$, —C($NR^g$)$NR^e$ R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, N(R$^g$)S(O)$_2$OR$^e$, N(R$^g$)S(O)$_2$NR$^e$R$^e$, N(R$^g$)[S(O)$_2$]$_2$R$^e$, —N(R$^g$)C(O)OR$^e$, —N(R$^g$)C(O)SR$^e$, N(R$^g$)C(O)NR$^e$R$^e$, N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, N(R$^g$)C(NOH)R$^e$, —N(R$^g$)C(NR$^g$)SR$^e$ and —N(R$^g$)C(NR$^g$)NR$^e$R$^e$, each R$^e$ independently of one another denotes hydrogen or a group optionally substituted by one or more identical or different R$^f$ and/or R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^f$ is a suitable group and each is independently selected from among halogen and —CF$_3$; and each R$^g$ independently of one another denotes hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, optionally in the form of the prodrugs, the tautomers, the racemates, the enantiomers, the diastereomers and the mixtures thereof, and optionally the pharmacologically acceptable acid addition salts thereof.

In one aspect the invention relates to compounds of general formula (1), wherein Z denotes —NR$^7$—.

In another aspect the invention relates to compounds of general formula (1), wherein R$^7$ denotes hydrogen or C$_{1-6}$alkyl.

In another aspect the invention relates to compounds of general formula (1), wherein Q denotes phenyl.

In another aspect the invention relates to compounds of general formula (1), wherein X denotes —NR$^4$—.

In another aspect the invention relates to compounds of general formula (1), wherein R$^4$ denotes hydrogen.

In another aspect the invention relates to compounds of general formula (1), wherein Y denotes —CR$^5$R$^5$—.

In another aspect the invention relates to compounds of general formula (1), wherein R$^5$ in each case denotes hydrogen.

In another aspect the invention relates to compounds of general formula (1) as pharmaceutical compositions.

In another aspect the invention relates to compounds of general formula (1) for preparing a pharmaceutical composition with an antiproliferative or signal transduction inhibiting activity.

In another aspect the invention relates to a pharmaceutical preparation, containing as active substance one or more compounds of general formula (1) or the physiologically acceptable salts thereof, optionally in combination with conventional excipients and/or carriers.

In another aspect the invention relates to the use of compounds of general formula (1) for preparing a pharmaceutical composition for the treatment and/or prevention of cancer, infections, inflammations and autoimmune diseases.

In another aspect the invention relates to a pharmaceutical preparation comprising a compound of general formula (1) and at least one further cytostatic or cytotoxic active substance, different from formula (1), optionally in the form of the prodrugs, the tautomers, the racemates, the enantiomers, the diastereomers and the mixtures thereof, and optionally the pharmacologically acceptable acid addition salts thereof.

DEFINITIONS

As used herein, the following definitions apply, unless stated otherwise.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.

Straight-Chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1,1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

By the term heteroalkyl are meant groups which are derived from the alkyl as hereinbefore defined in its widest sense by replacing, in the hydrocarbon chains, one or more of the groups —CH$_3$ independently of one another by the groups —OH, —SH or —NH$_2$, one or more of the groups —CH$_2$— independently of one another by the groups —O—, —S— or —NH—, one or more of the groups

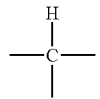

by the group

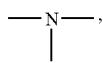

one or more of the groups =CH— by the group =N—, one or more of the groups =CH$_2$ by the group =NH or one or more of the groups ≡CH by the group ≡N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylamino ethyl (1-dimethylamino ethyl; 2-dimethyl-aminoethyl); dimethylaminopropyl (1-dimethylaminopropyl, 2-dimethylaminopropyl, 3-dimethylaminopropyl); diethylamino methyl; diethylamino ethyl (1-diethylamino ethyl, 2-diethylamino ethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethylamino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

Halogen encompasses fluorine, chlorine, bromine and/or iodine atoms.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms. Typical examples include, for example:

—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; and —CHFCH$_2$CF$_3$.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system. The following individual sub-groups are listed by way of example:

Monocyclic Saturated Hydrocarbon Rings:
cyclopropyl; cyclobutyl; cyclopentyl; cyclohexyl; cycloheptyl etc.

Monocyclic Unsaturated Hydrocarbon Rings:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Saturated and Unsaturated Bicyclic Hydrocarbon Rings:
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.

Saturated and Unsaturated Spirohydrocarbon Rings:
spiro[2.5]octyl, spiro[3.3]heptyl, spiro[4.5]dec-2-ene, etc.

Cycloalkylalkyl denotes the combination of the alkyl and cycloalkyl groups defined hereinbefore, in each case in their broadest sense. The alkyl group as substituent is directly linked to the molecule and is in turn substituted by a cycloalkyl group. The linking of alkyl and cycloalkyl in both groups may be effected by means of any suitable carbon atoms. The sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system. Typical examples include phenyl, naphthyl, indanyl (2,3-dihydroindenyl), 1,2,3,4-tetrahydronaphthyl and fluorenyl.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples include benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.
Monocyclic Heteroaryls:
furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.
Polycyclic Heteroaryls:
indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.
Monocyclic Heterorings (Saturated and Unsaturated):
tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-5-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.
Bicyclic Heterorings (Saturated and Unsaturated):
8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2] nonyl; hexahydro-furo[3,2-b]furyl; etc.
Spiro-Heterorings (Saturated and Unsaturated):
1,4-dioxa-spiro[4.5]decyl; 1-oxa-3,8-diaza-spiro[4.5]decyl; and 2,6-diaza-spiro[3.3]heptyl; 2,7-diaza-spiro[4.4] nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "suitable substituent" is meant a substituent which on the one hand is suitable by virtue of its valency and on the other hand leads to a system which is chemically stable.

By "prodrug" is meant an active substance in the form of its precursor metabolite. A distinction may be made between partly multi-part carrier-prodrug systems and biotransformation systems. The latter contain the active substance in a form that requires chemical or biological metabolisation. The skilled man will be familiar with prodrug systems of this kind (Sloan, Kenneth B.; Wasdo, Scott C. The role of prodrugs in penetration enhancement. Percutaneous Penetration Enhancers (2nd Edition) (2006). 51-64; Lloyd, Andrew W. Prodrugs. Smith and Williams' Introduction to the Principles of Drug Design and Action (4th Edition) (2006), 211-232; Neervannan, Seshadri. Strategies to impact solubility and dissolution rate during drug lead optimization: salt selection and prodrug design approaches. American Pharmaceutical Review (2004), 7(5), 108.110-113). A suitable prodrug contains for example a substance of the general formulae which is linked via an enzymatically cleavable linker (e.g. carbamate, phosphate, N-glycoside or a disulphide group to a dissolution-improving substance (e.g. tetraethyleneglycol, saccharide, amino acids). Carrier-prodrug systems contain the active substance as such, bound to a masking group which can be cleaved by the simplest possible controllable mechanism. The function of masking groups according to the invention in the compounds according to the invention is to neutralise the charge for improving cell uptake. If the compounds according to the invention are used with a masking group, these may also additionally influence other pharmacological parameters, such as for example oral bioavailability, tissue distribution, pharmacokinetics and stability against non-specific phosphatases. The delayed release of the active substance may also involve a sustained-release effect. In addition, modified metabolisation may occur, thus resulting in a higher efficiency of the active substance or organic specificity. In the case of a prodrug formulation, the masking group or a linker that binds the masking group to the active substance is selected such that the prodrug is sufficiently hydrophilic to be dissolved in the blood serum, has sufficient chemical and enzymatic stability to reach the activity site and is also sufficiently hydrophilic to ensure that it is suitable for diffusion-controlled membrane transport. Furthermore, it should allow chemically or ensymatically induced release of the active substance within a reasonable period and, it goes without saying, the auxiliary components released should be non-toxic. Within the scope of the invention, however, the compound without a mask or linker, and a mask, may be regarded as a prodrug which first of all has to be prepared in the cell from the ingested compound by enzymatic and biochemical processes.

Preparation of 6-nitroindolinone

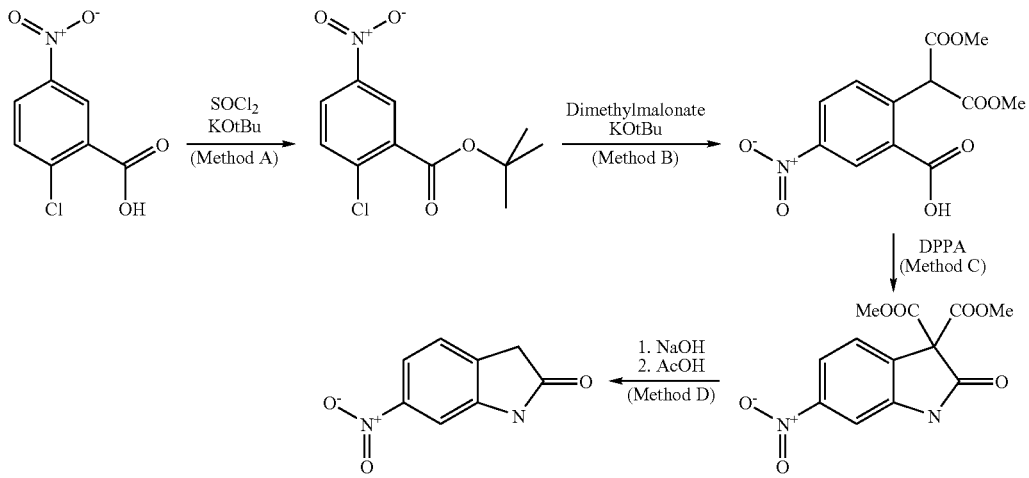

Method A—tert. Butyl 2-chloro-4-nitrobenzenecarboxylate (A1)

2-Chloro-5-nitrobenzoic acid (22 g, 109.1 mmol) and DMF (500 μL) are refluxed in toluene (50 mL)/thionyl chloride (8.5 mL) for 1.5 h with stirring. The reaction mixture is evaporated down and the residue is taken up in anhydrous THF (200 mL). Potassium-tert.-butoxide (12.5 g, 111.4 mmol) is added at 0° C., then the cooling is removed and the mixture is stirred for 30 min. The solvent is distilled off and the residue is divided between water and EtOAc. The organic phase is washed with water and 0.1 N NaOH, dried, filtered and evaporated down. Yield: 24 g (85%)

Method B—Dimethyl 2-(2-carboxy-4-nitrophenyl)malonate (A2)

Potassium-tert.-butoxide (50.0 g, 446 mmol) is dissolved at 20° C. in anhydrous DMSO (300 mL), at this temperature dimethyl malonate (67.0 mL, 586 mmol) is added and the mixture is stirred for 20 min. A1 (45.7 g, 177 mmol) is added and the mixture is stirred for 30 min at 100° C. It is poured from water (800 mL), acidified with concentrated HCl (30 mL) and extracted exhaustively with $CH_2Cl_2$. The organic phase is washed with water, dried, filtered and evaporated down. The residue is stirred in formic acid (300 mL) for 1.5 h at 72° C. The mixture is evaporated down, the residue is taken up in EtOAc, washed with NaCl solution and exhaustively extracted with dilute $NaHCO_3$ solution. The combined aqueous phase is acidified with concentrated HCl and exhaustively extracted with $CH_2Cl_2$. The combined organic phase is washed with water, dried, filtered and evaporated down. Yield: 38.4 g (73%)

Method C—Dimethyl 6-nitro-2-oxo-1,2-dihydroindol-3,3-dicarboxylate (A3)

Triethylamine (9.4 mL, 67.8 mmol) is added to A2 (20 g, 67.3 mmol) and DPPA (14.5 mL, 67.4 mmol) in anhydrous THF (40 mL) and the mixture is stirred for 1.25 h at boiling temperature. The reaction mixture is evaporated down, the residue is taken up in CH₂Cl₂ and washed with 1 N HCl. The organic phase is combined with ether and the precipitate is filtered off. Yield: 9.89 g (50%)

Method D—6-Nitro-1,3-dihydroindol-2-one (A4)

A3 (5.30 g, 10 mmol) is stirred in MeOH (10 mL)/2 N NaOH (10 mL) for 30 min at 80° C. The reaction mixture is acidified with 1 N HCl, the precipitate is filtered off and stirred in acetic acid (10 mL) for 1 h at boiling temperature. The mixture is cooled to RT, the precipitate is isolated by filtration and digested with water. Yield: 2.18 g (68%)

Synthesis of a Basic Unsubstituted Indolinone Structure

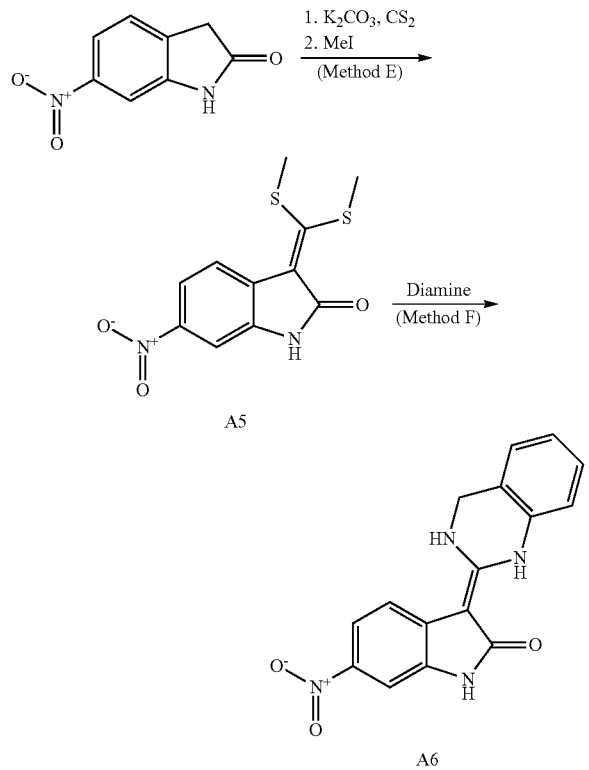

Method E—3-(Bismethylsulphanylmethylene)-6-nitro-1,3-dihydro-indol-2-one (A5)

K₂CO₃ (3.88 g, 28.07 mmol) is added to A4 (1 g, 5.61 mmol) and CS₂ (375 µL) in anhydrous DMF (30 mL) at 15° C. and stirred for 1 h. Methyl iodide (775 µL) in anhydrous DMF (5 mL) is added and the mixture is stirred for 6 h at RT. The reaction mixture is stirred into water (150 mL), the precipitate is suction filtered, washed repeatedly with water and digested once with MeCN. Yield: 1.17 g (74%)

Method F—Cyclic Vinylogous Amides/Analogue Compounds to A6

A5 (350 mg, 1.24 mmol) and 2-aminobenzylamine are stirred in n-butanol for 15 min at 150° C. in the microwave. The precipitate formed is filtered off, washed with ether and dried. Yield: 300 mg (78%)

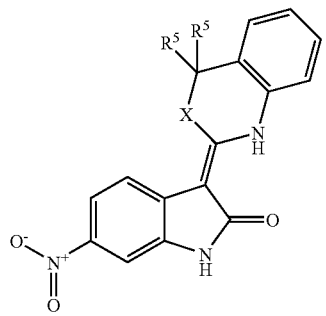

| No. | R⁵ | R⁵ | X | Yield [%] |
|---|---|---|---|---|
| A6 | H | H | NH | 78 |
| A7 | H | H | O | 59 |
| A8 | Me | Me | NH | 49 |

| No. | X | Yield [%] |
|---|---|---|
| A9 | N—iPr | quant. |
| A10 | NH | 88 |
| A11 | O | 90 |

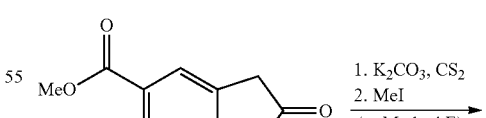

| No. | X | Yield [%] |
|---|---|---|
| A9 | N—iPr | quant. |
| A10 | NH | 88 |
| A11 | O | 90 |
| A12 | (1-methylpiperidin-4-yl)NH₂ | 38 |

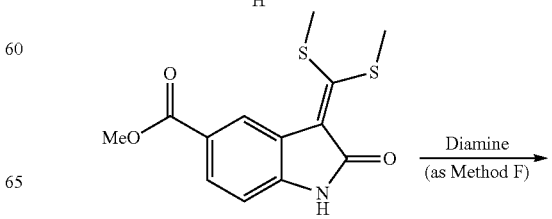

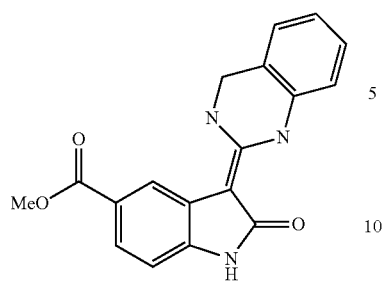

Analogously to Method E, starting from 5-methoxycarbonyl-1,3-dihydroindol-2-one, the corresponding compound 3-(bismethylsulphanylmethylene)-5-methoxycarbonyl-1,3-dihydro-indol-2-one (A13) is obtained, which is reacted analogously to Method F to form the corresponding cyclic vinylogous amides.

| No. | R⁵/R⁵ | X | Yield [%] |
|---|---|---|---|
| A14 | H/H | NH | 99 |
| A15 | Me/Me | NH | 87 |
| A16 | Me/Me | NH | 99 |

Preparation of the Aniline Components

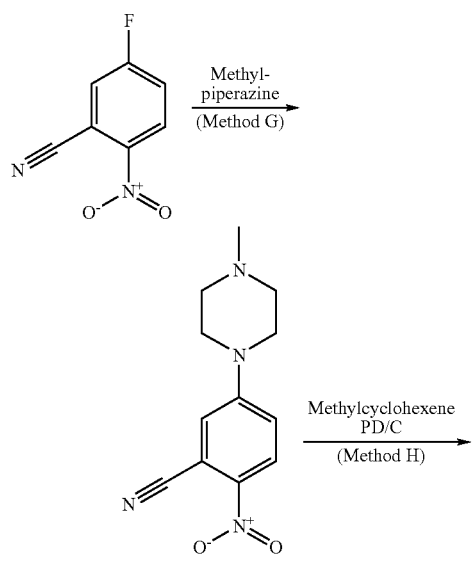

Method G—5-(4-Methylpiperazin-1-yl)-2-nitrobenzonitrile (A17)

2-Fluoro-5-nitrobenzonitrile (6.60 g, 39.7 mmol), N-methylpiperazine (10.62 mL) and triethylamine (16.5 mL) are stirred in 2-propanol (50 mL) for 16 h at RT and for 3 h at reflux temperature. The product is obtained by filtration, digested with water, 2-propanol and ether and dried. Yield: 8.90 g (91%)

| No. | R | Yield [%] |
|---|---|---|
| A17 | N-methylpiperazinyl | 91 |
| A18 | N-methylhomopiperazinyl | 90 |
| A19 | morpholinyl | 100 |

Method H—Reduction of the Nitro Group (A20)

A17 (500 mg, 2.03 mmol), 4-methyl-1-cyclohexene (1.22 mL) and Pd/C (100 mg) are stirred in THF (5 mL)/MeOH (5 mL) for 25 min. at 80° C. in the microwave. The catalyst is filtered off and the filtrate is evaporated down. Yield: 420 mg (96%)

| No. | R | Yield [%] |
|---|---|---|
| A20 | N-methylpiperazinyl | 96 |
| A21 | N-methylhomopiperazinyl | 81 |
| A22 | morpholinyl | 100 |

Method I—Reduction to Form the Benzylamine

A20 (420 mg, 1.94 mmol) and Raney nickel (100 mg) are hydrogenated in methanolic ammonia (2 mol/L, 60 mL) at RT and 3 bar hydrogen pressure. The catalyst is filtered off and the filtrate is evaporated down. Yield: 343 mg (80%)

| No. | R | Yield [%] |
|---|---|---|
| A23 | N-methylpiperazinyl | 80 |
| A24 | N-methylhomopiperazinyl | quant. |
| A25 | morpholinyl | 100 |

Method J—5-(4-Methylpiperazin-1-yl)-2-nitrobenzaldehyde (A26)

2-Fluoro-5-nitrobenzaldehyde (2.50 g, 15 mmol), N-methylpiperazine (1.8 mL) and potassium carbonate (3.10 g, 22 mmol) are stirred in anhydrous DMSO (20 mL) for 2 h at 70° C. The reaction mixture is mixed with water, the product is obtained by filtration, digested with water and dried. Yield: 3.41 g (93%)

| No. | R | Yield [%] |
|---|---|---|
| A26 | 4-methylpiperazin-1-yl | 93 |
| A27 | (S)-3-methylpiperazin-1-yl | 98 |
| A28 | 2-Boc-2,5-diazabicyclo[2.2.1]heptanyl | 96 |
| A29 | morpholinyl | 66 |

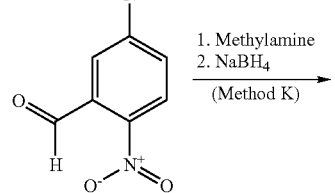

Method K—Reductive Amination (A30)

A26 (1.50 g, 6.02 mmol) and methylamine (70% in water, 0.8 mL) are stirred in methanol for 15 min at RT. NaBH₄ (175 mL 4.63 mmol) is added and the mixture is stirred for 15 min at RT. The reaction mixture is used in the next step without any further working up.

Method L—Reduction of the Nitro Group (A31)

The crude product obtained from A30 is stirred with palladium on activated charcoal (100 mg) in MeOH (5 mL)/DCM (20 mL) for 2.5 h at RT at a hydrogen pressure of 5 bar. The catalyst is filtered off and the filtrate is evaporated down. The residue is dissolved in DCM, washed with water and dilute potassium carbonate solution, dried, filtered and evaporated down. Yield: 1.01 g (72%).

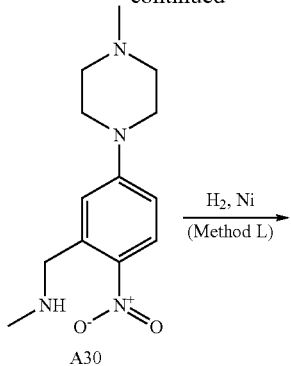

| No. | $R^x$ | $R^y$ | Yield [%] |
|---|---|---|---|
| A31 | N-methylpiperazinyl | H | 72 |
| A32 | N-methylpiperazinyl | iPr | 93 |
| A33 | N-methylpiperazinyl | iBu | 95 |
| A34 | N-methylpiperazinyl | tBu | 87 |

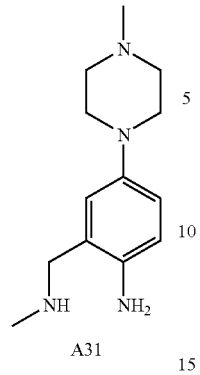

| No. | $R^x$ | $R^y$ | Yield [%] |
|---|---|---|---|
| A35 | N-methylpiperazinyl | iBu | 96 |
| A36 | N-methylpiperazinyl | cyclopentyl | 99 |
| A37 | N-methylpiperazinyl | sec-butyl | 92 |
| A38 | 2-methylpiperazinyl | iPr | 73 |
| A39 | H | iPr | 78 |
| A40 | H | N-methylpiperidin-4-yl | 93 |
| A41 | H | Me | 100 |
| A42 | H | Et | 83 |
| A43 | morpholinyl | Me | 71 |

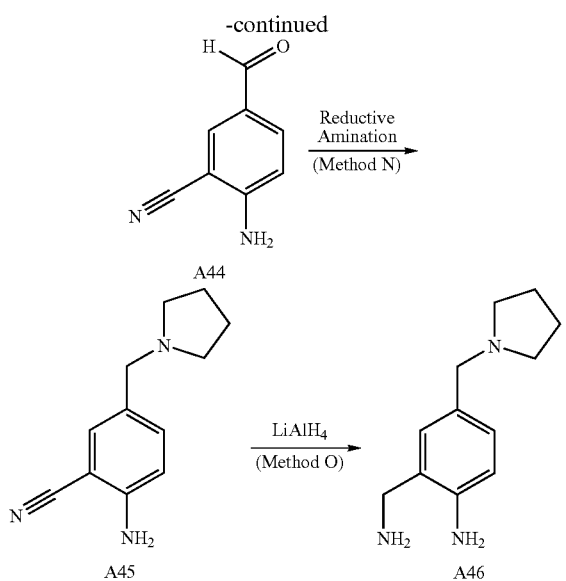

Method M—2-Amino-5-formylbenzenzonitrile (A44)

2-Fluoro-5-formylbenzonitrile (500 mg, 3.53 mmol) in THF (7.5 mL) and conc. aqueous ammonia (2.6 mL) are stirred for 900 s at 100° C. in the microwave. The reaction solution is evaporated down, the residue is combined with 1 N HCl, the precipitate is filtered off, washed with water until neutral and dried in vacuo. Yield: 390 mg (80%)

Method N—Reductive amination (A45)

$NaBH(OAc)_3$ (2.32 g 10.9 mmol) and glacial acetic acid (0.31 mL) are added to A44 (800 mg, 5.47 mmol) and pyrrolidine (2.26 mL, 27.4 mmol) in anhydrous $CH_2Cl_2$ (20 mL) and stirred for 2 h at RT. Concentrated $K_2CO_3$ solution is added and the organic phase is extracted exhaustively with 1 N HCl. The combined aqueous phase is made basic with $K_2CO_3$ and exhaustively extracted with EtOAc. The combined organic phase is washed with NaCl solution, dried, filtered and evaporated down. Yield: 935 mg (85%).

Method O—Reduction to Form the Benzylamine (A46)

A45 (878 mg, 4.36 mmol) in anhydrous THF (10 mL) is added to a solution of $LiAlH_4$ (1 M in THF, 12 mL) within 30 min at 0° C. and stirred for 16 h at RT. Water (1 mL) in THF (1 mL) is added to the mixture at 0° C., it is diluted with THF (20 mL) and 1 N NaOH (25 mL). The organic phase is separated off and the aqueous phase is exhaustively extracted with THF. The combined organic phase is dried, filtered and evaporated down. Yield: 676 mg (75%).

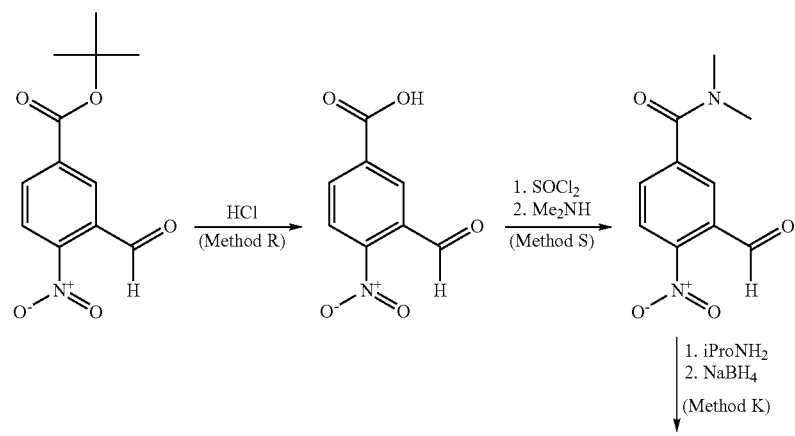

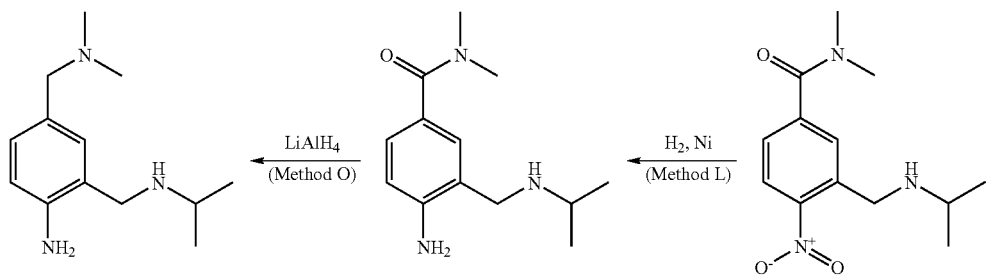

Method R—Cleaving of the tert.-butyl ester (A47)

Tert-.butyl 3-formyl-4-nitrobenzoate (2 g, 7.96 mmol) is stirred in 4 N HCl in dioxane (20 mL) for 3 h at 55° C. and for 12 h at RT. The reaction mixture is evaporated down. Yield: 1.59 g (88%)

Method S—Amide Formation (A48 and A49)

A47 (1.59 g, 7.01 mmol) in anhydrous toluene (30 mL) is combined with thionyl chloride (350 μL) and DMF (100 μL) and stirred for 2 h at boiling temperature. The reaction mixture is evaporated down and the residue is taken up in anhydrous THF (10 mL). 2 M Me$_2$NH in THF (7.7 mL) is added at 0° C. and stirred for 1 h at RT. The reaction mixture is evaporated down and the residue is divided between EtOAc and 1 N HCl. The organic phase is washed with saturated K$_2$CO$_3$ solution and NaCl solution, dried, filtered and evaporated down Yield 930 mg (54%)

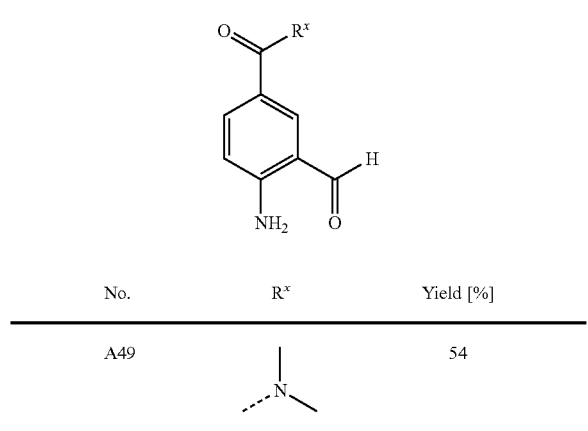

| No. | R$^x$ | Yield [%] |
|---|---|---|
| A49 | ![structure] | 54 |

The reductive amination with subsequent reduction of the nitro group is carried out according to Method K and Method L.

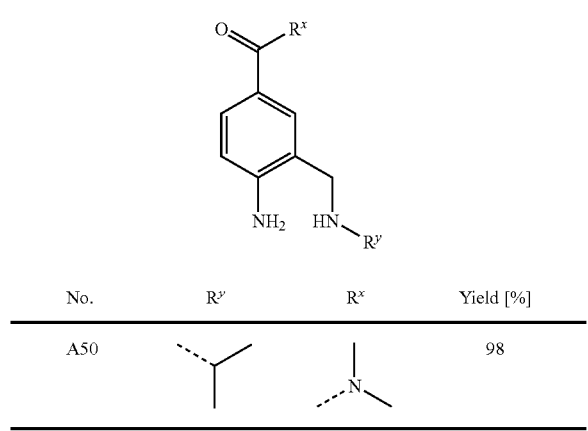

| No. | R$^y$ | R$^x$ | Yield [%] |
|---|---|---|---|
| A50 | ![structure] | ![structure] | 98 |

The reduction to the benzylamine is carried out according to Method O.

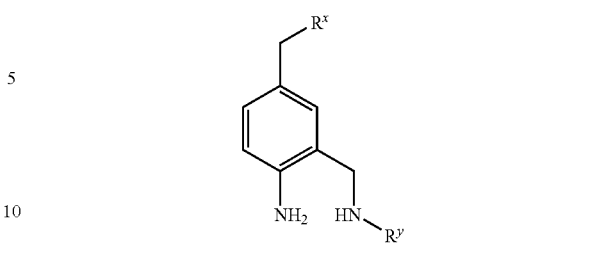

| No. | R$^y$ | R$^x$ | Yield [%] |
|---|---|---|---|
| A51 | ![structure] | ![structure] | 80 |

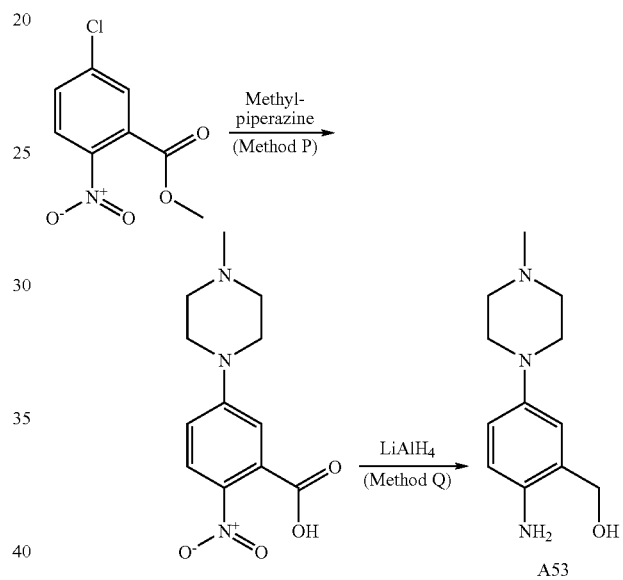

Method P—5-(4-Methylpiperazin-1-yl)-2-nitrobenzoic acid (A52)

Methyl 5-chloro-2-nitrobenzoate acid (1 g, 4.50 mmol) and N-methylpiperazine (3 mL, 27 mmol) are stirred in the microwave for 30 min at 150° C. The reaction mixture is stirred in water (50 mL), the pH is adjusted to 5 with NH$_4$Cl, and the mixture is washed with EtOAc. The aqueous phase is freeze-dried, the residue is stirred with THF (200 mL) and filtered. The filtrate is evaporated down and the residue is digested with MeCN. Yield: 434 mg (36%).

Method Q—Reduction to Form the benzylalcohol (A53)

LiAlH$_4$ (248 mg, 38 mmol) is added at 0° C. to A52 (434 mg, 1.64 mmol) in anhydrous ether (20 mL) and stirred for 48 h at RT. EtOAc (10 mL) is added and the mixture is stirred for 1 h at RT. The precipitate is filtered off and extracted with THF, the combined filtrates are evaporated down. Yield: 257 mg (71%).

Synthesis of Substituted Indolinones
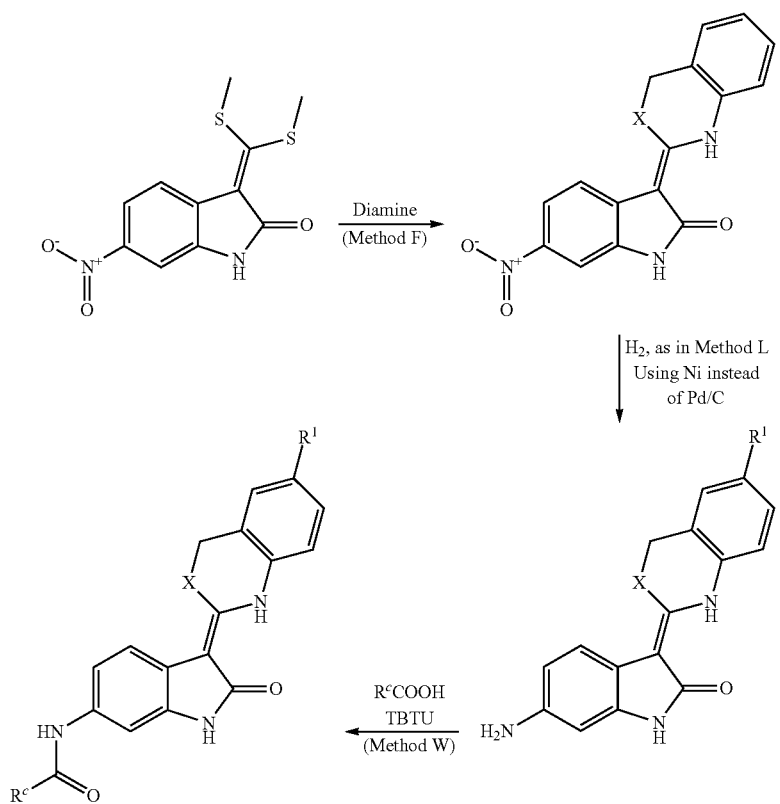
The cyclic vinylogous amides are prepared according to Method F using isopropanol as solvent.
| No. | R¹ | X | Yield [%] |
|---|---|---|---|
| A54 | *piperazine-N-Boc* | O | 79 |
| A55 | *4-methylpiperazine* | O | 12 |
| A56 | *4-methylpiperazine* | N | 28 |

-continued

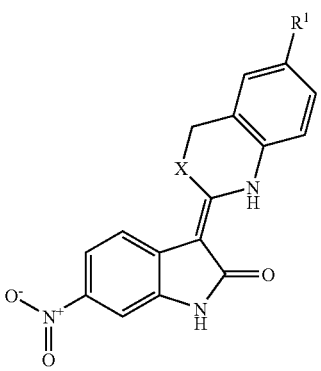

| No. | R¹ | X | Yield [%] |
|---|---|---|---|
| A57 | -CH2-pyrrolidin-1-yl | N | 96 |
| A58 | 4-methylpiperazin-1-yl | isopropyl | 55 |
| A59 | 4-methylpiperazin-1-yl | (bond) | 81 |
| A60 | 4-methylpiperazin-1-yl | ethyl | quant. |
| A61 | 4-methylpiperazin-1-yl | isopropyl | quant. |
| A62 | 4-methylpiperazin-1-yl | tert-butyl | 92 |
| A63 | 4-methylpiperazin-1-yl | sec-butyl | quant. |
| A64 | (S)-3-methylpiperazin-1-yl | isopropyl | quant. |
| A65 | 4-methyl-1,4-diazepan-1-yl | H | 75 |
| A66 | 4-methylpiperazin-1-yl | cyclopentyl | 73 |

-continued

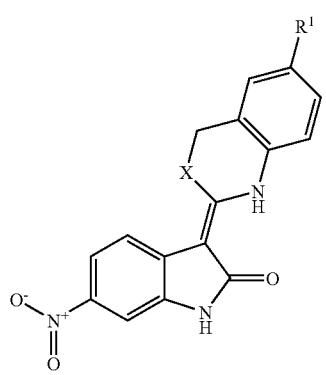

| No. | R¹ | X | Yield [%] |
|---|---|---|---|
| A67 | H | isopropyl | 77 |
| A68 | H | 1-methylpiperidin-4-yl | 81 |
| A69 | -CH2-N(CH3)2 | isopropyl | 48 |

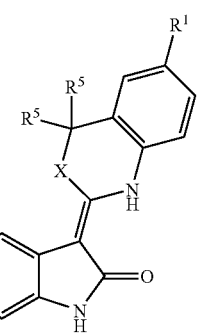

| No. | R¹ | X | Yield [%] |
|---|---|---|---|
| A70 | morpholin-4-yl | N | 100 |
| A71 | 4-methylpiperazin-1-yl | N | 99 |
| A72 | NH₂ | N | 48 |
| A73 | tert-butoxycarbonyl | N | 68 |
| A74 | morpholin-4-yl | N—Me | 72 |
| A75 | 4-methylpiperazin-1-yl | N—Me | 85 |
| A76 | H | N—Me | 100 |
| A77 | H | N—Et | 89 |
| A78 | H | N—iPr | 87 |

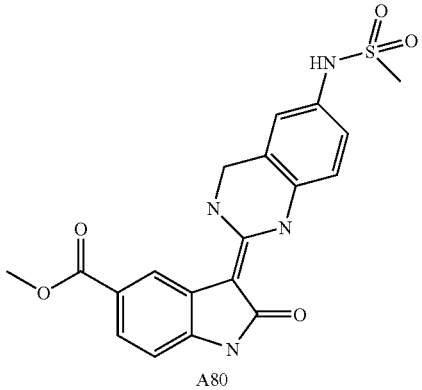

A80

Reaction with Sulphonyl Chlorides (A80)

A79 (469 mg, 1.5 mmol) is dissolved in THF (50 mL) and combined with triethylamine (650 μL, 4.5 mmol) and methylsulphonyl chloride (350 μL, 4.5 mmol) and stirred for 3 days at 50° C. After elimination of the solvent the crude product is taken up in methanol and purified by preparative HPLC-MS. Yield: 162 mg (27%)

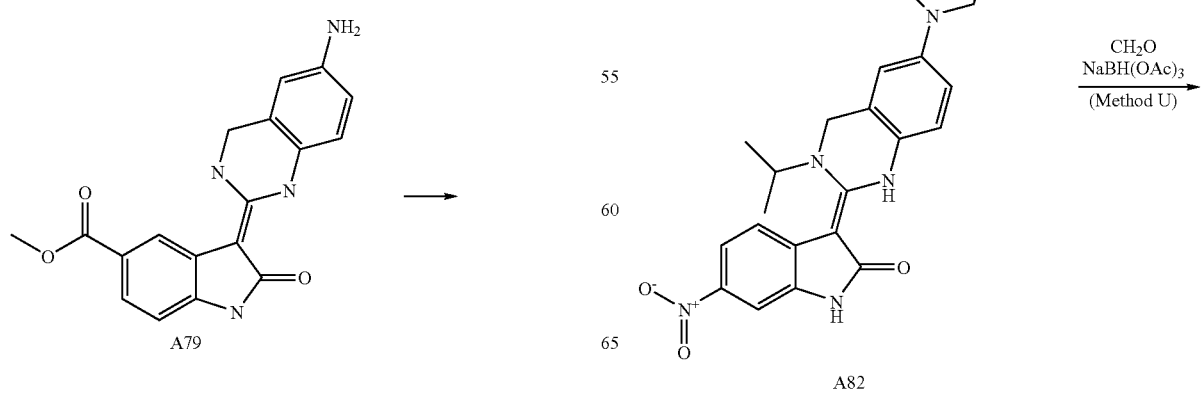

Method T—Cleaving of the boc Protective Group (A82)

A81 (886 mg, 1.62 mmol) is stirred in CH$_2$Cl$_2$ (10 mL)/TFA (2.55 mL) for 1 h at ambient temperature. The reaction solution is diluted with CH$_2$Cl$_2$ and neutralised with K$_2$CO$_3$. The mixture is diluted with water and extracted exhaustively with EtOAc. The combined organic phases are dried, filtered and evaporated down. Yield: 700 mg (97%)

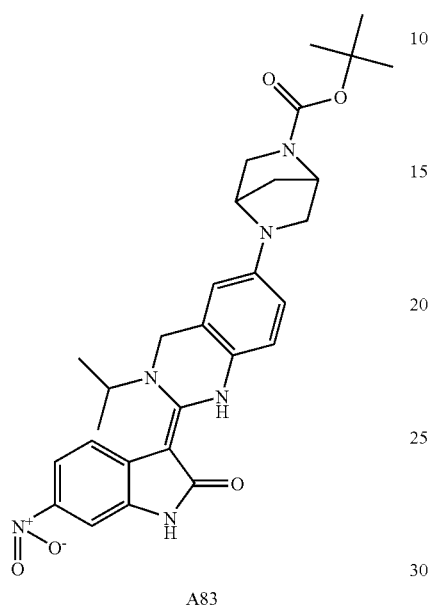

A83

Method U—Reductive Amination (A83)

A82 (723 mg, 1.62 mmol) in CH$_2$Cl$_2$ (25 mL)/MeOH (5 mL) and 37% formaldehyde in water (5 mL) are stirred for 1 h at RT. NaBH(OAc)$_3$ (1.06 g, 5.02 mmol) is added batchwise at 0° C., then the mixture is stirred for 3 h at RT. The reaction solution is divided between CH$_2$Cl$_2$ and saturated K$_2$CO$_3$ solution, the organic phase is washed with saturated K$_2$CO$_3$ solution, dried, filtered and evaporated down. Yield: 750 mg (quant.)

| No. | Structure | Educt | Method | Yield [%] |
|-----|-----------|-------|--------|-----------|
| A84 | 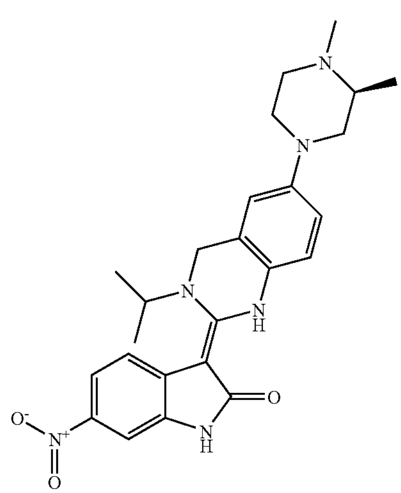          |       | U      | quant.    |

The reduction of the nitro group to form the aniline is carried out using the General Working Method specified under Method L.

Method W—General Working Method for Amide Formation

Triethylamine (3 equiv.) and TBTU (1.2 equiv.) are added to a solution of the carboxylic acid (1 equiv.) in anhydrous DMSO (10-20 μL/mg amino compound) and shaken for 5 min at RT. The amino compound is added and the mixture is shaken for 30 min at RT. The reaction solution is filtered and purified by preparative HPLC.

Aniline Components:

The following components are prepared analogously to methods G, H and I. The reduction of the cyano group may be carried out both with Raney nickel as described in Method I and also with borane/THF complex.

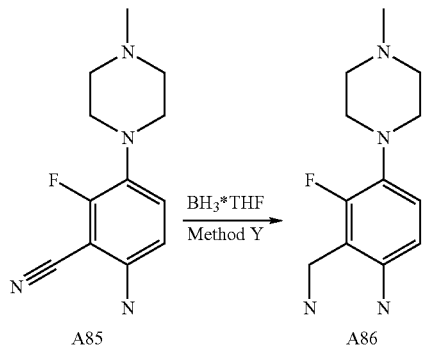

A88 (340 mg) is dissolved in 50 mL THF and mixed with borane/THF complex (4.3 mL, 1 mmol/mL). This reaction mixture is refluxed for 16 h. The reaction solution is combined with methanol and the solvent is eliminated in vacuo. The crude mixture is purified by preparative HPLC.

The following components are prepared analogously to methods J, K and I. For components wherein $R_{y'}$ does not denote H, 5-chloro-2-nitro-acetophenone is used as the starting material.

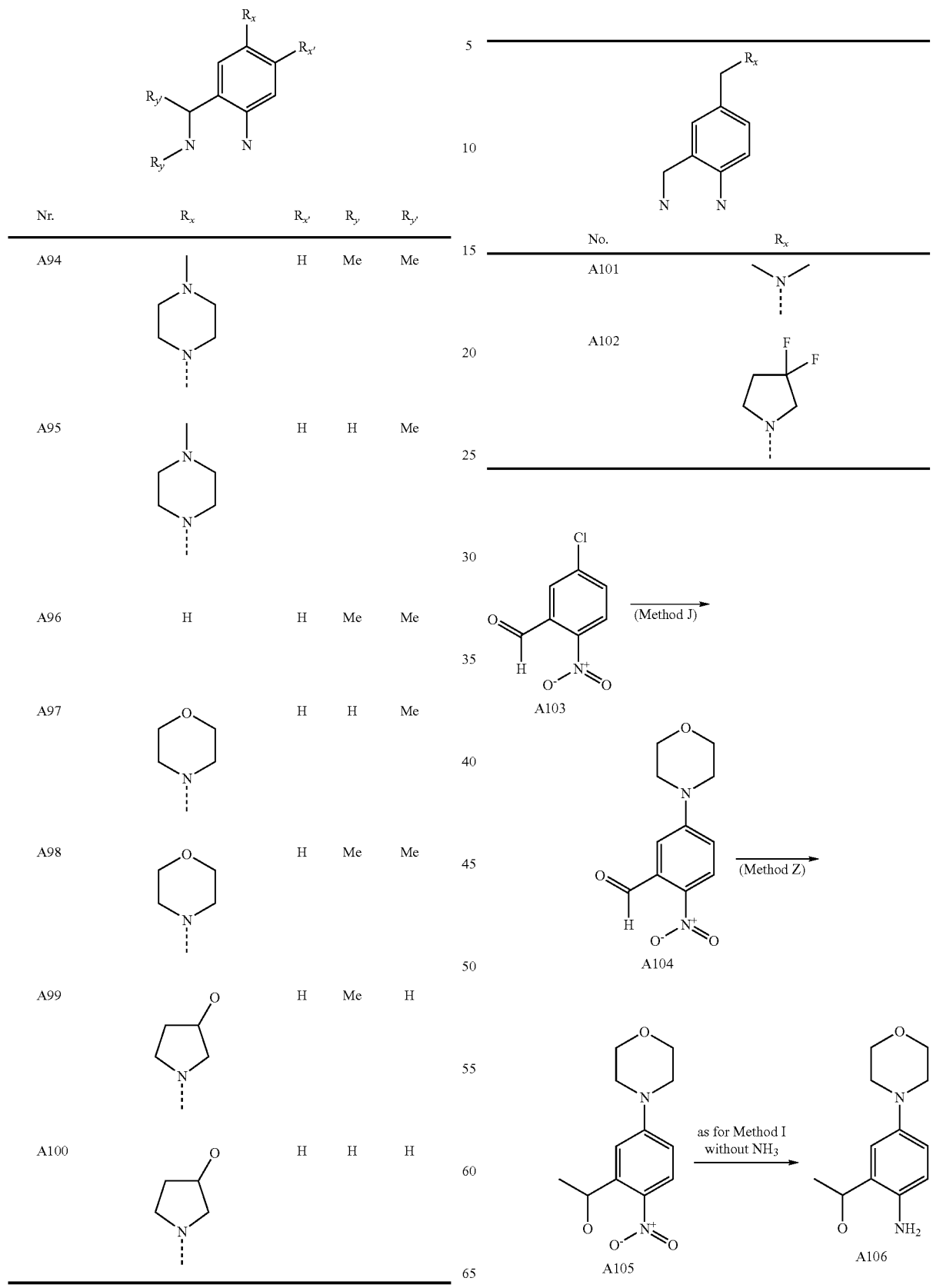

Method Z

A100 (1 g) is dissolved in 25 mL ethanol and combined with sodium borohydride (166 mg). This reaction mixture is stirred for 16 h at 20° C. Then 25 mL saturated sodium hydrogen carbonate solution are added to the reaction solution, it is stirred for 1 h and the organic constituents are eliminated in vacuo. The aqueous phase is extracted with diethyl ether, the organic phase is dried and the solvent is eliminated in vacuo. The following components are prepared analogously to methods J, Z and I. For components wherein $R_{y'}$ is H, 5-fluoro-2-nitro-benzaldehyde is used as starting material.

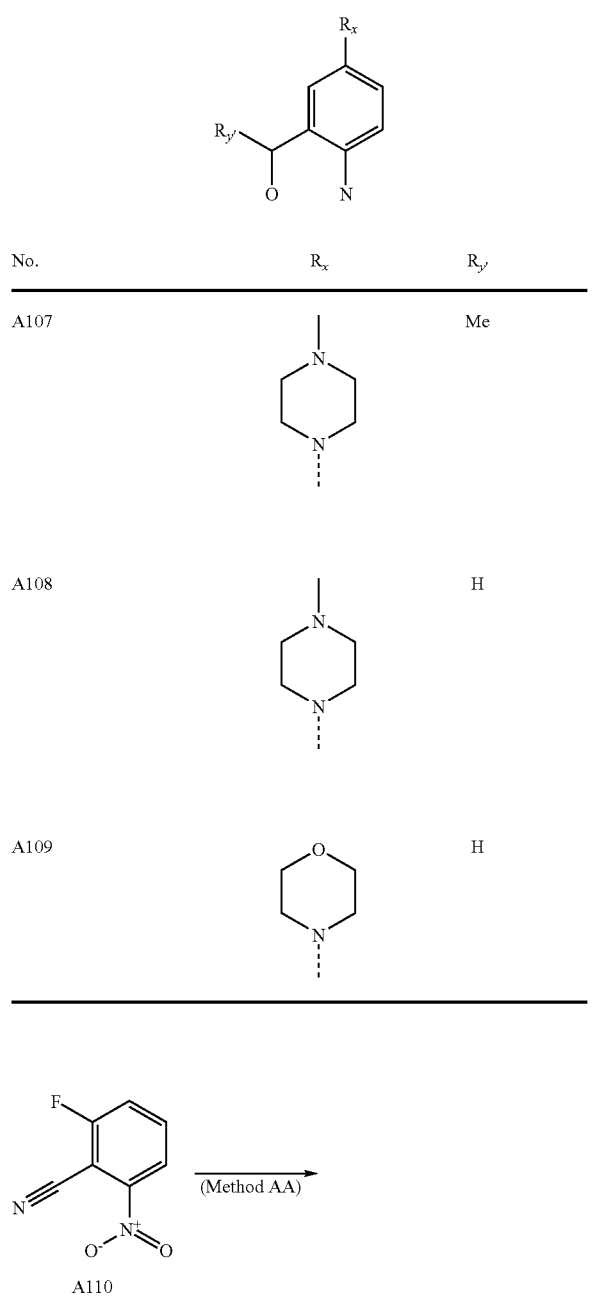

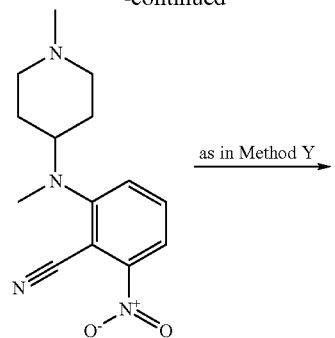

A111

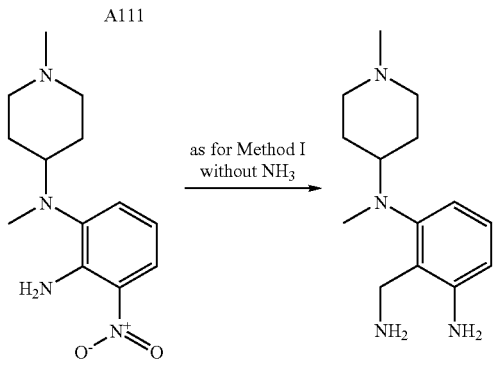

A112   A113

Method AA

A105 (500 mg), 1-methyl-(4-methylamino)piperidine (440 μL) and Hünig base (600 μL) are suspended in 1.5 mL butanol and stirred for 1 h at 150° C. in a Biotage microwave. The reaction mixture is combined with water and DCM, the organic phase is separated off and dried.

The following components are prepared analogously to methods AA, Y and I.

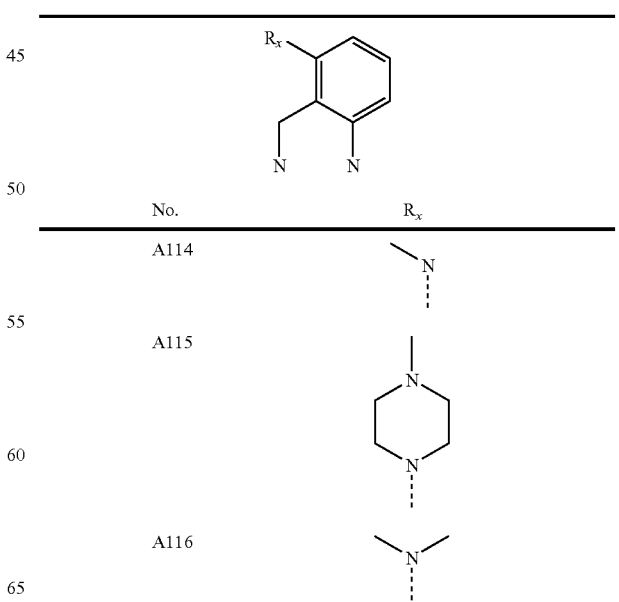

-continued

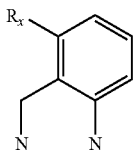

| No. | $R_x$ |
|---|---|
| A117 | 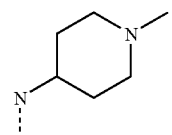 |

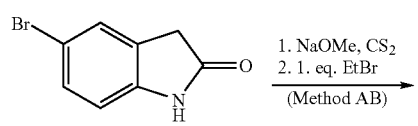

A118

1. NaOMe, $CS_2$
2. 1. eq. EtBr
(Method AB)

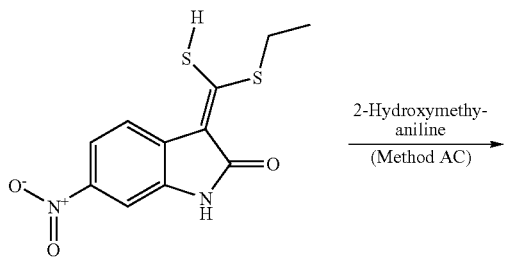

A119

2-Hydroxymethyl-aniline
(Method AC)

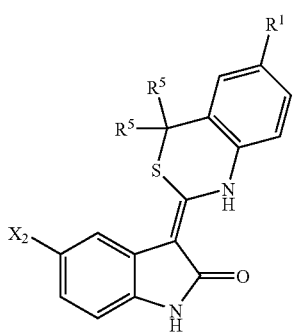

A120

Method AB: A119

NaOMe (0.185 g) is added to A118 (0.3 g) and $CS_2$ (111 μL) in anhydrous DMSO (10 mL) at 15° C. and the mixture is stirred for 1 h. Ethylbromide (106 μL) is added and the mixture is stirred for 14 h at RT. The reaction mixture is stirred into saturated $NH_4Cl$ solution (20 mL) and extracted with $CH_2Cl_2$. The organic phase is washed with saturated NaCl solution (20 mL), dried and concentrated by rotary evaporation.

Method AC: A120

2-Aminobenzylalcohol (98.13 mg) is added to A119 (0.21 g) in 1 mL isopropanol and the mixture is stirred for 4 h at 100° C. The reaction mixture is stirred into water (20 mL) and extracted with $CH_2Cl_2$. The organic phase is washed with saturated NaCl solution (20 mL), dried and freed from the solvent in vacuo.

The following products are obtained analogously to methods AB and AC from the correspondingly substituted indolinones and the suitably configured 2-aminobenzyl-alcohols (e.g. prepared analogously to Method P/Q, J/Z/I or according to other general methods known to the skilled man).

| No. | $R^5/R^5$ | $R^1$ | $X_2$ |
|---|---|---|---|
| A121 | H/H | 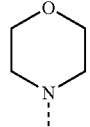 | $NO_2$ |
| A122 | H/H | 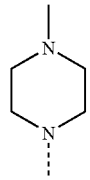 | $NO_2$ |
| A123 | H/H | 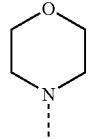 | COOMe |
| A124 | H/H | 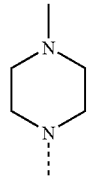 | COOMe |
| A125 | $CH_3$/H | 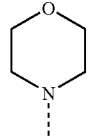 | COOMe |
| A126 | H/H | H | COOMe |

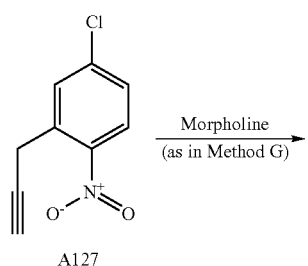
A127
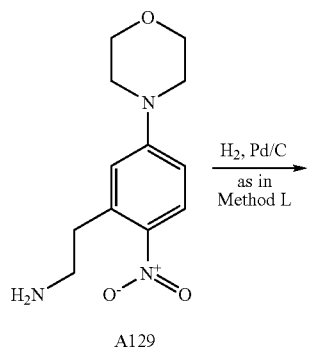
A128
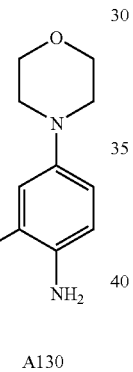
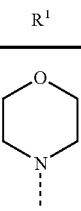
A129 → A130 (H₂, Pd/C as in Method L)
The following components are prepared analogously to Method G, Y and L.
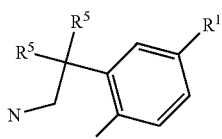
| No. | R⁵/R⁵ | R¹ |
|---|---|---|
| A131 | H/H | 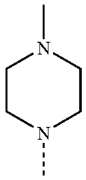 |
-continued
| No. | R⁵/R⁵ | R¹ |
|---|---|---|
| A132 | H/H | (4-methylpiperazin-1-yl) |
| A133 | H/H | F |
| A134 | H/H | 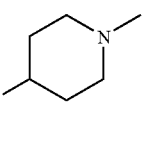 |
| A135 | H/H | 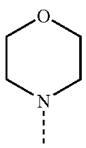 |
| A136 | —CH₂—CH₂— | 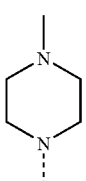 |
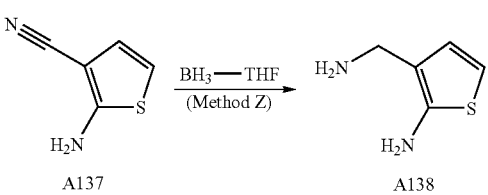
A137 → A138 (BH₃—THF, Method Z)
A137 is reacted analogously to Method Y to form A138.

Examples 1-51
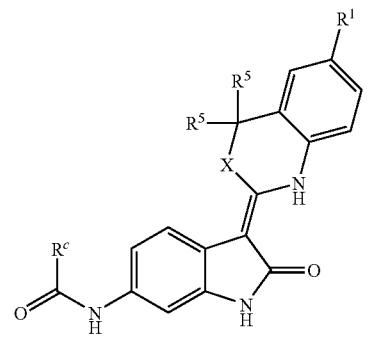
| Ex. | $R^c$ | $R^1$ | $R^5/R^5$ | X | $t_{ret}$ [min] | $[M+H]^+$ | $UV_{max}$ [nm] | HPLC |
|---|---|---|---|---|---|---|---|---|
| 1 | styryl (PhCH=CH-) | H | H/H | NH | 2.05 | 409 | 278 | A |
| 2 | indolin-2-yl | H | H/H | NH | 1.97 | 424 | 348 | A |
| 3 | 1H-benzimidazol-2-yl | H | H/H | NH | 1.98 | 423 | 361 | A |
| 4 | 4-methyl-1H-imidazol-2-yl | H | H/H | O | 1.79 | 388 | 364 | A |
| 5 | 1H-benzimidazol-2-yl | H | Me/Me | NH | 2.12 | 451 | 366 | A |
| 6 | 1H-benzimidazol-2-yl | 4-methylpiperazin-1-yl | H/H | NH | 1.48 | 521 | 360 | A |
| 7 | 4-methyl-1H-imidazol-2-yl | 4-methylpiperazin-1-yl | H/H | N—Me | 0.12 | 499 | 311 | A |
| 8 | 1H-benzimidazol-2-yl | 4-methylpiperazin-1-yl | H/H | N—Me | 0.12 | 535 | 307 | A |

-continued

| Ex. | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 9 | benzimidazol-2-yl | 4-methyl-1,4-diazepan-1-yl | H/H | NH | 1.52 | 535 | 367 | A |
| 10 | 4-methyl-1H-imidazol-2-yl | 4-methyl-1,4-diazepan-1-yl | H/H | NH | 1.34 | 499 | 364 | A |
| 11 | 4-methyl-1H-imidazol-2-yl | 4-methylpiperazin-1-yl | H/H | N—Et | 1.23 | 513 | 312 | A |
| 12 | styryl | 4-methylpiperazin-1-yl | H/H | N—Et | 1.47 | 535 | 291 | A |
| 13 | benzimidazol-2-yl | 4-methylpiperazin-1-yl | H/H | N—Et | 1.47 | 549 | 306 | A |
| 14 | 1H-imidazol-2-yl | 4-methylpiperazin-1-yl | H/H | N—Et | 0.12 | 499 | 309 | A |
| 15 | benzimidazol-2-yl | (pyrrolidin-1-yl)methyl | H/H | NH | 1.52 | 506 | 365 | A |
| 16 | 4-methyl-1H-imidazol-2-yl | 4-methylpiperazin-1-yl | H/H | N—iPr | 0.13 | 527 | 312 | A |
| 17 | styryl | 4-methylpiperazin-1-yl | H/H | N—iPr | 1.55 | 549 | 289 | A |

-continued

[Core structure: 3-(substituted-methylene)-2-oxoindoline with R$^c$C(O)NH- at 6-position of indoline, and a fused dihydroquinazoline-type ring bearing R$^1$, R$^5$/R$^5$, and X]

| Ex. | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 18 | benzimidazol-2-yl | 4-methylpiperazin-1-yl | H/H | N—iPr | 1.52 | 563 | 305 | A |
| 19 | imidazol-2-yl | 4-methylpiperazin-1-yl | H/H | N—iPr | 0.12 | 513 | 376 | A |
| 20 | benzimidazol-2-yl | 4-methylpiperazin-1-yl | H/H | O | 1.94 | 522 | 382 | B |
| 21 | benzimidazol-2-yl | 4-(cyclopropylmethyl)piperazin-1-yl | H/H | O | 2.51 | 562 | 391 | B |
| 22 | imidazo[4,5-b]pyridin-2-yl | 4-methylpiperazin-1-yl | H/H | N—iPr | 1.69 | 564 | 383 | B |
| 23 | imidazo[4,5-b]pyridin-2-yl | 4-methylpiperazin-1-yl | H/H | N—Me | 1.54 | 536 | 377 | B |
| 24 | imidazo[4,5-b]pyridin-2-yl | 4-methylpiperazin-1-yl | H/H | N—Et | 1.61 | 550 | 381 | B |
| 25 | imidazo[4,5-b]pyridin-2-yl | 4-methylpiperazin-1-yl | H/H | N—cyclopentyl | 1.80 | 590 | 386 | B |

-continued

| Ex. | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 26 | benzimidazol-2-yl (NH) | 4-methylpiperazin-1-yl | H/H | N-cyclopentyl | 2.07 | 589 | 384 | B |
| 27 | 4-methyl-1H-imidazol-2-yl | 4-methylpiperazin-1-yl | H/H | N-cyclopentyl | 1.88 | 553 | 380 | B |
| 28 | (E)-styryl | 4-methylpiperazin-1-yl | H/H | N-cyclopentyl | 2.14 | 575 | 387 | B |
| 29 | 3H-imidazo[4,5-b]pyridin-2-yl | pyrrolidin-1-ylmethyl | H/H | NH | 1.68 | 507 | 367 | B |
| 30 | benzothiophen-2-yl | 4-methylpiperazin-1-yl | H/H | N—iPr | 2.131 | 579 | 383 | B |
| 31 | benzofuran-2-yl | 4-methylpiperazin-1-yl | H/H | N—iPr | 2.07 | 563 | 384 | B |
| 32 | 7-methoxybenzofuran-2-yl | 4-methylpiperazin-1-yl | H/H | N—iPr | 2.06 | 593 | 385 | B |
| 33 | 5,6-dihydro-4H-cyclopenta[b]thiophen-2-yl | 4-methylpiperazin-1-yl | H/H | N—iPr | 2.10 | 569 | 380 | B |

-continued
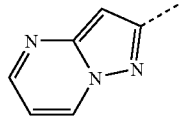
| Ex. | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 34 | 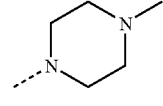 | 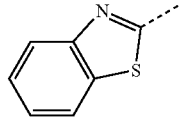 | H/H | N—iPr | 1.74 | 564 | 380 | B |
| 35 | 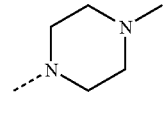 | 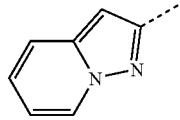 | H/H | N—iPr | 2.17 | 580 | 391 | B |
| 36 | 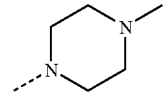 | 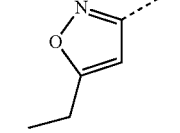 | H/H | N—iPr | 1.93 | 563 | 378 | B |
| 37 | 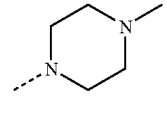 | 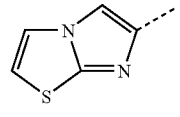 | H/H | N—iPr | 1.96 | 542 | 377 | B |
| 38 | 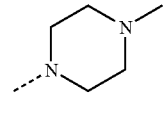 | 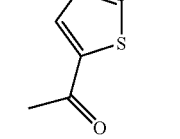 | H/H | N—iPr | 1.85 | 569 | 377 | B |
| 39 | 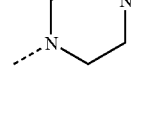 | 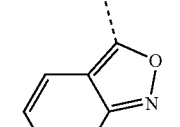 | H/H | N—iPr | 1.89 | 571 | 379 | B |
| 40 | 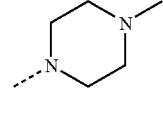 | 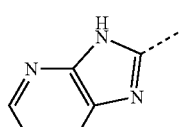 | H/H | N—iPr | 2.01 | 564 | 367 | B |
| 41 | 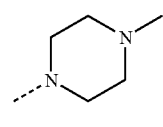 | 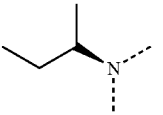 | H/H |  | 1.72 | 578 | 385 | B |

-continued

| Ex. | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 42 | 4-methyl-1H-imidazol-2-yl | 4-methylpiperazin-1-yl | H/H | (S)-sec-butyl-N-methyl | 1.84 | 541 | 385 | B |
| 43 | 1H-benzimidazol-2-yl | 4-methylpiperazin-1-yl | H/H | (S)-sec-butyl-N-methyl | 2.04 | 577 | 385 | B |
| 44 | styryl | 4-methylpiperazin-1-yl | H/H | (S)-sec-butyl-N-methyl | 2.08 | 563 | 385 | B |
| 45 | 3H-imidazo[4,5-b]pyridin-2-yl | dimethylaminomethyl | H/H | N—iPr | 1.76 | 523 | 384 | B |
| 46 | 1H-benzimidazol-2-yl | dimethylaminomethyl | H/H | N—iPr | 2.01 | 522 | 383 | B |
| 47 | styryl | H | H/H | 1-methylpiperidin-4-yl-N-methyl | 2.01 | 506 | 281 | B |
| 48 | 4-methyl-1H-imidazol-2-yl | H | H/H | 1-methylpiperidin-4-yl-N-methyl | 1.77 | 484 | 357 | B |
| 49 | 1H-benzimidazol-2-yl | H | H/H | 1-methylpiperidin-4-yl-N-methyl | 1.95 | 520 | 381 | B |

| Ex. | R^c | R^1 | R^5/R^5 | X | $t_{ret}$ [min] | $[M+H]^+$ | $UV_{max}$ [nm] | HPLC |
|---|---|---|---|---|---|---|---|---|
| 50 | imidazo[4,5-b]pyridin-2-yl | H | H/H | 1-methylpiperidin-4-yl(methyl)amino | 1.66 | 521 | 381 | B |
| 51 | 4-methyl-1H-imidazol-2-yl | H | H/H | N—iPr | 1.98 | 429 | 374 | B |

Examples 52-54

| Ex | R^c | X | $t_{ret}$ [min] | $[M+H]^+$ | $UV_{max}$ [nm] | HPLC |
|---|---|---|---|---|---|---|
| 52 | 1H-benzimidazol-2-yl | N—iPr | 1.80 | 451 | 311 | A |
| 53 | 1H-imidazol-2-yl | N—iPr | 1.49 | 401 | 282 | A |
| 54 | 4-methyl-1H-imidazol-2-yl | N—iPr | 1.55 | 415 | 282 | A |

Method X—General Working Method for the Saponification of Esters

A suspension of the ester in methanol (20-50 μL/mg ester) is combined with six equivalents of 1N NaOH and stirred for 5-24 h at 50° C. After cooling the reaction mixture is added to 1N HCL and the precipitate formed is filtered, washed and dried.

Examples 55-218

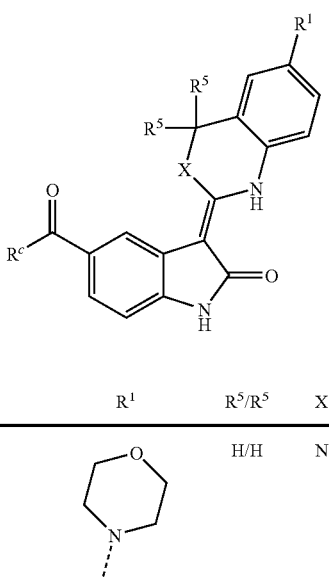

| Ex | $R^c$ | $R^1$ | $R^5/R^5$ | X | $t_{ret}$ [min] | $[M + H]^+$ | $UV_{max}$ [nm] | HPLC |
|---|---|---|---|---|---|---|---|---|
| 55 | butyl-N | morpholine | H/H | N | 1.57 | 448 | | D |
| 56 | 2-pyridyl-CH₂-N | morpholine | H/H | N | 1.48 | 483 | 346 | C |
| 57 | 4-pyridyl-CH₂-N | morpholine | H/H | N | 1.44 | 483 | 346 | C |
| 58 | 3-pyridyl-CH₂-N | morpholine | H/H | N | 1.5 | 497 | 346 | C |
| 59 | 3-furyl-CH₂-N | morpholine | H/H | N | 1.71 | 472 | | B1 |

-continued

| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 60 | pyridin-3-ylmethyl-NH- | morpholin-4-yl | H/H | N | 1.47 | 483 | 346 | C |
| 61 | 3-methoxypropyl-NH- | morpholin-4-yl | H/H | N | 1.49 | 464 | 346 | C |
| 62 | 2-methoxyethyl-NH- | morpholin-4-yl | H/H | N | 1.47 | 450 | 346 | C |
| 63 | furan-2-ylmethyl-NH- | morpholin-4-yl | H/H | N | 1.6 | 472 | 346 | C |
| 64 | 1-(pyridin-4-yl)ethyl-NH- | morpholin-4-yl | H/H | N | 1.58 | 497 | | B1 |
| 65 | (3-methylpyridin-4-yl)methyl-NH- | morpholin-4-yl | H/H | N | 1.43 | 497 | 346 | C |
| 66 | 1-(pyridin-2-yl)ethyl-NH- | morpholin-4-yl | H/H | N | 1.48 | 497 | 346 | C |

-continued
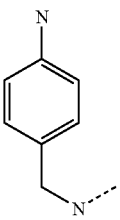
| Ex | R$^c$ | R$^1$ | R$^5$/R$^5$ | X | $t_{ret}$ [min] | [M + H]$^+$ | UV$_{max}$ [nm] | HPLC |
|---|---|---|---|---|---|---|---|---|
| 67 | 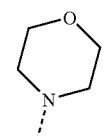 |  | H/H | N | 1.46 | 497 | 346 | C |
| 68 | 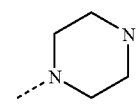 | 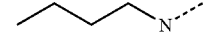 | H/H | N | 1.43 | 419 | | D |
| 69 | 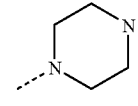 | 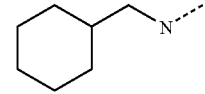 | H/H | N | 1.54 | 461 | | D |
| 70 | 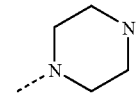 | 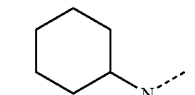 | H/H | N | 1.63 | 501 | | D |
| 71 | 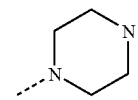 | 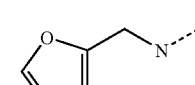 | H/H | N | 1.64 | 487 | 350 | C |
| 72 | 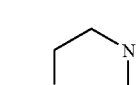 | 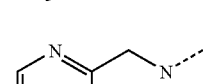 | H/H | N | 1.54 | 485 | 346 | C |
| 73 | 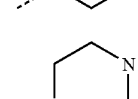 | 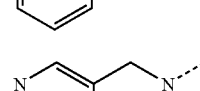 | H/H | N | 1.58 | 496 | 346 | B1 |
| 74 | 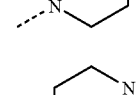 | 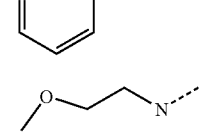 | H/H | N | 1.55 | 496 | 346 | B1 |
| 75 | 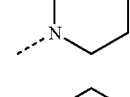 |  | H/H | N | 1.52 | 463 | 346 | B1 |
| 76 | 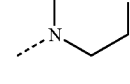 | | H/H | N | 1.5 | 496 | 346 | B1 |

-continued

| Ex | R^c | R^1 | R^5/R^5 | X | $t_{ret}$ [min] | $[M+H]^+$ | $UV_{max}$ [nm] | HPLC |
|---|---|---|---|---|---|---|---|---|
| 77 | methoxypropyl-N- | 4-methylpiperazinyl | H/H | N | 1.55 | 477 | 346 | B1 |
| 78 | furan-3-ylmethyl-N- | 4-methylpiperazinyl | H/H | N | 1.45 | 485 | 346 | D |
| 79 | 1-(pyridin-4-yl)ethyl-N- | 4-methylpiperazinyl | H/H | N | 1.47 | 510 | 346 | C |
| 80 | (3-methylpyridin-4-yl)methyl-N- | 4-methylpiperazinyl | H/H | N | 1.49 | 511 | 346 | C |
| 81 | 1-(pyridin-2-yl)ethyl-N- | 4-methylpiperazinyl | H/H | N | 1.51 | 510 | 346 | C |
| 82 | pyridin-2-ylmethyl-N- | morpholinyl | H/H | N—Me | 1.57 | 497 |  | B1 |
| 83 | butyl-N- | morpholinyl | H/H | N—Me | 1.47 | 462 |  | B1 |
| 84 | pyridin-4-ylmethyl-N- | morpholinyl | H/H | N—Me | 1.51 | 497 |  | B1 |

-continued

| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 85 | pyridin-3-ylmethylamino | morpholin-4-yl | H/H | N—Me | 1.53 | 497 | | B1 |
| 86 | H-N | morpholin-4-yl | H/H | N—Me | 1.33 | 406 | | B1 |
| 87 | (3-methylpyridin-4-yl)methylamino | morpholin-4-yl | H/H | N—Me | 1.57 | 511 | | B1 |
| 88 | 1-(pyridin-3-yl)ethylamino | morpholin-4-yl | H/H | N—Me | 1.58 | 511 | | B1 |
| 89 | 1-(pyridin-4-yl)ethylamino | morpholin-4-yl | H/H | N—Me | 1.58 | 511 | | B1 |
| 90 | (3-cyanophenyl)methylamino | morpholin-4-yl | H/H | N—Me | 1.6 | 511 | | B1 |
| 91 | furan-2-ylmethylamino | morpholin-4-yl | H/H | N—Me | 1.68 | 486 | | B1 |

-continued
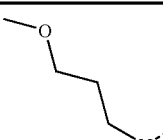
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 92 | 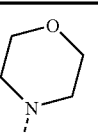 | 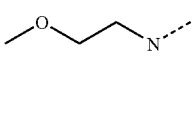 | H/H | N—Me | 1.55 | 478 | | B1 |
| 93 | 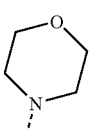 | 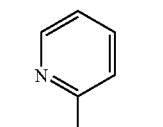 | H/H | N—Me | 1.49 | 464 | | B1 |
| 94 | 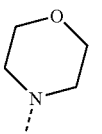 | 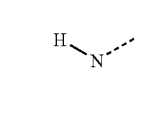 | H/H | N—Me | 1.65 | 511 | | B1 |
| 95 | 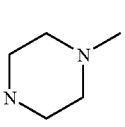 | 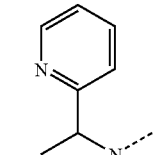 | H/H | N—Me | 1.35 | 419 | | B1 |
| 96 | 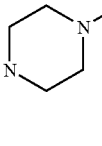 | 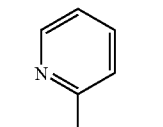 | H/H | N—Me | 1.64 | 524 | | B1 |
| 97 | 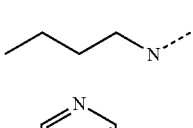 | H | H/H | N—Et | 1.65 | 426 | | B1 |
| 98 | 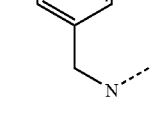 | H | H/H | N—Et | 1.86 | 391 | | B1 |
| 99 |  | H | H/H | N—Et | 1.57 | 426 | | B1 |

-continued
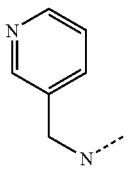
| Ex | R<sup>c</sup> | R<sup>1</sup> | R<sup>5</sup>/R<sup>5</sup> | X | t<sub>ret</sub> [min] | [M + H]<sup>+</sup> | UV<sub>max</sub> [nm] | HPLC |
|---|---|---|---|---|---|---|---|---|
| 100 |  | H | H/H | N—Et | 1.60 | 426 | | B1 |
| 101 |  | H | H/H | N—Et | 1.36 | 335 | | B1 |
| 102 |  | H | H/H | N | 1.56 | 321 | | A |
| 103 |  | H | H/H | N | 1.68 | 335 | | A |
| 104 |  | H | H/H | N | 1.79 | 349 | | A |
| 105 |  | H | H/H | N | 1.89 | 363 | | A |
| 106 | 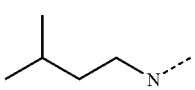 | H | H/H | N | 1.68 | 335 | | A |
| 107 | 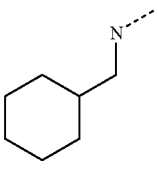 | H | H/H | N | 2.01 | 377 | | A |
| 108 |  | H | H/H | N | 2.09 | 403 | | A |
| 109 | 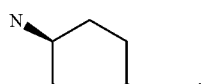 | H | H/H | N | 1.79 | 349 | | A |
| 110 | 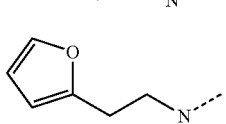 | H | H/H | N | 1.41 | 404 | | D |
| 111 |  | H | H/H | N | 1.88 | 401 | | A |

-continued
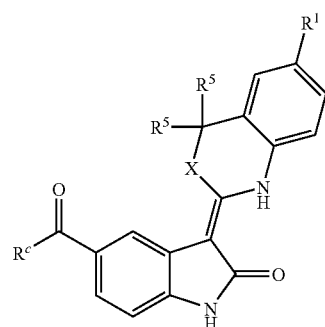
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 112 | N≡C-CH₂CH₂-N⋯ | H | H/H | N | 1.49 | 360 | 338 | C |
| 113 | 1,5-dimethylpyrazol-3-yl-CH₂-N⋯ | H | H/H | N | 1.53 | 415 | 342 | C |
| 114 | pyridin-2-yl-CH₂-N⋯ | H | H/H | N | 1.52 | 398 | 342 | C |
| 115 | pyridin-3-yl-CH₂-N⋯ | H | H/H | N | 1.5 | 398 | 338 | C |
| 116 | 1-cyanocyclopentyl-N⋯ | H | H/H | N | 1.65 | 400 | 342 | C |
| 117 | 6-amino-pyridin-3-yl-CH₂-N⋯ | H | H/H | N | 1.40 | 413 | 338 | C |
| 118 | 2-aminophenyl-CH₂-N⋯ | H | H/H | N | 1.54 | 412 | 342 | C |
| 119 | 4-aminophenyl-CH₂-N⋯ | H | H/H | N | 1.53 | 412 | 342 | C |

-continued

| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 120 | 3-pyridyl-CH₂-N< (meta) | H | H/H | N | 1.55 | 412 | 338 | C |
| 121 | cyclohexyl-N< | H | H/H | N | 1.71 | 389 | 342 | C |
| 122 | H₂N-CO-CH₂CH₂-N< | H | H/H | N | 1.40 | 378 | 338 | C |
| 123 | CH₃-O-CH₂CH₂CH₂-N< | H | H/H | N | 1.43 | 365 | 340 | C |
| 124 | (1-methyl-pyrazol-5-yl)-CH₂-N< | H | H/H | N | 1.49 | 401 | 342 | C |
| 125 | (pyrazol-3-yl)-CH₂-N< | H | H/H | N | 1.46 | 387 | 338 | C |
| 126 | (3,5-dimethyl-pyrazol-4-yl)-CH₂-N< | H | H/H | N | 1.47 | 415 | 338 | C |
| 127 | (furan-2-yl)-CH₂-N< | H | H/H | N | 1.62 | 387 | 342 | C |
| 128 | (furan-3-yl)-CH₂-N< | H | H/H | N | 1.61 | 387 | 342 | C |
| 129 | (pyridin-4-yl)-CH₂-N< | H | H/H | N | 1.49 | 398 | 338 | C |

-continued

| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 130 | methoxyethyl-N | H | H/H | N | 1.49 | 365 | 340 | C |
| 131 | 2-methyl-2-(N-methylcarbamoyl)-N | H | H/H | N | 1.37 | 392 | 338 | D |
| 132 | 2-(N-methylcarbamoyl)cyclohexyl-N | H | H/H | N | 1.46 | 432 | 338 | D |
| 133 | 3-methoxypropyl-N | H | H/H | N | 1.52 | 379 | 342 | C |
| 134 | (tetrahydrofuran-3-yl)methyl-N | H | H/H | N | 1.50 | 391 | 338 | C |
| 135 | (tetrahydrofuran-2-yl)methyl-N | H | H/H | N | 1.53 | 391 | 342 | C |
| 136 | cyanomethyl-N | H | H/H | N | 1.51 | 346 | 338 | C |
| 137 | pentan-2-yl-N | H | H/H | N | 1.73 | 377 | 342 | C |
| 138 | (1H-indazol-3-yl)methyl-N | H | H/H | N | 1.61 | 437 | 342 | C |
| 139 | (5-methylfuran-2-yl)methyl-N | H | H/H | N | 1.70 | 401 | 342 | C |

-continued

| Ex | Rc | R1 | R5/R5 | X | t_ret [min] | [M+H]+ | UV_max [nm] | HPLC |
|---|---|---|---|---|---|---|---|---|
| 140 | 3-(dimethylamino)benzyl-N | H | H/H | N | 1.96 | 440 | | B1 |
| 141 | 3-(methylamino)benzyl-N | H | H/H | N | 1.84 | 426 | | B1 |
| 142 | 3-hydroxybenzyl-N | H | H/H | N | 1.70 | 413 | | B1 |
| 143 | 2-(benzyloxy)ethyl-N | H | H/H | N | 1.94 | 441 | | B1 |
| 144 | benzyl-N | H | H/H | N | 1.89 | 397 | | B1 |
| 145 | 2-cyanopropan-2-yl-N | H | H/H | N | 1.57 | 374 | 342 | C |
| 146 | (5-bromobenzofuran-2-yl)methyl-N | H | H/H | N | 1.85 | 515 | 342 | C |

-continued
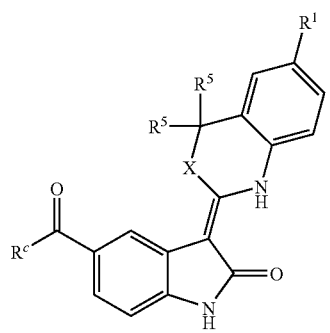
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 147 | 1-(pyridin-3-yl)ethylamino | H | H/H | N | 1.51 | 412 | 338 | C |
| 148 | 1-(pyridin-3-yl)ethylamino | H | H/H | N | 1.51 | 412 | 338 | C |
| 149 | (6-chloropyridin-3-yl)methylamino | H | H/H | N | 1.60 | 432 | 342 | C |
| 150 | (3-methylpyridin-4-yl)methylamino | H | H/H | N | 1.51 | 412 | 338 | C |
| 151 | (2-aminopyridin-4-yl)methylamino | H | H/H | N | 1.46 | 413 | 338 | C |
| 152 | 1-(pyridin-4-yl)propylamino | H | H/H | N | 1.58 | 426 | 342 | C |
| 153 | 1-(pyridin-2-yl)ethylamino | H | H/H | N | 1.60 | 412 | 338 | C |
| 154 | (5-methylpyridin-3-yl)methylamino | H | H/H | N | 1.55 | 412 | 340 | C |

-continued
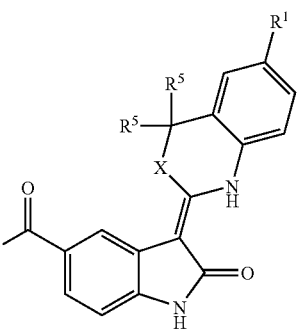
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 155 | 2-aminopyridin-3-ylmethyl-N | H | H/H | N | 1.52 | 413 | 338 | C |
| 156 | 4-aminopyridin-2-ylmethyl-N | H | H/H | N | 1.47 | 413 | 338 | C |
| 157 | 2-methylpyridin-4-ylmethyl-N | H | H/H | N | 1.52 | 412 | 342 | C |
| 158 | pyrimidin-2-ylmethyl-NH | H | H/H | N | 1.47 | 399 | 342 | C |
| 159 | 4-methylpyridin-2-ylmethyl-N | H | H/H | N | 1.60 | 412 | 338 | C |
| 160 | 2-phenylpropan-2-yl-N | H | H/H | N | 2.04 | 425 | | B1 |
| 161 | 3-methylbenzyl-N | H | H/H | N | 1.98 | 411 | | B1 |
| 162 | 4-methylbenzyl-N | H | H/H | N | 1.99 | 411 | | B1 |

-continued

| Ex | R^c | R^1 | R^5/R^5 | X | $t_{ret}$ [min] | $[M+H]^+$ | $UV_{max}$ [nm] | HPLC |
|---|---|---|---|---|---|---|---|---|
| 163 | (2-phenoxyethyl)amino | H | H/H | N | 1.95 | 427 | | B1 |
| 164 | (1-phenylethyl)amino | H | H/H | N | 1.97 | 411 | | B1 |
| 165 | (2-chlorobenzyl)amino | H | H/H | N | 2.00 | 431 | | B1 |
| 166 | (4-chlorobenzyl)amino | H | H/H | N | 2.02 | 431 | | B1 |
| 167 | (3-chlorobenzyl)amino | H | H/H | N | 2.02 | 431 | | B1 |
| 168 | (3-fluoropyridin-2-ylmethyl)amino | H | H/H | N | 1.70 | 416 | | B1 |
| 169 | (1-cyanocyclohexyl)amino | H | H/H | N | 1.92 | 414 | | B1 |
| 170 | (2-methoxy-2-methylpropyl)amino | H | H/H | N | 1.73 | 393 | | B1 |

-continued

| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 171 | 2-hydroxybenzyl-N | H | H/H | N | 1.86 | 413 | | B1 |
| 172 | ethoxyethyl-N | H | H/H | N | 1.68 | 379 | | B1 |
| 173 | 4-hydroxybenzyl-N | H | H/H | N | 1.66 | 413 | | B1 |
| 174 | methoxyisopropyl-N | H | H/H | N | 1.67 | 379 | | B1 |
| 175 | 2-methylbenzyl-N | H | H/H | N | 1.91 | 411 | | B1 |
| 176 | isopropoxyethyl-N | H | H/H | N | 1.69 | 393 | | B1 |
| 177 | 1-(3-pyridyl)ethyl-N | H | H/H | N | 1.64 | 426 | | B1 |
| 178 | (2-chloropyridin-4-yl)methyl-N | H | H/H | N | 1.56 | 432 | 342 | C |

-continued
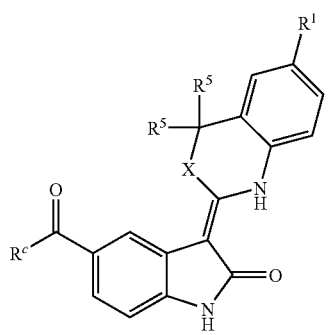
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 179 | phenyl-CH(CN)-N--- | H | H/H | N | 1.97 | 422 | | B1 |
| 180 | 3-cyano-4-chlorobenzyl-N--- | H | H/H | N | 1.90 | 446 | | B1 |
| 181 | 3-cyano-2-fluorobenzyl-N--- | H | H/H | N | 1.76 | 430 | | B1 |
| 182 | 3-cyano-2-methylbenzyl-N--- | H | H/H | N | 1.79 | 426 | | B1 |
| 183 | 2,6-dichlorobenzyl-N--- | H | H/H | N | 2.07 | 465 | | B1 |
| 184 | 2-chloro-6-methylbenzyl-N--- | H | H/H | N | 2.08 | 445 | | B1 |
| 185 | phenethyl-N--- | H | H/H | N | 1.96 | 411 | | B1 |
| 186 | 2-(pyridin-2-yl)ethyl-N--- | H | H/H | N | 1.65 | 412 | | B1 |

-continued
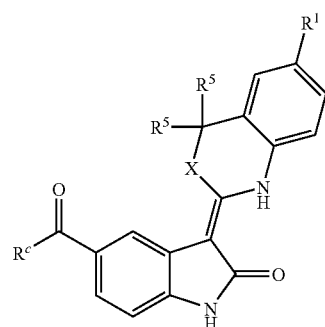
| Ex | $R^c$ | $R^1$ | $R^5/R^5$ | X | $t_{ret}$ [min] | $[M+H]^+$ | $UV_{max}$ [nm] | HPLC |
|---|---|---|---|---|---|---|---|---|
| 187 | 4-methoxyphenethyl-N | H | H/H | N | 1.71 | 441 | | C |
| 188 | 3,4-dimethoxyphenethyl-N | H | H/H | N | 1.82 | 471 | | B1 |
| 189 | 3-methoxyphenethyl-N | H | H/H | N | 1.98 | 441 | | B1 |
| 190 | pyridin-3-yl-ethyl-N | H | H/H | N | 1.63 | 412 | | B1 |
| 191 | pyridin-4-yl-ethyl-N | H | H/H | N | 1.64 | 412 | | B1 |
| 192 | pyridin-2-yl-methyl-N | H | H/H | N—iPr | 1.74 | 440 | | B1 |
| 193 | n-butyl-N | H | H/H | N—iPr | 1.94 | 405 | | B1 |
| 194 | pyridin-4-yl-methyl-N | H | H/H | N—iPr | 1.66 | 440 | | B1 |

-continued
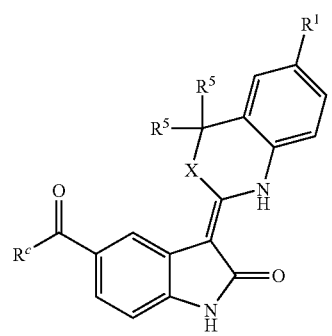
| Ex | R$^c$ | R$^1$ | R$^5$/R$^5$ | X | t$_{ret}$ [min] | [M + H]$^+$ | UV$_{max}$ [nm] | HPLC |
|---|---|---|---|---|---|---|---|---|
| 195 | pyridin-3-ylmethyl-N | H | H/H | N—iPr | 1.67 | 440 | | B1 |
| 196 | HN | H | H/H | N—iPr | 1.50 | 349 | | B1 |
| 197 | n-butyl-N | H | H/H | N—Me | 1.74 | 377 | | B1 |
| 198 | pyridin-2-ylmethyl-N | H | H/H | N—Me | 1.53 | 412 | | B1 |
| 199 | pyridin-4-ylmethyl-N | H | H/H | N—Me | 1.48 | 412 | | B1 |
| 200 | furan-2-ylmethyl-N | H | H/H | N—Me | 1.67 | 401 | | B1 |
| 201 | 2-methoxyethyl-N | H | H/H | N—Me | 1.46 | 379 | | B1 |

-continued
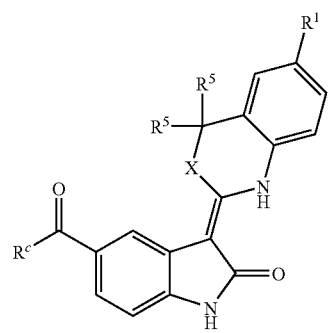
| Ex | $R^c$ | $R^1$ | $R^5/R^5$ | X | $t_{ret}$ [min] | $[M+H]^+$ | $UV_{max}$ [nm] | HPLC |
|---|---|---|---|---|---|---|---|---|
| 202 | 3-pyridylmethyl-N | H | H/H | N—Me | 1.58 | 426 | | B1 |
| 203 | 3-pyridylmethyl-N | H | Me/H | N | 1.65 | 412 | | B1 |
| 204 | Me2N(CH2)3-N | H | Me/H | N | 1.66 | 406 | | B1 |
| 205 | 2-pyridylmethyl-N | H | Me/H | N | 1.70 | 412 | | B1 |
| 206 | 4-pyridylmethyl-N | H | Me/H | N | 1.66 | 412 | | B1 |
| 207 | Me2N(CH2)2-N | H | Me/H | N | 1.70 | 392 | | B1 |
| 208 | Me-N | H | Me/H | N | 1.66 | 335 | | B1 |

-continued
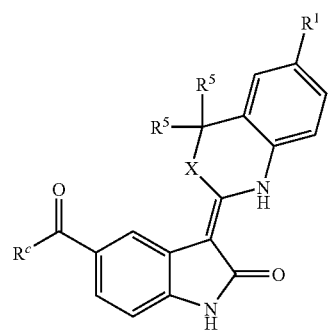
| Ex | $R^c$ | $R^1$ | $R^5/R^5$ | X | $t_{ret}$ [min] | $[M+H]^+$ | $UV_{max}$ [nm] | HPLC |
|---|---|---|---|---|---|---|---|---|
| 209 | cyclohexylmethyl-N | H | Me/H | N | 2.17 | 417 | | B1 |
| 210 | propyl-N | H | Me/H | N | 1.97 | 377 | | B1 |
| 211 | butyl-N-methyl | H | Me/Me | N | 1.96 | 391 | | B1 |
| 121 | N | H | Me/Me | N | 1.56 | 335 | | B1 |
| 213 | pyridin-2-ylmethyl-N | H | Me/Me | N | 1.78 | 426 | | B1 |
| 214 | pyridin-4-ylmethyl-N | H | Me/Me | N | 1.69 | 426 | | B1 |
| 215 | pyridin-3-ylmethyl-N | H | Me/Me | N | 1.73 | 426 | | B1 |
| 216 | (3-pyridylphenyl)methyl-N | H | Me/Me | N | 1.82 | 440 | | B1 |

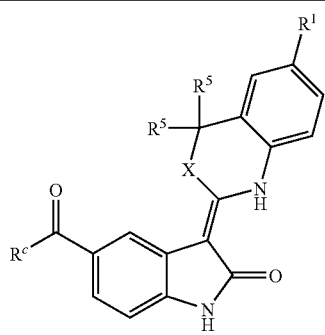

| Ex | $R^c$ | $R^1$ | $R^5/R^5$ | X | $t_{ret}$ [min] | $[M+H]^+$ | $UV_{max}$ [nm] | HPLC |
|---|---|---|---|---|---|---|---|---|
| 217 | (methylamino) | (methanesulfonamido) | H/H | N | 1.36 | 414 | | B1 |
| 218 | (butylamino) | (tert-butoxycarbonyl) | H/H | N | 1.43 | 477 | | B1 |

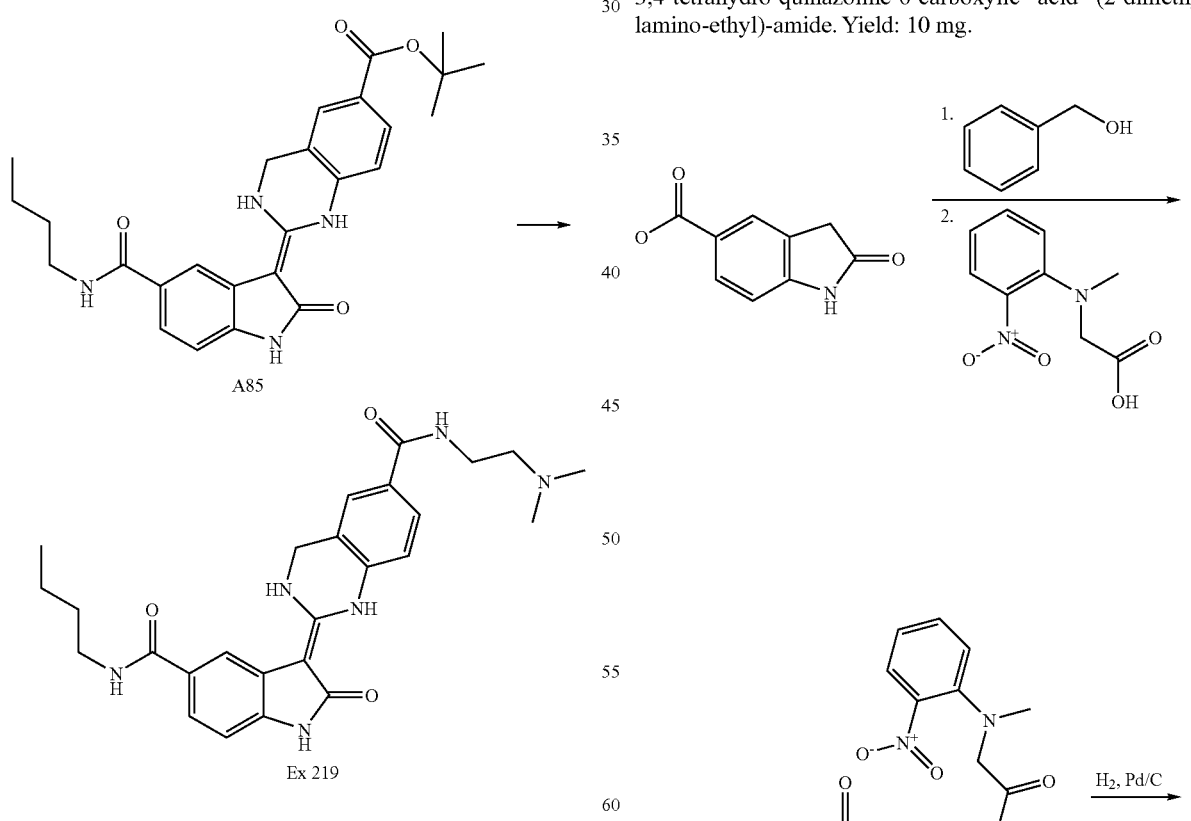

3,4-tetrahydro-quinazoline-6-carboxylic acid (2-dimethylamino-ethyl)-amide. Yield: 10 mg.

A85 (110 mg, 0.24 mmol) is dissolved in $CH_2Cl_2$ (7.5 mL), combined with TFA (3.8 mL) and stirred for 2 h at RT. After evaporation of the solvent and the TFA the free acid is reacted according to Method W with N,N-dimethylethylene-diamine (53 μL, 0.48 mmol) to obtain the desired compound 2-[5-butylcarbamoyl-2-oxo-1,2-dihydro-indol-(3Z)-ylidene]-1,2,

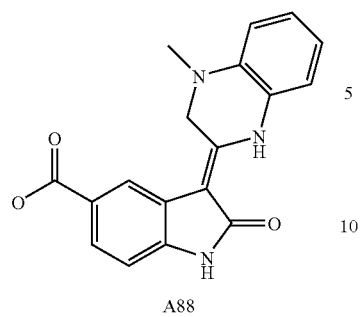

A88

2-Oxo-2,3-dihydro-1H-indole-5-carboxylic acid (7 g, 39 mmol) is dissolved together with benzylalcohol (4.2 mL, 39 mmol) and 4-N,N-dimethylaminopyridine (1 g, 7.9 mmol) in 70 mL DCM and cooled in the ice bath. Then 1-ethyl-3-(3-dimethylaminopropyl)carbodiimide (8.3 g, 43 mmol) is added and the mixture is heated to RT for 12 h. After evaporation of the solvent the residue is taken up in a little methanol and combined with 1 N hydrochloric acid (200 mL). The precipitate formed is filtered and dried. Yield: 6.9 g (65%) (A86).

The benzyl ester thus obtained (1.3 g, 4.7 mmol) is dissolved together with [methyl-(2-nitro-phenyl)-amino]-acetic acid (1.1 g, 5.2 mmol)—for synthesis see *Eur. J. Org. Chem.* 2003, 12, 2314-2326—and diisopropylethylamine (4.1 mL, 24 mmol) in dimethylformamide (10 mL), then combined with 2-(1H-7-azabenzotriazol-1-yl)-1,1,3,3-tetramethyl-uronium hexafluorophosphate (HATU, 2.1 g, 5.7 mmol) and stirred for 12 h at RT. After the addition of 10 mL ammonia in methanol the mixture is stirred for a further 6 h at RT, then mixed with water and extracted with DCM. The organic phase is dried and evaporated down. After purification by chromatography, the desired product benzyl 3-{2-[methyl-(2-nitrophenyl)-amino]-acetyl}-2-oxo-2,3-dihydro-1H-indole-5-carboxylate is obtained. Yield: 220 mg (10%) (A87).

A87 (190 mg, 0.41 mmol) is dissolved in methanol (30 mL), combined with palladium on activated charcoal (10%) and stirred for 12 h under hydrogen pressure (4 bar). After filtration and evaporation of the solvent, 3-[4-methyl-3,4-dihydro-1H-quinoxalin-(2Z)-ylidene]-2-oxo-2,3-dihydro-1H-indole-5-carboxylic acid is obtained.

Yield: 109 mg (82%) (A88).

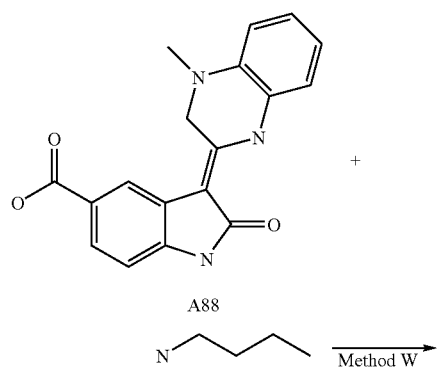

A88 + N⌢⌢⌢NH₂ →(Method W)

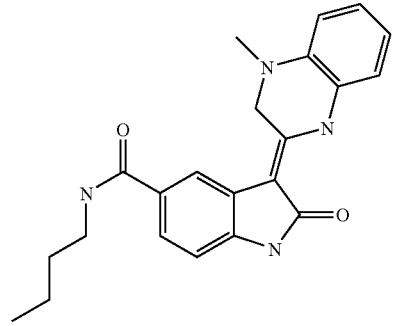

Ex. 220

A88 (54 mg, 0.17 mmol) is converted into the corresponding butylamide according to Method W.

Yield: 13 mg (20%). [M+1]⁺: 377; $R_t$ (Method B): 2.05 min; $UV_{max}$: 286 and 395 nm The corresponding anilines can be generated from A121 and A122 using hydrogen (analogously to Method L) and these are reacted analogously to Method W to form the acetamides.

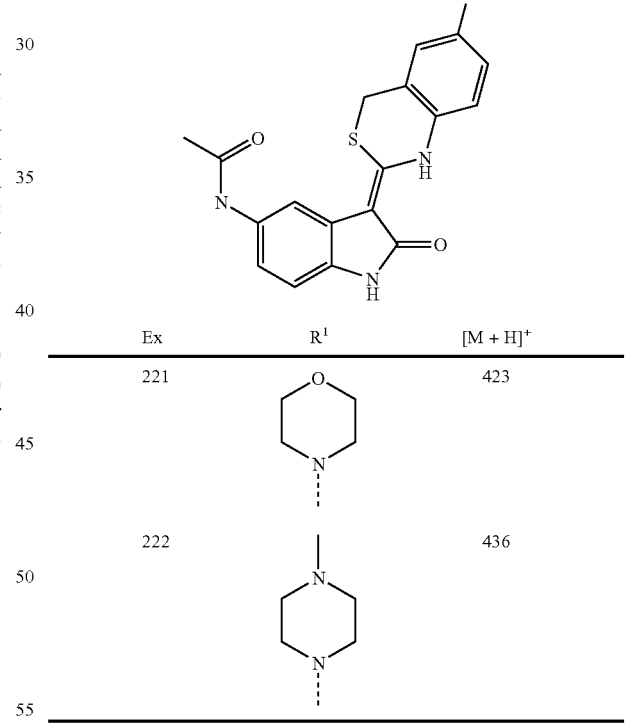

| Ex | R¹ | [M + H]⁺ |
|---|---|---|
| 221 | morpholine | 423 |
| 222 | 4-methylpiperazine | 436 |

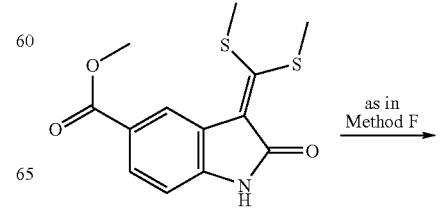

→ as in Method F

99
-continued

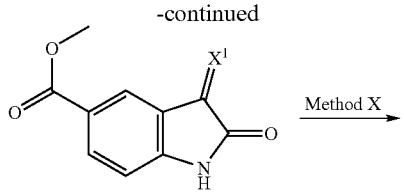

Method X →

100
-continued

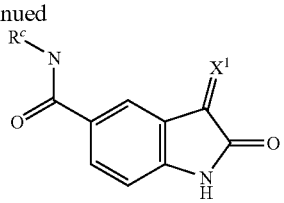

The following target molecules are prepared analogously to Method F, X and W.

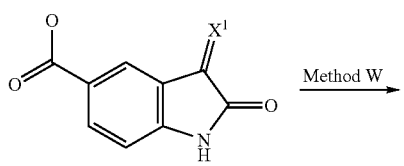

Method W →

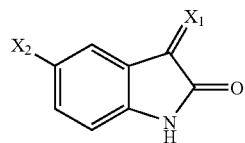

Examples 223-360

| Ex | R$_{X2}$ | R$_{X1}$ | t$_{ret}$ [min] | [M + H]$^+$ | HPLC Method |
|---|---|---|---|---|---|
| 223 | H$_3$C─\─\─N(H)─C(O)─X$_2$ | 1-methylpiperazinyl-tetrahydroquinazolin-2(1H)-one (X$_1$) | 1.76 | 475 | B1 |
| 224 | H$_3$C─\─\─N(H)─C(O)─X$_2$ | N-methyl-N-(1-methylpiperidin-4-yl)-tetrahydroquinazolin-2(1H)-one (X$_1$) | 1.86 | 486 | B1 |
| 225 | H$_3$C─\─\─N(H)─C(O)─X$_2$ | (tetrahydropyran-4-yl)amino-tetrahydroquinazolin-2(1H)-one (X$_1$) | 1.83 | 462 | B1 |

-continued
| Ex | R$_{X2}$ | R$_{X1}$ | t$_{ret}$ [min] | [M + H]$^+$ | HPLC Method |
|---|---|---|---|---|---|
| 226 | 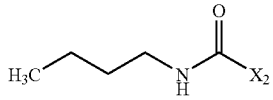 | 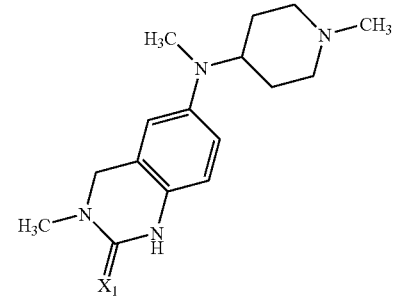 | 1.81 | 503 | B1 |
| 227 | 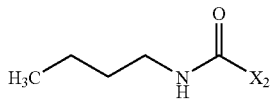 | 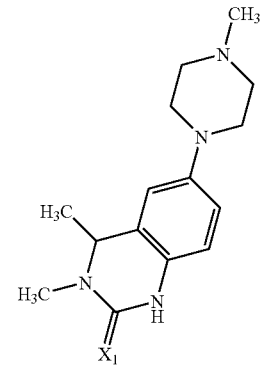 | 1.75 | 489 | B1 |
| 228 | 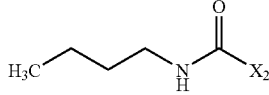 | 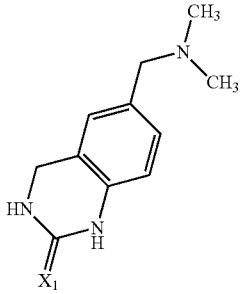 | 1.82 | 420 | B1 |
| 229 | 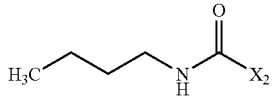 | 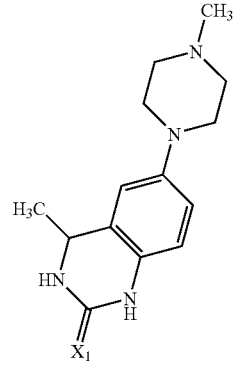 | 1.81 | 475 | B1 |

-continued

| Ex | R_{X2} | R_{X1} | t_{ret} [min] | [M + H]⁺ | HPLC Method |
|---|---|---|---|---|---|
| 230 | butyl-NH-C(=O)-X2 with CH3 | 4-methylpiperazinyl-substituted benzoxazinone | 1.80 | 462 | B1 |
| 231 | butyl-NH-C(=O)-X2 | benzoxazinone | 1.89 | 364 | B1 |
| 232 | butyl-NH-C(=O)-X2 | 3,4-dimethyl dihydroquinazolinone | 1.84 | 391 | B1 |
| 233 | butyl-NH-C(=O)-X2 | 5-fluoro-6-(4-methylpiperazinyl) tetrahydroquinazolinone | | 479 | B1 |
| 234 | butyl-NH-C(=O)-X2 | 7-fluoro-6-(4-methylpiperazinyl) tetrahydroquinazolinone | 1.84 | 479 | B1 |

-continued

| Ex | R$_{X2}$ | R$_{X1}$ | t$_{ret}$ [min] | [M + H]$^+$ | HPLC Method |
|---|---|---|---|---|---|
| 235 | H₃C-CH₂-CH₂-CH₂-NH-C(=O)-X₂ | (1-methylpiperidin-4-yl)(methyl)amino-substituted tetrahydroquinazolinone | 1.95 | 489 | B1 |
| 236 | H₃C-CH₂-CH₂-CH₂-NH-C(=O)-X₂ | morpholino-substituted methyl dihydroquinazolinone | 1.87 | 462 | B1 |
| 237 | CH₃-CH₂-CH₂-NH-C(=O)-X₂ | morpholino-substituted methyl benzoxazinone | 1.94 | 463 | B1 |
| 238 | CH₃-CH₂-CH₂-NH-C(=O)-X₂ | (4-methylpiperazin-1-yl)-substituted methyl benzoxazinone | 1.87 | 476 | B1 |

| Ex | R_{X2} | R_{X1} | t_{ret} [min] | [M + H]⁺ | HPLC Method |
|---|---|---|---|---|---|
| 239 | 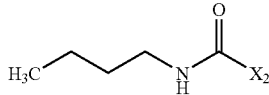 | 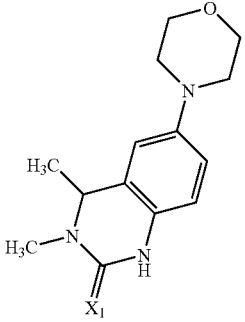 | 1.79 | 476 | B1 |
| 240 | 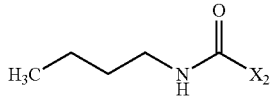 | 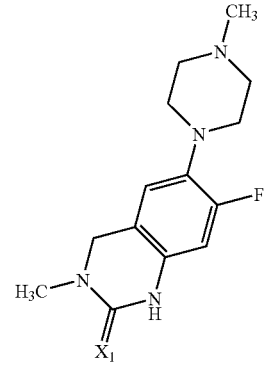 | 1.75 | 493 | B1 |
| 241 | 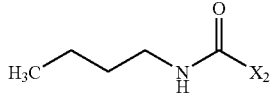 | 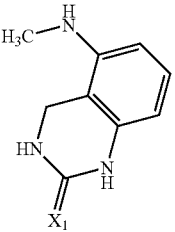 | 1.89 | 392 | B1 |
| 242 | 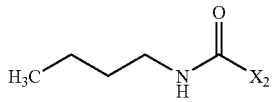 | 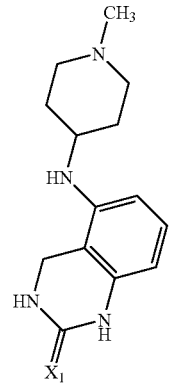 | 1.93 | 475 | B1 |

| Ex | R$_{X2}$ | R$_{X1}$ | t$_{ret}$ [min] | [M + H]$^+$ | HPLC Method |
|---|---|---|---|---|---|
| 243 | 4,4,4-trifluorobutyl-NH-C(O)-X$_2$ | 6-(4-methylpiperazin-1-yl)-3-methyl-2-X$_1$-1,2,3,4-tetrahydroquinazoline | 1.74 | 529 | B1 |
| 244 | 4,4,4-trifluorobutyl-NH-C(O)-X$_2$ | 6-(4-methylpiperazin-1-yl)-2-X$_1$-1,2,3,4-tetrahydroquinazoline | 1.80 | 515 | B1 |
| 245 | 4,4,4-trifluorobutyl-NH-C(O)-X$_2$ | 6-morpholino-3-methyl-2-X$_1$-1,2,3,4-tetrahydroquinazoline | 1.77 | 516 | B1 |
| 246 | 4,4,4-trifluorobutyl-NH-C(O)-X$_2$ | 6-(4-methylpiperazin-1-yl)-3-methyl-4-methyl-2-X$_1$-1,2,3,4-tetrahydroquinazoline | 1.79 | 543 | B1 |

-continued
| Ex | R$_{X2}$ | R$_{X1}$ | t$_{ret}$ [min] | [M + H]$^+$ | HPLC Method |
|---|---|---|---|---|---|
| 247 | 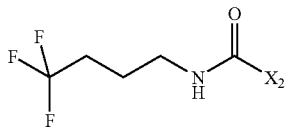 | 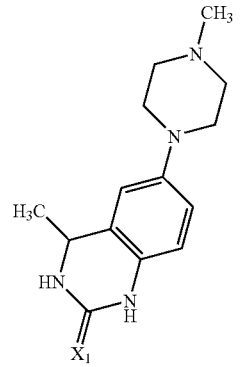 | 1.85 | 529 | B1 |
| 248 | 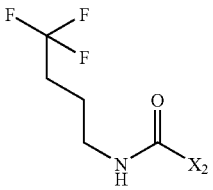 | 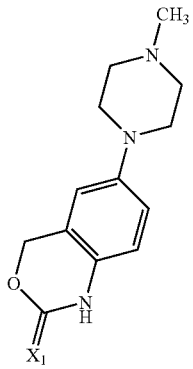 | 1.84 | 516 | B1 |
| 249 | 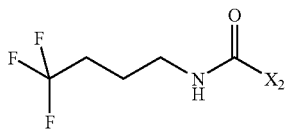 | 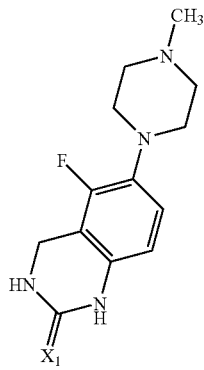 | 1.87 | 553 | B1 |
| 250 | 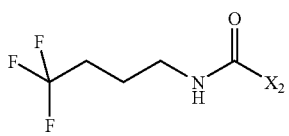 | 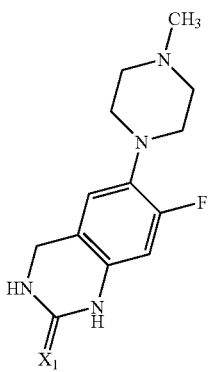 | 1.86 | 533 | B1 |

-continued

| Ex | R_{X2} | R_{X1} | t_{ret} [min] | [M + H]⁺ | HPLC Method |
|---|---|---|---|---|---|
| 251 | 3,3,3-trifluoropropyl-NH-C(O)-X₂ | 6-(4-methylpiperazin-1-yl)-3-methyl-3,4-dihydroquinazolin-2(1H)-X₁ | 1.67 | 515 | B1 |
| 252 | 3,3,3-trifluoropropyl-NH-C(O)-X₂ | 6-(4-methylpiperazin-1-yl)-3,4-dihydroquinazolin-2(1H)-X₁ | 1.74 | 501 | B1 |
| 253 | 3,3,3-trifluoropropyl-NH-C(O)-X₂ | 6-morpholino-3-methyl-3,4-dihydroquinazolin-2(1H)-X₁ |  | 502 | B1 |
| 254 | 3,3,3-trifluoropropyl-NH-C(O)-X₂ | 6-(4-methylpiperazin-1-yl)-3,4-dimethyl-3,4-dihydroquinazolin-2(1H)-X₁ | 1.73 | 529 | B1 |

-continued

| Ex | R_{X2} | R_{X1} | t_{ret} [min] | [M + H]+ | HPLC Method |
|---|---|---|---|---|---|
| 255 | 3,3,3-trifluoropropyl-NH-C(O)-X2 | 4-methylpiperazinyl-phenyl fused to HN-C(=X1)-NH ring with CH(CH3) | 1.79 | 515 | B1 |
| 256 | 3,3,3-trifluoropropyl-NH-C(O)-X2 | 4-methylpiperazinyl-phenyl fused to O-C(=X1)-NH ring | 1.78 | 502 | B1 |
| 257 | isopentyl-NH-C(O)-X2 | 4-methylpiperazinyl-phenyl fused to N(CH3)-C(=X1)-NH ring | 1.79 | 489 | B1 |
| 258 | isopentyl-NH-C(O)-X2 | 4-methylpiperazinyl-phenyl fused to HN-C(=X1)-NH ring | 1.85 | 475 | B1 |

-continued

| Ex | R$_{X2}$ | R$_{X1}$ | t$_{ret}$ [min] | [M + H]$^+$ | HPLC Method |
|---|---|---|---|---|---|
| 259 | H$_3$C-CH(CH$_3$)-CH$_2$-CH$_2$-NH-C(O)-X$_2$ | morpholine-substituted N-methyl tetrahydroquinazolinone with X$_1$ | 1.83 | 476 | B1 |
| 260 | H$_3$C-CH(CH$_3$)-CH$_2$-CH$_2$-NH-C(O)-X$_2$ | 4-methylpiperazine-substituted 3,4-dimethyl dihydroquinazolinone with X$_1$ | 1.84 | 503 | B1 |
| 261 | H$_3$C-CH(CH$_3$)-CH$_2$-CH$_2$-NH-C(O)-X$_2$ | 4-methylpiperazine-substituted benzoxazinone with X$_1$ | 1.89 | 476 | B1 |
| 262 | H$_3$C-CH(CH$_3$)-CH$_2$-CH$_2$-NH-C(O)-X$_2$ | 4-methylpiperazine, fluoro-substituted dihydroquinazolinone with X$_1$ | 1.97 | 493 | B1 |

-continued

| Ex | R$_{X2}$ | R$_{X1}$ | t$_{ret}$ [min] | [M + H]$^+$ | HPLC Method |
|---|---|---|---|---|---|
| 263 | H$_3$C–CH(CH$_3$)–CH$_2$–CH$_2$–NH–C(=O)–X$_2$ | 4-methylpiperazinyl-substituted fluoro-tetrahydroquinazoline-2(X$_1$) | 1.91 | 493 | B1 |
| 264 | H$_3$C–CH(CH$_3$)–CH$_2$–CH$_2$–NH–C(=O)–X$_2$ | N-methyl-N-(1-methylpiperidin-4-yl)amino-tetrahydroquinazoline-2(X$_1$) | 2.04 | 503 | B1 |
| 265 | H$_3$C–CH(CH$_3$)–CH$_2$–CH$_2$–NH–C(=O)–X$_2$ | 4-(2,2,2-trifluoroethyl)piperazinyl-substituted N3-methyl-tetrahydroquinazoline-2(X$_1$) | 2.13 | 557 | B1 |
| 266 | H$_3$C–CH(CH$_3$)–CH$_2$–CH$_2$–NH–C(=O)–X$_2$ | N,N-dimethylamino-tetrahydroquinazoline-2(X$_1$) | 2.06 | 420 | B1 |

-continued

| Ex | $R_{X2}$ | $R_{X1}$ | $t_{ret}$ [min] | $[M+H]^+$ | HPLC Method |
|---|---|---|---|---|---|
| 267 | H-NH-C(O)-X₂ | N-methylpiperidinyl-N(CH₃)- substituted dihydroquinazolinone | 1.53 | 433 | B1 |
| 268 | H-NH-C(O)-X₂ | tetrahydropyranyl-NH- substituted dihydroquinazolinone | 1.46 | 406 | B1 |
| 269 | H₂N-C(O)-X₂ | 4-methylpiperazinyl-substituted N,4-dimethyl dihydroquinazolinone | 1.37 | 433 | B1 |
| 270 | H₂N-C(O)-X₂ | N-methyl dihydroquinazolinone | 1.25 | 321 | B1 |
| 271 | H₂N-C(O)-X₂ | benzoxazinone | 1.45 | 308 | B1 |

-continued
| Ex | R$_{X2}$ | R$_{X1}$ | t$_{ret}$ [min] | [M + H]$^+$ | HPLC Method |
|---|---|---|---|---|---|
| 272 |  | 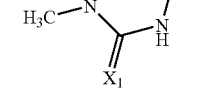 | 1.39 | 335 | B1 |
| 273 | 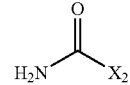 | 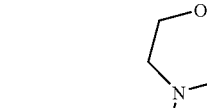 | 1.49 | 406 | B1 |
| 274 |  | 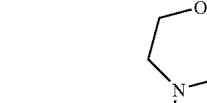 | 1.52 | 407 | B1 |
| 275 |  |  | 1.45 | 420 | B1 |
| 276 |  | 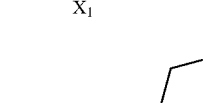 | 1.36 | 420 | B1 |

-continued

| Ex | R_{X2} | R_{X1} | t_{ret} [min] | [M + H]^+ | HPLC Method |
|---|---|---|---|---|---|
| 277 | (1-methylpiperidin-3-yl)NH-C(=O)-X_2 | 7-(4-methylpiperazin-1-yl)-3-methyl-2-X_1-1,2,3,4-tetrahydroquinazoline | 1.58 | 516 | B1 |
| 278 | (1-methylpiperidin-3-yl)NH-C(=O)-X_2 | 7-(4-methylpiperazin-1-yl)-2-X_1-1,2,3,4-tetrahydroquinazoline | 1.65 | 502 | B1 |
| 279 | (1-methylpiperidin-3-yl)NH-C(=O)-X_2 | 4,4-dimethyl-2-X_1-1,2,3,4-tetrahydroquinazoline | 1.85 | 432 | B1 |
| 280 | (1-methylpiperidin-3-yl)NH-C(=O)-X_2 | 7-morpholino-2-X_1-1,2,3,4-tetrahydroquinazoline | 1.65 | 489 | B1 |

-continued
| Ex | R$_{X2}$ | R$_{X1}$ | t$_{ret}$ [min] | [M + H]$^+$ | HPLC Method |
|---|---|---|---|---|---|
| 281 | 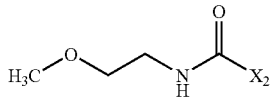 | 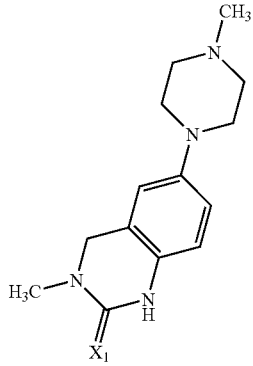 | 1.49 | 477 | B1 |
| 282 | 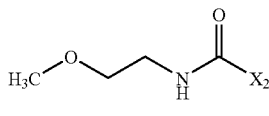 |  | 1.75 | 393 | B1 |
| 283 | 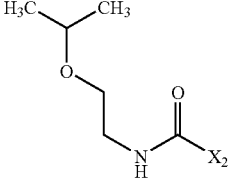 | 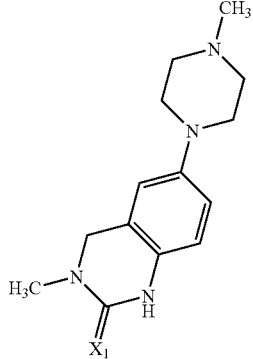 | 1.64 | 505 | B1 |
| 284 | 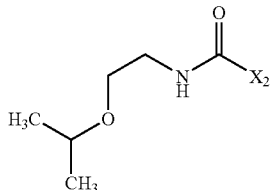 | 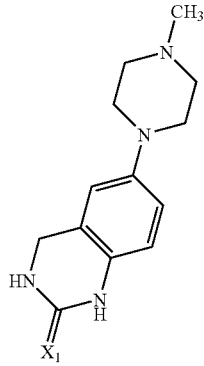 | 1.73 | 491 | B1 |
| 285 | 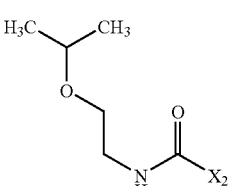 | 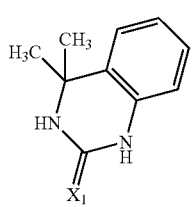 | 1.93 | 421 | B1 |

-continued
| Ex | R$_{X2}$ | R$_{X1}$ | t$_{ret}$ [min] | [M + H]$^+$ | HPLC Method |
|---|---|---|---|---|---|
| 286 | 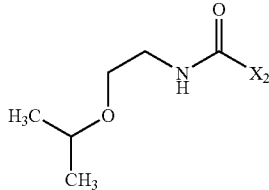 | 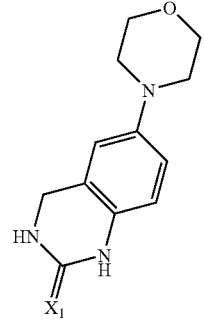 | 1.74 | 478 | B1 |
| 287 | 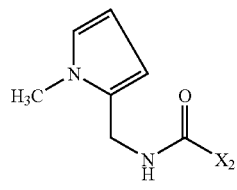 | 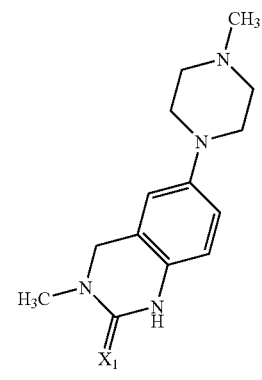 | 1.67 | 512 | B1 |
| 288 | 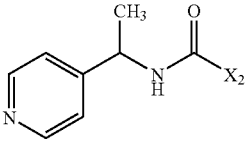 | 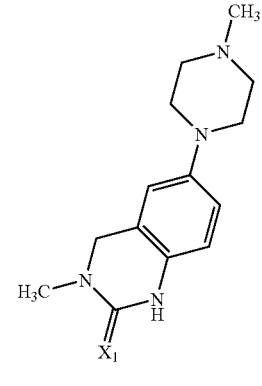 | 1.59 | 524 | B1 |
| 289 | 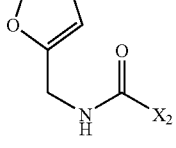 | 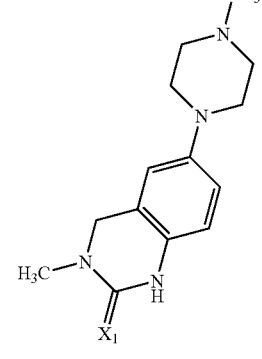 | 1.69 | 499 | B1 |

-continued
| Ex | R<sub>X2</sub> | R<sub>X1</sub> | t<sub>ret</sub> [min] | [M + H]⁺ | HPLC Method |
|---|---|---|---|---|---|
| 290 | 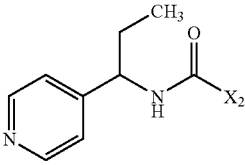 | 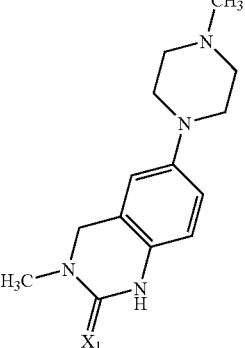 | 1.62 | 538 | B1 |
| 291 | 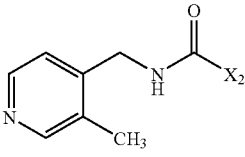 | 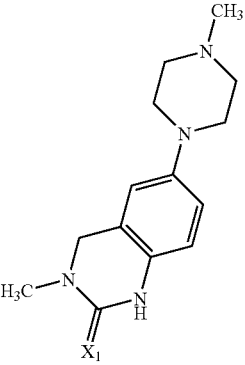 | 1.59 | 524 | B1 |
| 292 | 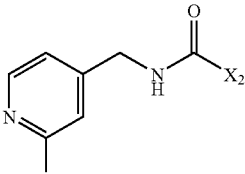 | 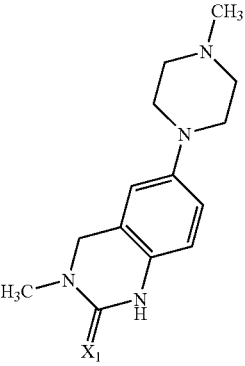 | 1.48 | 525 | B1 |
| 293 | 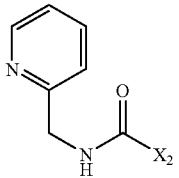 | 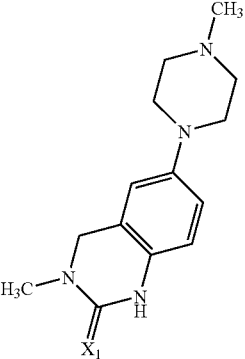 | 1.59 | 510 | B1 |

-continued
| Ex | R_{X2} | R_{X1} | t_{ret} [min] | [M + H]+ | HPLC Method |
|---|---|---|---|---|---|
| 294 |  |  | 1.67 | 502 | B1 |
| 295 |  | 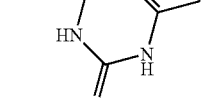 | 1.62 | 524 | B1 |
| 296 | 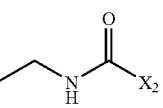 |  | 1.56 | 491 | B1 |
| 297 |  |  | 1.6 | 488 | B1 |

-continued

| Ex | R$_{X2}$ | R$_{X1}$ | t$_{ret}$ [min] | [M + H]$^+$ | HPLC Method |
|---|---|---|---|---|---|
| 298 | | | 1.61 | 524 | B1 |
| 299 | | | 1.73 | 487 | B1 |
| 300 | | | 1.53 | 516 | B1 |
| 301 | | | 1.93 | 601 | B1 |

-continued

| Ex | R$_{X2}$ | R$_{X1}$ | t$_{ret}$ [min] | [M + H]$^+$ | HPLC Method |
|---|---|---|---|---|---|
| 302 | quinuclidinyl-NH-C(O)-X$_2$ | 4-methylpiperazinyl-tetrahydroquinazolinone (X$_1$) | 1.63 | 514 | B1 |
| 303 | pyridin-4-yl-CH$_2$-NH-C(O)-X$_2$ | N-methyl-4-methylpiperazinyl-tetrahydroquinazolinone (X$_1$) | 1.54 | 510 | B1 |
| 304 | H$_3$C-O-(CH$_2$)$_3$-NH-C(O)-X$_2$ | N-methyl-4-methylpiperazinyl-tetrahydroquinazolinone (X$_1$) | 1.56 | 491 | B1 |
| 305 | 5-methylfuran-2-yl-CH$_2$-NH-C(O)-X$_2$ | N-methyl-4-methylpiperazinyl-tetrahydroquinazolinone (X$_1$) | 1.74 | 513 | B1 |

-continued
| Ex | R$_{X2}$ | R$_{X1}$ | t$_{ret}$ [min] | [M + H]$^+$ | HPLC Method |
|---|---|---|---|---|---|
| 306 | 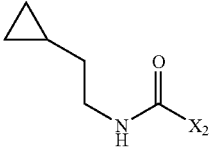 | 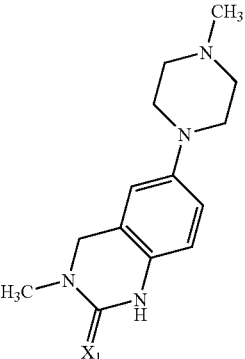 | 1.70 | 487 | B1 |
| 307 | 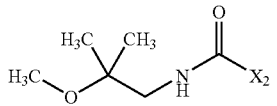 | 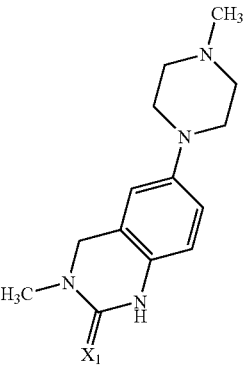 | 1.60 | 505 | B1 |
| 308 | 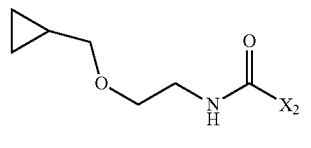 | 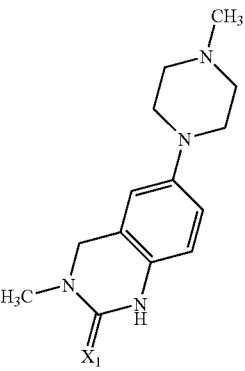 | 1.64 | 517 | B1 |
| 309 | 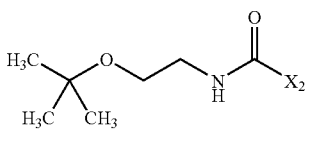 | 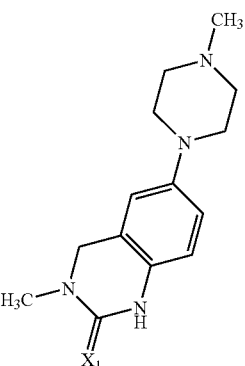 | 1.68 | 519 | B1 |

-continued

| Ex | R_{X2} | R_{X1} | t_{ret} [min] | [M + H]⁺ | HPLC Method |
|---|---|---|---|---|---|
| 310 | | | 1.55 | 510 | B1 |
| 311 | | | 1.77 | 489 | B1 |
| 312 | | | 1.78 | 489 | B1 |
| 313 | | | 1.73 | 533 | B1 |

-continued

| Ex | R$_{X2}$ | R$_{X1}$ | t$_{ret}$ [min] | [M + H]$^+$ | HPLC Method |
|---|---|---|---|---|---|
| 314 | 3-fluoropyridin-2-yl-methyl-NH-C(O)-X$_2$ | 6-(4-methylpiperazin-1-yl)-3-methyl-3,4-dihydroquinazolin-2(1H)-X$_1$ | 1.60 | 528 | B1 |
| 315 | 1-methoxypropan-2-yl-NH-C(O)-X$_2$ | 6-(4-methylpiperazin-1-yl)-3,4-dihydroquinazolin-2(1H)-X$_1$ | 1.64 | 477 | B1 |
| 316 | 2,2,3,3,3-pentafluoropropyl-NH-C(O)-X$_2$ | 6-(4-methylpiperazin-1-yl)-3-methyl-3,4-dihydroquinazolin-2(1H)-X$_1$ | 1.79 | 551 | B1 |
| 317 | 2,2,2-trifluoroethyl-NH-C(O)-X$_2$ | 6-(4-methylpiperazin-1-yl)-3-methyl-3,4-dihydroquinazolin-2(1H)-X$_1$ | 1.65 | 501 | B1 |

-continued

| Ex | R_{X2} | R_{X1} | t_{ret} [min] | [M + H]⁺ | HPLC Method |
|---|---|---|---|---|---|
| 318 | cyclopropylmethyl-NH-C(=O)-X₂ | 7-(4-methylpiperazin-1-yl)-3-methyl-2-X₁-1,2,3,4-tetrahydroquinazolin | 1.61 | 473 | B1 |
| 319 | H₃C-CH₂-CH₂-O-CH₂-CH₂-CH₂-NH-C(=O)-X₂ | 7-(4-methylpiperazin-1-yl)-3-methyl-2-X₁-1,2,3,4-tetrahydroquinazolin | 1.69 | 519 | B1 |
| 320 | cyclopropyl-CH₂-CH₂-CH₂-NH-C(=O)-X₂ | 7-(4-methylpiperazin-1-yl)-3-methyl-2-X₁-1,2,3,4-tetrahydroquinazolin | 1.80 | 501 | B1 |
| 321 | (H₃C)₂CH-O-CH₂-CH₂-CH₂-NH-C(=O)-X₂ | 7-(4-methylpiperazin-1-yl)-3-methyl-2-X₁-1,2,3,4-tetrahydroquinazolin | 1.66 | 519 | B1 |

-continued

| Ex | R_{X2} | R_{X1} | t_{ret} [min] | [M + H]⁺ | HPLC Method |
|---|---|---|---|---|---|
| 322 | ethyl-NH-C(O)-X2 | 4-(4-methylpiperazin-1-yl)-3-methyl-3,4-dihydroquinazolin-2(1H)-X1 | 1.49 | 447 | B1 |
| 323 | isopentyl-NH-C(O)-X2 | 4-(4-methylpiperazin-1-yl)-3-methyl-3,4-dihydroquinazolin-2(1H)-X1 | 1.90 | 503 | B1 |
| 324 | cyclopropyl-NH-C(O)-X2 | 4-(4-methylpiperazin-1-yl)-3-methyl-3,4-dihydroquinazolin-2(1H)-X1 | 1.51 | 459 | B1 |
| 325 | (5-cyanofuran-2-yl)methyl-NH-C(O)-X2 | 4-(4-methylpiperazin-1-yl)-3,4-dihydroquinazolin-2(1H)-X1 | 1.77 | 510 | B1 |

-continued

| Ex | R$_{X2}$ | R$_{X1}$ | t$_{ret}$ [min] | [M + H]$^+$ | HPLC Method |
|---|---|---|---|---|---|
| 326 | H₃C-CH₂-CH₂-NH-C(=O)-X₂ | 6-(4-methylpiperazin-1-yl)-3-methyl-3,4-dihydroquinazolin-2(1H)-one with X₁ | 1.58 | 461 | B1 |
| 327 | H₃C-O-CH₂-CH₂-CH₂-NH-C(=O)-X₂ | 6-(4-methylpiperazin-1-yl)-3-methyl-3,4-dihydroquinazolin-2(1H)-one with X₁ | 1.6 | 505 | B1 |
| 328 | (2-methylpyridin-4-yl)methyl-NH-C(=O)-X₂ | 6-(4-methylpiperazin-1-yl)-3,4-dihydroquinazolin-2(1H)-one with X₁ | 1.60 | 510 | B1 |
| 329 | 2-(pyridin-4-yl)ethyl-NH-C(=O)-X₂ | 6-(4-methylpiperazin-1-yl)-3,4-dihydroquinazolin-2(1H)-one with X₁ | 1.64 | 510 | B1 |

| Ex | R$_{X2}$ | R$_{X1}$ | t$_{ret}$ [min] | [M + H]$^+$ | HPLC Method |
|---|---|---|---|---|---|
| 330 | isobutyl-NH-C(O)-X$_2$ | 4-methylpiperazinyl-phenyl-CH$_2$-N(CH$_3$)-C(X$_1$)-NH- | 1.68 | 475 | B1 |
| 331 | pyridin-3-yl-ethyl-NH-C(O)-X$_2$ | 4-methylpiperazinyl-phenyl-CH$_2$-NH-C(X$_1$)-NH- | 1.63 | 510 | B1 |
| 332 | cyclobutylmethyl-NH-C(O)-X$_2$ | 4-methylpiperazinyl-phenyl-CH$_2$-N(CH$_3$)-C(X$_1$)-NH- | 1.72 | 487 | B1 |
| 333 | n-pentyl-NH-C(O)-X$_2$ | 4-methylpiperazinyl-phenyl-CH$_2$-N(CH$_3$)-C(X$_1$)-NH- | 1.80 | 489 | B1 |

-continued

| Ex | R$_{X2}$ | R$_{X1}$ | t$_{ret}$ [min] | [M + H]$^+$ | HPLC Method |
|---|---|---|---|---|---|
| 334 | 2-(pyridin-2-yl)ethyl-NH-C(=O)-X$_2$ | 7-(4-methylpiperazin-1-yl)-3,4-dihydroquinazoline-2(1H)-X$_1$ | 1.66 | 510 | B1 |
| 335 | cyclohexylmethyl-NH-C(=O)-X$_2$ | 7-(4-methylpiperazin-1-yl)-3-methyl-3,4-dihydroquinazoline-2(1H)-X$_1$ | 1.88 | 515 | B1 |
| 336 | cyclopentylmethyl-NH-C(=O)-X$_2$ | 7-(4-methylpiperazin-1-yl)-3-methyl-3,4-dihydroquinazoline-2(1H)-X$_1$ | 1.8 | 501 | B1 |
| 337 | propargyl-NH-C(=O)-X$_2$ | 7-(4-methylpiperazin-1-yl)-3-methyl-3,4-dihydroquinazoline-2(1H)-X$_1$ | 1.51 | 457 | B1 |

-continued

| Ex | R$_{X2}$ | R$_{X1}$ | t$_{ret}$ [min] | [M + H]$^+$ | HPLC Method |
|---|---|---|---|---|---|
| 338 | HC≡C-CH$_2$CH$_2$-NH-C(=O)-X$_2$ | 6-(4-methylpiperazin-1-yl)-3-methyl-2-(X$_1$)-1,2,3,4-tetrahydroquinazolin-7-yl | 1.56 | 471 | B1 |
| 339 | cyclobutyl-NH-C(=O)-X$_2$ | 6-(4-methylpiperazin-1-yl)-3-methyl-2-(X$_1$)-1,2,3,4-tetrahydroquinazolin-7-yl | 1.63 | 473 | B1 |
| 340 | F-CH$_2$CH$_2$CH$_2$-NH-C(=O)-X$_2$ | 6-(4-methylpiperazin-1-yl)-3-methyl-2-(X$_1$)-1,2,3,4-tetrahydroquinazolin-7-yl | 1.53 | 479 | B1 |
| 341 | PhCH$_2$-NH-C(=O)-X$_2$ | 6-(4-methylpiperazin-1-yl)-3-methyl-2-(X$_1$)-1,2,3,4-tetrahydroquinazolin-7-yl | 1.76 | 509 | B1 |

-continued

| Ex | R$_{X2}$ | R$_{X1}$ | t$_{ret}$ [min] | [M + H]$^+$ | HPLC Method |
|---|---|---|---|---|---|
| 342 | cyclopentyl-CH$_2$CH$_2$-NH-C(=O)-X$_2$ | 4-methylpiperazinyl-substituted tetrahydroquinazolinone-X$_1$ | 1.91 | 515 | B1 |
| 343 | cyclohexyl-CH$_2$CH$_2$-NH-C(=O)-X$_2$ | 4-methylpiperazinyl-substituted tetrahydroquinazolinone-X$_1$ | 2.00 | 529 | B1 |
| 344 | CF$_3$-CH(OH)-CH$_2$-NH-C(=O)-X$_2$ | 4-methylpiperazinyl-substituted tetrahydroquinazolinone-X$_1$ | 1.57 | 531 | B1 |
| 345 | (tetrahydropyran-4-yl)-CH$_2$CH$_2$-NH-C(=O)-X$_2$ | 4-methylpiperazinyl-substituted tetrahydroquinazolinone-X$_1$ | 1.57 | 531 | B1 |

-continued

| Ex | R<sub>X2</sub> | R<sub>X1</sub> | t<sub>ret</sub> [min] | [M + H]⁺ | HPLC Method |
|---|---|---|---|---|---|
| 346 | (2-chloropyridin-4-yl)methyl-NH-C(=O)-X₂ | 4-methylpiperazinyl-phenyl fused dihydropyrimidine-X₁ | 1.69 | 530 | B1 |
| 347 | isohexyl-NH-C(=O)-X₂ | 4-methylpiperazinyl-phenyl fused dihydrothiazine-X₁ | 2.11 | 506 | B1 |
| 348 | cyclohexylmethyl-NH-C(=O)-X₂ | 4-methylpiperazinyl-phenyl fused dihydrothiazine-X₁ | 2.12 | 518 | B1 |
| 349 | n-butyl-NH-C(=O)-X₂ | 4-methylpiperazinyl-phenyl fused dihydrothiazine-X₁ | 1.92 | 478 | B1 |

| Ex | R$_{X2}$ | R$_{X1}$ | t$_{ret}$ [min] | [M + H]$^+$ | HPLC Method |
|---|---|---|---|---|---|
| 350 | 3-methylbutyl-NH-C(=O)-X$_2$ | 4-(morpholin-4-yl)-1-methyl-substituted 2-thioxo-1,2,3,4-tetrahydroquinazoline | 2.09 | 493 | B1 |
| 351 | 4,4,4-trifluorobutyl-NH-C(=O)-X$_2$ | 6-(4-methylpiperazin-1-yl)-2-thioxo-1,2,3,4-tetrahydro-benzo[d][1,3]thiazine | 1.94 | 532 | B1 |
| 352 | 3-methylbutyl-NH-C(=O)-X$_2$ | 6-(4-methylpiperazin-1-yl)-2-thioxo-1,2,3,4-tetrahydro-benzo[d][1,3]thiazine | 1.99 | 492 | B1 |
| 353 | 4,4,4-trifluorobutyl-NH-C(=O)-X$_2$ | 6-(morpholin-4-yl)-2-thioxo-1,2,3,4-tetrahydro-benzo[d][1,3]thiazine | 1.98 | 519 | B1 |

-continued

| Ex | R<sub>X2</sub> | R<sub>X1</sub> | t<sub>ret</sub> [min] | [M + H]<sup>+</sup> | HPLC Method |
|---|---|---|---|---|---|
| 354 | | | 1.92 | 395 | B1 |
| 355 | | | | 516 | B1 |
| 356 | | | 1.65 | 503 | B1 |
| 357 | | | 1.81 | 502 | B1 |
| 358 | | | | 588 | B1 |

-continued

| Ex | $R_{X2}$ | $R_{X1}$ | $t_{ret}$ [min] | $[M+H]^+$ | HPLC Method |
|---|---|---|---|---|---|
| 359 | | | 1.93 | 476 | B1 |
| 360 | | | 1.83 | 462 | B1 |

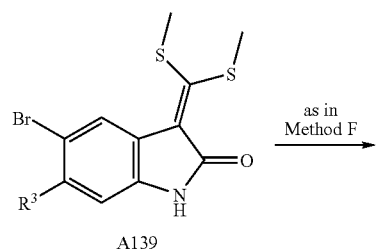

A139 as in Method F →

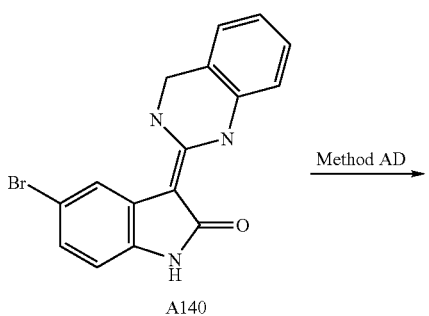

A140 Method AD →

Method AD

Under an argon atmosphere, A140 (60 mg), 3-pyridylboric acid (36 mg) and 1,1'-bis(diphenylphosphino)-ferrocene-palladium(II)dichloride (8 mg) are combined with 720 μL of a mixture of THF/NMP (2:1) and with caesium carbonate (75 mg) which has been dissolved in 100 μL water. The reaction mixture is stirred for 1 h at 100° C. in a Biotage microwave. The crude product thus obtained (Example 361) is purified by RP-HPLC.

$t_{ret}$=1.80 min (analytical method B1)
$[M+H]^+$=341 (analytical method B1)

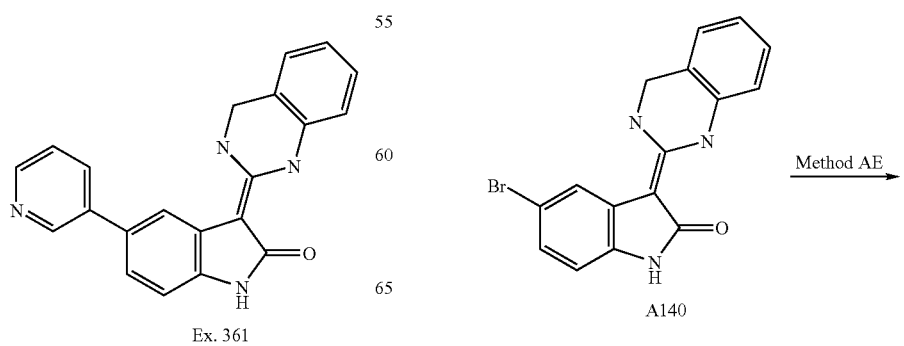

Ex. 361     A140 Method AE →

-continued

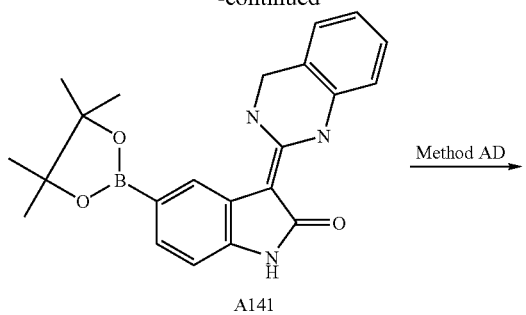

A141

Method AD →

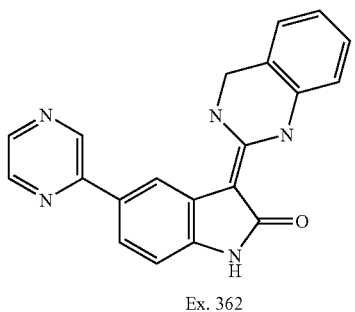

Ex. 362

Method AE

Under an argon atmosphere, A140 (2 g), bis(pinacolate)diboran (1.63 g), potassium acetate (1.72 g) and 1,1'-bis(diphenylphosphino)-ferrocene-palladium(II)dichloride (475 mg) are combined with 15 mL anhydrous dioxane. The reaction mixture is stirred for 3 h at 80° C. and then combined with water and DCM. The organic phase is separated off, dried and filtered through silica gel. It is washed several times with ethyl acetate. The organic phases are combined and the solvent is eliminated in vacuo. This residue (A141) is reacted analogously to Method AD to form Example 362, using 2-chloropyrazine in this case.

$t_{ret}$=1.74 min (analytical method B1)

[M+H]$^+$=342 (analytical method B1)

By using suitable indolinone derivatives (A139) and the corresponding heteroarylboric acids or haloheteroaromatic compounds the following compounds are prepared analogously to Method F, AD and AE.

Examples 363-430

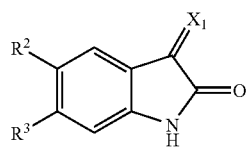

| Ex | R² | R³ | R$_{X1}$ | $t_{ret}$ [min] | [M + H]⁺ | HPLC Method |
|---|---|---|---|---|---|---|
| 363 | 3-pyridyl-X₂ | H | N-methylpiperazinyl-phenyl-(N-CH₃)-NH-X₁ fused ring | 1.65 | 453 | B1 |
| 364 | 3-pyridyl-X₂ | H | morpholinyl-phenyl-(N-CH₃)-NH-X₁ fused ring | 1.69 | 440 | B1 |

-continued
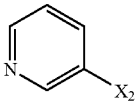
| Ex | R² | R³ | R_{X1} | t_{ret} [min] | [M + H]⁺ | HPLC Method |
|---|---|---|---|---|---|---|
| 365 |  | H | 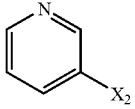 | 1.93 | 369 | B1 |
| 366 | 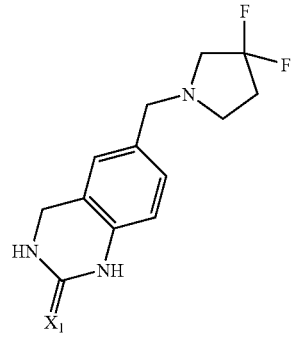 | H | 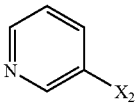 | 1.97 | 460 | B1 |
| 367 | 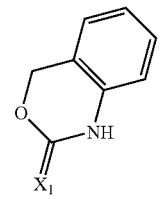 | H | 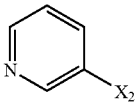 | 1.86 | 342 | B1 |
| 368 | 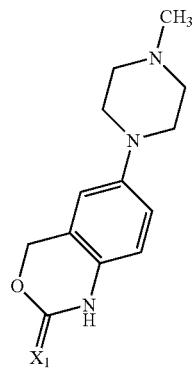 | H | 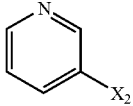 | 1.79 | 440 | B1 |
| 369 | 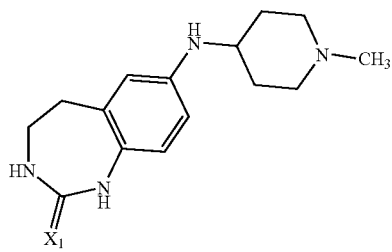 | H | | 1.75 | 234 | B1 |

-continued

| Ex | R² | R³ | R_X1 | t_ret [min] | [M + H]⁺ | HPLC Method |
|---|---|---|---|---|---|---|
| 370 | pyridin-3-yl-X₂ | H | 7-morpholino-4H-benzo[d][1,3]oxazin-2(1H)-one-X₁ | 1.82 | 427 | B1 |
| 371 | pyridin-3-yl-X₂ | H | 7-morpholino-4,5-dihydro-1H-benzo[d][1,3]diazepin-2(3H)-one-X₁ | 1.78 | 440 | B1 |
| 372 | pyridin-3-yl-X₂ | H | thieno[2,3-d]pyrimidin-2(1H)-one-X₁ | 1.75 | 347 | B1 |
| 373 | pyridin-3-yl-X₂ | H | 4H-benzo[d][1,3]thiazin-2(1H)-one-X₁ | 1.99 | 358 | B1 |
| 374 | pyridin-3-yl-X₂ | H | 7-(3-hydroxypyrrolidin-1-yl)-3,4-dihydroquinazolin-2(1H)-one-X₁ | 1.7 | 426 | B1 |

-continued
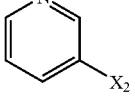
| Ex | R² | R³ | R_{X1} | t_{ret} [min] | [M + H]⁺ | HPLC Method |
|---|---|---|---|---|---|---|
| 375 | 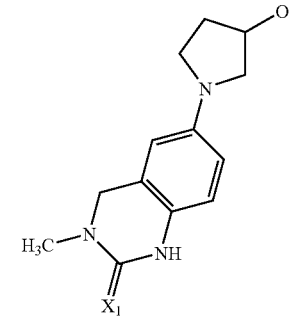 | H | 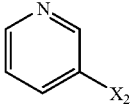 | 1.64 | 440 | B1 |
| 376 | 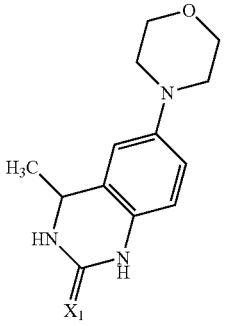 | H | 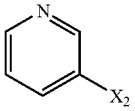 | 1.82 | 440 | B1 |
| 377 | 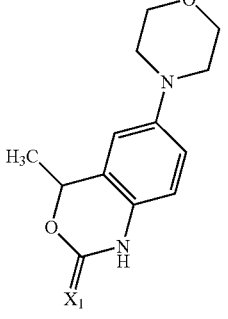 | H | 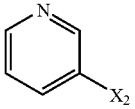 | 1.89 | 441 | B1 |
| 378 | 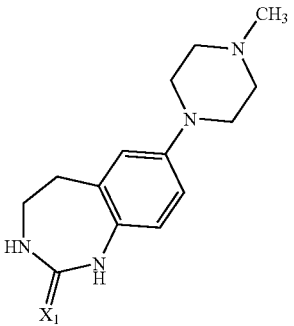 | H | | 1.75 | 453 | B1 |

-continued
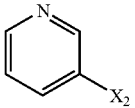
| Ex | R² | R³ | R_X1 | t_ret [min] | [M + H]⁺ | HPLC Method |
|---|---|---|---|---|---|---|
| 379 | 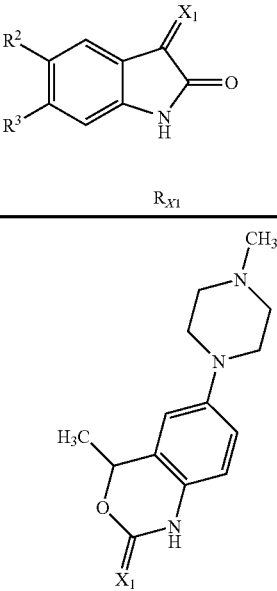 | H | 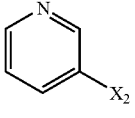 | 1.86 | 454 | B1 |
| 380 | 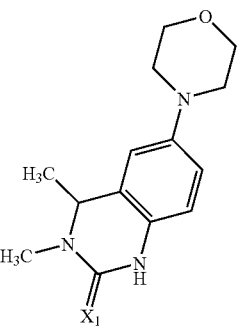 | H | 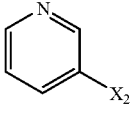 | 1.75 | 454 | B1 |
| 381 | 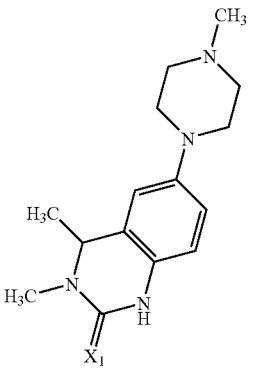 | H | 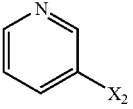 | 1.74 | 467 | B1 |
| 382 | 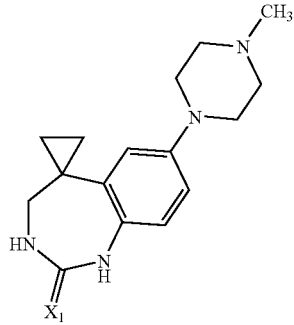 | H |  | 1.78 | 479 | B1 |

-continued

| Ex | R² | R³ | R_X1 | t_ret [min] | [M + H]⁺ | HPLC Method |
|---|---|---|---|---|---|---|
| 383 | 4-ethoxy-pyridin-3-yl (X₂) | H | 1,2,3,4-tetrahydroquinazolin-2-one-4-yl-methyl (X₁) | 1.78 | 371 | B1 |
| 384 | 2-fluoropyridin-3-yl (X₂) | H | 1,2,3,4-tetrahydroquinazolin-2-one-4-yl-methyl (X₁) | 1.91 | 359 | B1 |
| 385 | 2-fluoropyridin-3-yl (X₂) | H | 6-(4-methylpiperazin-1-yl)-1,2,3,4-tetrahydroquinazolin-2-one-4-yl (X₁) | 1.84 | 457 | B1 |
| 386 | 2-fluoropyridin-3-yl (X₂) | H | 6-morpholino-1,2,3,4-tetrahydroquinazolin-2-one-4-yl (X₁) | 1.85 | 444 | B1 |

-continued

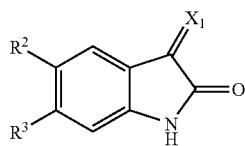

| Ex | R² | R³ | R_X1 | t_ret [min] | [M + H]⁺ | HPLC Method |
|---|---|---|---|---|---|---|
| 387 | 2-fluoropyridin-3-yl (X₂) | H | (4-methylpiperazinyl substituted 3-methyl-tetrahydroquinazolin-2-one) | 1.78 | 471 | B1 |
| 388 | 2-fluoropyridin-3-yl (X₂) | H | (morpholinyl substituted 3-methyl-tetrahydroquinazolin-2-one) | 1.81 | 458 | B1 |
| 389 | 6-amino-pyridin-3-yl (X₂) | H | (tetrahydroquinazolin-2-one) | 1.7 | 356 | B1 |
| 390 | 5-methoxy-pyridin-3-yl (X₂) | H | (tetrahydroquinazolin-2-one) | 1.87 | 371 | B1 |
| 391 | 5-amino-pyridin-3-yl (X₂) | H | (tetrahydroquinazolin-2-one) | 1.62 | 356 | B1 |

-continued
| Ex | R² | R³ | R_X1 | t_ret [min] | [M + H]⁺ | HPLC Method |
|---|---|---|---|---|---|---|
| 392 | 4-methoxy-3-pyridyl (X₂) | F, X₃ | 2-oxo-1,2,3,4-tetrahydroquinazolin-? (X₁) | 1.8 | 389 | B1 |
| 393 | 2-fluoro-3-pyridyl (X₂) | F, X₃ | 2-oxo-1,2,3,4-tetrahydroquinazolin-? (X₁) | 1.96 | 377 | B1 |
| 394 | 2-fluoro-3-pyridyl (X₂) | F, X₃ | 6-(4-methylpiperazin-1-yl)-2-oxo-1,2,3,4-tetrahydroquinazolin-? (X₁) | 1.85 | 475 | B1 |
| 395 | 2-fluoro-3-pyridyl (X₂) | F, X₃ | 6-morpholino-2-oxo-1,2,3,4-tetrahydroquinazolin-? (X₁) | 1.89 | 462 | B1 |
| 396 | 3-pyridyl (X₂) | F, X₃ | 2-oxo-1,2,3,4-tetrahydroquinazolin-? (X₁) | 1.87 | 359 | B1 |

-continued
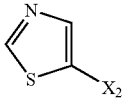
| Ex | R² | R³ | R_X1 | t_ret [min] | [M + H]⁺ | HPLC Method |
|---|---|---|---|---|---|---|
| 397 | 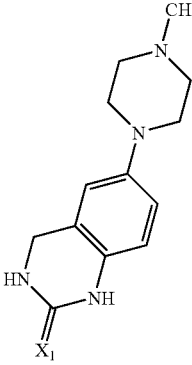 | H | 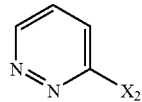 | 1.72 | 445 | B1 |
| 398 | 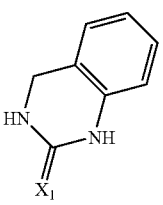 | H | 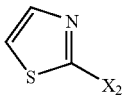 | 1.65 | 342 | B1 |
| 399 | 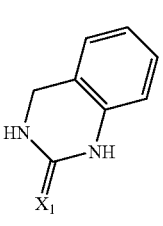 | H | 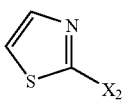 | 1.9 | 347 | B1 |
| 400 | 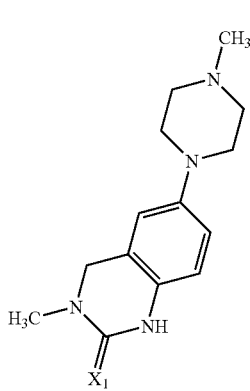 | H | | 1.74 | 459 | B1 |

-continued
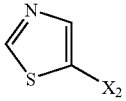
| Ex | R² | R³ | R_X1 | t_ret [min] | [M + H]⁺ | HPLC Method |
|---|---|---|---|---|---|---|
| 401 |  | 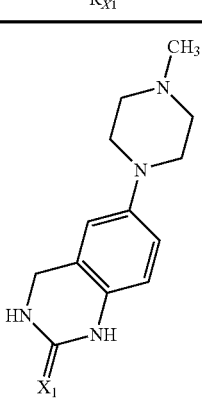 | 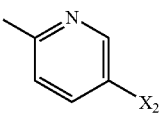 | 1.81 | 463 | B1 |
| 402 | 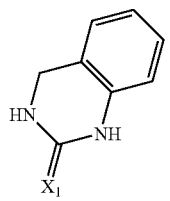 | H | 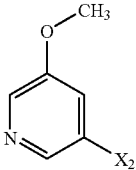 | 2.06 | 375 | B1 |
| 403 |  | 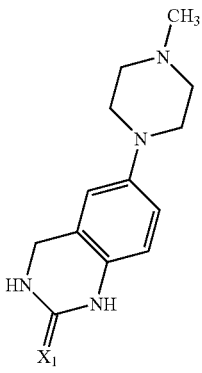 | 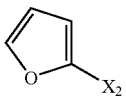 | 1.83 | 487 | B1 |
| 404 | 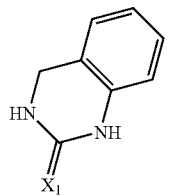 | H | 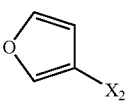 | 2.07 | 330 | B1 |
| 405 | 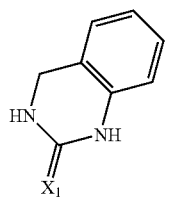 | H | 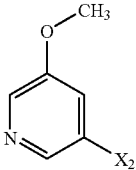 | 2.05 | 330 | B1 |

-continued

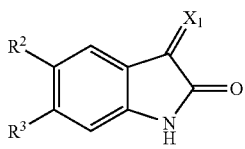

| Ex | R² | R³ | R_{X1} | t_{ret} [min] | [M + H]⁺ | HPLC Method |
|---|---|---|---|---|---|---|
| 406 | pyridin-2-yl-X₂ | H | tetrahydroquinazolin-2(1H)-one-CH₂- | 1.88 | 341 | B1 |
| 407 | pyridazin-4-yl-X₂ | H | tetrahydroquinazolin-2(1H)-one-CH₂- | 1.63 | 342 | B1 |
| 408 | pyrimidin-5-yl-X₂ | H | tetrahydroquinazolin-2(1H)-one-CH₂- | 1.68 | 342 | B1 |
| 409 | 1-methyl-1H-pyrazol-4-yl-X₂ | H | 4-methylpiperazinyl-tetrahydroquinazolin-2(1H)-one | 1.67 | 442 | B1 |
| 410 | 3-methyl-1,2,4-oxadiazol-5-yl-X₂ | H | tetrahydroquinazolin-2(1H)-one-CH₂- | 1.88 | 346 | B1 |
| 411 | thiazol-4-yl-X₂ | H | tetrahydroquinazolin-2(1H)-one-CH₂- | 1.85 | 347 | B1 |

-continued

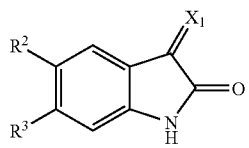

| Ex | R² | R³ | R_X1 | t_ret [min] | [M + H]⁺ | HPLC Method |
|---|---|---|---|---|---|---|
| 412 | 4-methyl-3-pyridyl (X₂) | H | benzyl-dihydroquinazolinone (X₁) | 1.86 | 355 | B1 |
| 413 | 6-methyl-3-pyridyl (X₂) | H | benzyl-dihydroquinazolinone (X₁) | 1.91 | 355 | B1 |
| 414 | 5-methyl-3-pyridyl (X₂) | H | benzyl-dihydroquinazolinone (X₁) | 1.89 | 355 | B1 |
| 415 | 5-hydroxy-3-pyridyl (X₂) | H | benzyl-dihydroquinazolinone (X₁) | 1.28 | 357 | B1 |
| 416 | 6-fluoro-3-pyridyl (X₂) | H | benzyl-dihydroquinazolinone (X₁) | 1.97 | 359 | B1 |
| 417 | 5-fluoro-3-pyridyl (X₂) | H | benzyl-dihydroquinazolinone (X₁) | 1.93 | 359 | B1 |

-continued

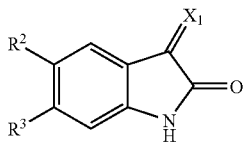

| Ex | R² | R³ | R_X1 | t_ret [min] | [M + H]⁺ | HPLC Method |
|---|---|---|---|---|---|---|
| 418 | 4-cyano-pyridin-3-yl (X₂) | H | 3,4-dihydroquinazolin-2(1H)-ylidene-CH₂-aryl | 1.82 | 366 | B1 |
| 419 | 5-cyano-pyridin-3-yl (X₂) | H | 3,4-dihydroquinazolin-2(1H)-ylidene-CH₂-aryl |  | 366 | B1 |
| 420 | 2-methoxy-pyridin-3-yl (X₂) | H | 3,4-dihydroquinazolin-2(1H)-ylidene-CH₂-aryl | 1.96 | 371 | B1 |
| 421 | 5-chloro-pyridin-3-yl (X₂) | H | 3,4-dihydroquinazolin-2(1H)-ylidene-CH₂-aryl | 2.07 | 375 | B1 |
| 422 | 4-chloro-pyridin-3-yl (X₂) | H | 3,4-dihydroquinazolin-2(1H)-ylidene-CH₂-aryl | 1.91 | 375 | B1 |
| 423 | 2-chloro-pyridin-3-yl (X₂) | H | 3,4-dihydroquinazolin-2(1H)-ylidene-CH₂-aryl | 1.91 | 375 | B1 |

-continued
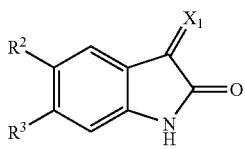
| Ex | R² | R³ | R_X1 | t_ret [min] | [M + H]⁺ | HPLC Method |
|---|---|---|---|---|---|---|
| 424 | imidazo[1,2-a]pyridin-3-yl | H | 6-(4-methylpiperazin-1-yl)-3,4-dihydroquinazolin-2(1H)-yl | 1.76 | 478 | B1 |
| 425 | 1H-pyrrolo[2,3-b]pyridin-5-yl | H | 6-(4-methylpiperazin-1-yl)-3,4-dihydroquinazolin-2(1H)-yl | 1.77 | 478 | B1 |
| 426 | imidazo[1,2-a]pyrimidin-3-yl | H | 6-(4-methylpiperazin-1-yl)-3,4-dihydroquinazolin-2(1H)-yl | 1.56 | 479 | B1 |
| 427 | 5-ethoxypyridin-3-yl | H | 3,4-dihydroquinazolin-2(1H)-yl | 1.97 | 385 | B1 |

-continued

| Ex | R² | R³ | R$_{X1}$ | t$_{ret}$ [min] | [M + H]⁺ | HPLC Method |
|---|---|---|---|---|---|---|
| 428 | 4-ethoxypyridin-3-yl (X₂) | H | 1,2,3,4-tetrahydroquinazolin-2(X₁)-yl-methyl | 1.85 | 385 | B1 |
| 429 | isoquinolin-4-yl (X₂) | H | 1,2,3,4-tetrahydroquinazolin-2(X₁)-yl-methyl | 1.99 | 391 | B1 |
| 430 | quinolin-3-yl (X₂) | H | 1,2,3,4-tetrahydroquinazolin-2(X₁)-yl-methyl | 2.04 | 391 | B1 |

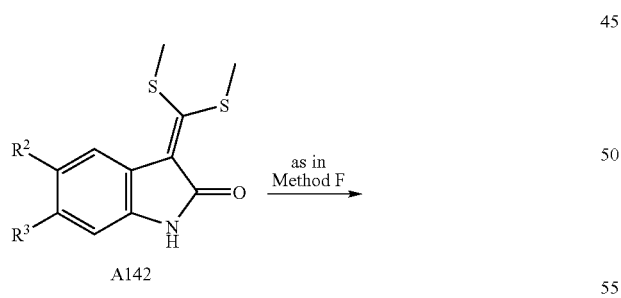

A142 →(as in Method F)

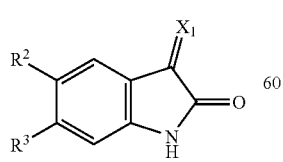

The following target molecules are prepared by using suitable indolinone derivatives (A142) and the corresponding diamines analogously to Method F.

Examples 431-437
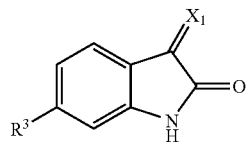
| Ex | R³ | X₁ | t_ret [min] | [M + H]⁺ | HPLC Method |
|---|---|---|---|---|---|
| 431 | CH₃-O-C(O)-X₃ | 4-methylpiperazinyl-phenyl-tetrahydroquinazolin-2-ylidene | 1.73 | 420 | B1 |
| 432 | H₃C-O-X₃ | 4-methylpiperazinyl-phenyl-tetrahydroquinazolin-2-ylidene | 1.67 | 392 | B1 |
| 433 | O⁻-N⁺(=O)-X₃ | 4-methylpiperazinyl-phenyl-tetrahydroquinazolin-2-ylidene | 1.79 | 407 | B1 |

-continued
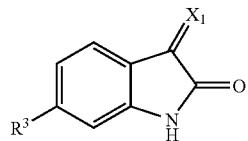
| Ex | R³ | X₁ | t_ret [min] | [M + H]⁺ | HPLC Method |
|---|---|---|---|---|---|
| 434 | | | 1.70 | 387 | B1 |
| 435 | | | 1.97 | 430 | B1 |
| 436 | | | 1.89 | 440/442 | B1 |
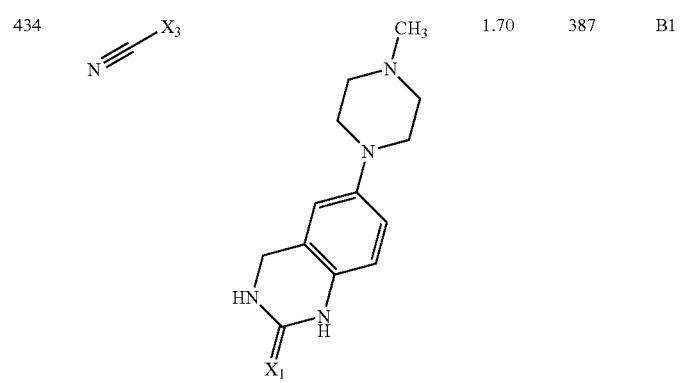
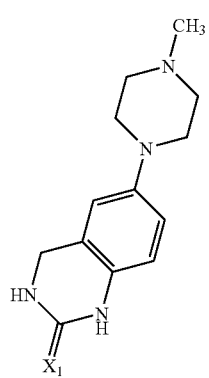
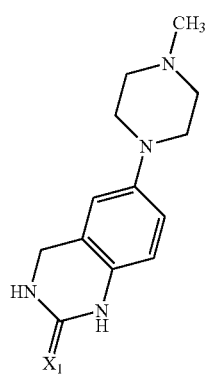

-continued
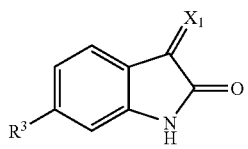
| Ex | R³ | X₁ | t_ret [min] | [M + H]⁺ | HPLC Method |
|---|---|---|---|---|---|
| 437 | Br—X₃ | CH₃ (piperazine-aryl group) | 1.89 | 454/456 | B1 |
The following Examples may be synthesised using Method W.
Examples 438-441
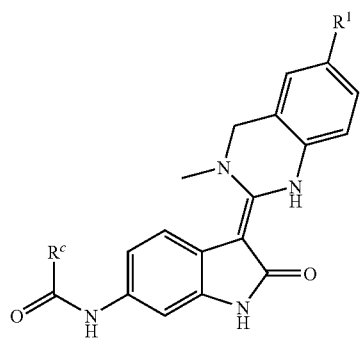
| Ex | R^c | R¹ | t_ret [min] | [M + H]⁺ | UVmax [nm] | HPLC |
|---|---|---|---|---|---|---|
| 438 | 7-methyl-1H-benzimidazol-2-yl | 4-methylpiperazin-1-yl | 1.97 | 549 | 218 | B1 |
| 439 | 7-fluoro-1H-benzimidazol-2-yl | 4-methylpiperazin-1-yl | 1.86 | 553 | 298 | B1 |
| 440 | 5,7-difluoro-1H-benzimidazol-2-yl | 4-methylpiperazin-1-yl | 1.88 | 571 | 296 | B1 |

-continued

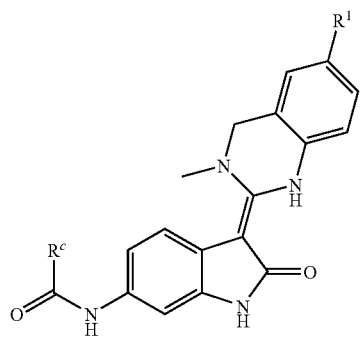

| Ex | R$^c$ | R$^1$ | t$_{ret}$ [min] | [M + H]$^+$ | UVmax [nm] | HPLC |
|---|---|---|---|---|---|---|
| 441 | (3,4-difluorobenzimidazol-2-yl-NH-) | (4-methylpiperazin-1-yl) | 1.88 | 571 | 298 | B1 |

Method AF

Similarly to Method W, 1 equiv. of the amino compound is placed in a suitable solvent (15 mL/mmol, e.g. DCM, DMF), but approx. 1.5 equiv. of an isocyanate corresponding to the desired R$^c$ and 3 equiv. triethylamine are added. After the reaction has ended the volatile constituents are eliminated in vacuo and the product is isolated by preparative HPLC.

Examples 442-448

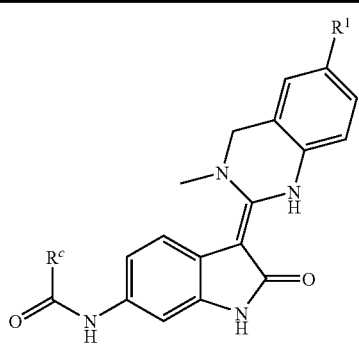

| Ex. | R$^c$ | R$^1$ | t$_{ret}$ [min] | [M + H]$^+$ | UVmax [nm] | HPLC |
|---|---|---|---|---|---|---|
| 442 | PhC(O)NH- | (4-methylpiperazin-1-yl) | 1.94 | 538 | 234; 308 | B1 |
| 443 | (2,6-difluorophenyl)C(O)NH- | (4-methylpiperazin-1-yl) | 1.88 | 574 | 222; 350 | B1 |

-continued

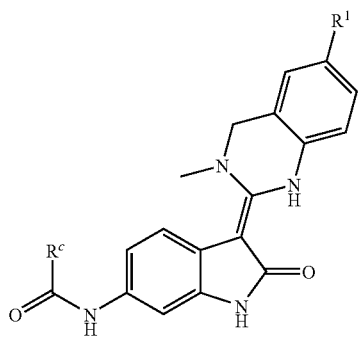

| Ex. | R$^c$ | R$^1$ | t$_{ret}$ [min] | [M + H]$^+$ | UVmax [nm] | HPLC |
|---|---|---|---|---|---|---|
| 444 | isobutyramide | N-methylpiperazine | 1.82 | 504 | 218; 345 | B1 |
| 445 | furan-2-carboxamide | N-methylpiperazine | 1.75 | 528 | | B1 |
| 446 | 5-methylfuran-2-carboxamide | N-methylpiperazine | 1.84 | 542 | | B1 |
| 447 | 3-fluoroanilino | N-methylpiperazine | 1.84 | 528 | 250 | B1 |
| 448 | 3-methoxyanilino | N-methylpiperazine | 1.79 | 540 | 255 | B1 |

Examples 449-459

Synthesis of the Examples wherein R$^{3'}$=R$^{3''}$=Br or R$^{3''}$=NO$_2$; R$^{3'}$=NH$_2$

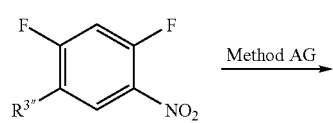 $\xrightarrow{\text{Method AG}}$

-continued

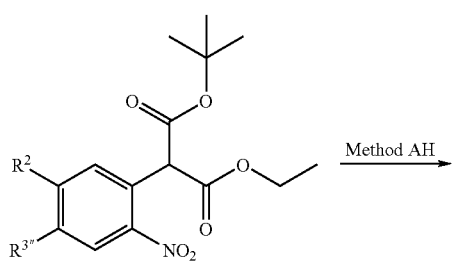 $\xrightarrow{\text{Method AH}}$

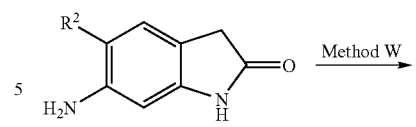

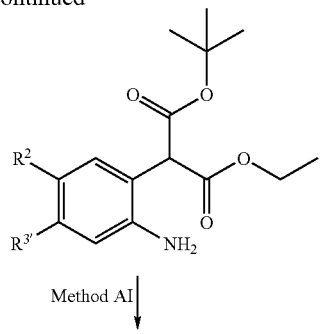

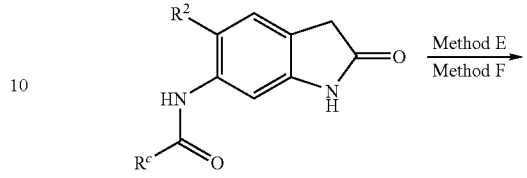

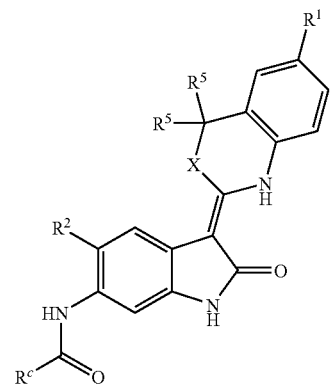

Method AG—General Procedure

A 1,5-difluoro-2-nitrobenzene (1 g) substituted according to the desired R$^{3''}$ is dissolved in approx. 5 mL THF or dioxane. Depending on the desired R$^2$, 1 equiv. of the corresponding sulphinate salt or of the corresponding amine or alcohol with DIPEA (1.1 equiv.) are added and the mixture is stirred at 50-70° C. After the first substitution has ended 1 equiv. tert.-butylethylmalonate, 3 equiv. sodium hydride and optionally NMP (2 mL) and 1 equiv. Potassium carbonate are added and the mixture is again stirred at 50-60° C. After the reaction has ended the reaction mixture is neutralised with 1 N HCl, the volatile constituents are eliminated in vacuo and the product is isolated by preparative HPLC. The sequence of the first and second substitution may optionally be reversed.

Method AH—General Procedure

The compound obtained from Method AE (1 g) is dissolved in THF (100 mL), Raney nickel (100 mg) is added and the mixture is hydrogenated under an H$_2$ atmosphere (3-5 bar). Once the reaction has ended the reaction mixture is filtered and the filtrate is freed in vacuo from the volatile constituents. The crude product thus obtained is further used directly.

Method AI—General Procedure

The compound obtained from Method AH (1 g) is mixed with 8-15 mL of a suitable solvent (e.g. THF, toluene, dioxane). After the addition of 2-5 mL TFA it is heated to 80-100° C. After the reaction has ended the reaction mixture is combined with DCM (50 mL) and made basic with aqueous NaHCO$_3$ solution. The organic phase is separated off and the aqueous phase is repeatedly extracted with DCM. The combined organic phases are dried, filtered and freed from the volatile constituents in vacuo. The crude product obtained is purified chromatographically by preparative HPLC.

Examples 451-455 may be synthesised according to Method W, E and F from the substances wherein R$^{3'}$=NH$_2$ obtained using Method AI:

Examples 449-450 may be synthesised according to Method E and F from the substances wherein R$^{3'}$=Br obtained using Method AG. From these, the Examples 456-459 may be prepared using Method AJ or AK:

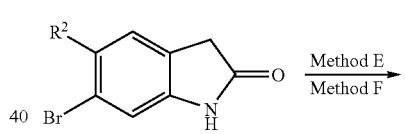

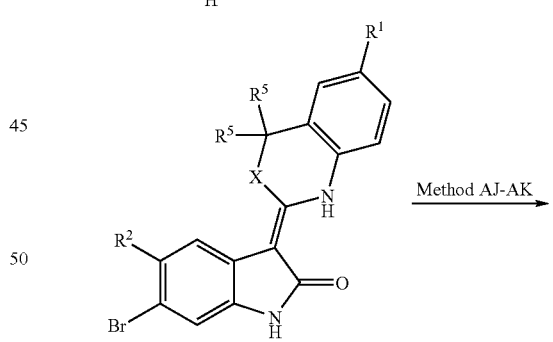

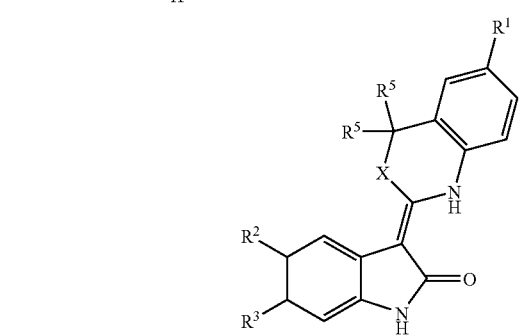

Method AJ (Sonogashira Reaction)

Unter an argon atmosphere the substance with $R^{3'}$=Br obtained from Method F (20 mg) is combined with 2 equiv. of the alkyne substituted according to $R^3$, 0.4 equiv. CuI, 0.1 equiv. Bis(triphenylphosphineo)palladium dichloride and 5 equiv. triethylamine with 150 μL DMF and the mixture is stirred for 5 min at RT and then at 100° C. During this time a further 8 equiv. of the alkyne are added batchwise and the mixture is stirred until the desired product has formed. Then the cooled reaction mixture is freed from the volatile constituents in vacuo and the product is isolated chromatographically by preparative HPLC.

Method AK (Suzuki Coupling)

Unter an argon atmosphere the substance with $R^{3'}$=Br obtained from Method F (50 mg) is combined with 3.2 equiv. KOAc, 2.2 equiv. Bis(pinacolato)diboron or bis(neopentylglycolato)diboron and 0.1 equiv. 1,1'-bis(diphenylphosphino)ferrocene palladium dichloride and 1.5 ml of 1,4-dioxane. The reaction mixture is heated to 85° C. for 1-2 h, cooled to RT again and further used directly. For this, 0.5 mL methanol, 4 equiv. $K_2CO_3$, 0.1-0.2 equiv. 1,1'-bis(diphenylphosphino)ferrocene palladium dichloride and 2 equiv. of a corresponding aryl or heteroaryl halide are added, depending on the desired $R^3$. The reaction mixture is heated to 85° C. again until the desired product has formed. Then the cooled reaction mixture is freed in vacuo from the volatile constituents and the product is isolated chromatographically by preparative HPLC.

Examples 449-459

| Ex | $R^2$ | $R^3$ | $R^1$ | $t_{ret}$ [min] | $[M + H]^+$ | UVmax [nm] | HPLC |
|---|---|---|---|---|---|---|---|
| 449 | phenylsulfonyl | Br | H | 1.97 | | 262; 354 | B1 |
| 450 | H | Br | piperazinyl | 1.89 | | 354 | B1 |
| 451 | phenylsulfonyl | benzimidazole-2-carboxamide | piperazinyl | 2.05 | 675 | 380 | B1 |
| 452 | 3,3-difluoropyrrolidinyl | benzimidazole-2-carboxamide | piperazinyl | 2.15 | 640 | 295 | B1 |

-continued
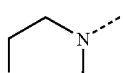
| Ex | R² | R³ | R¹ | t_ret [min] | [M + H]⁺ | UVmax [nm] | HPLC |
|---|---|---|---|---|---|---|---|
| 453 | 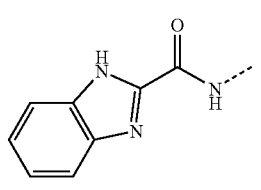 | 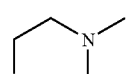 | 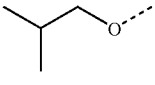 | 1.97 | 620 | | B1 |
| 454 | 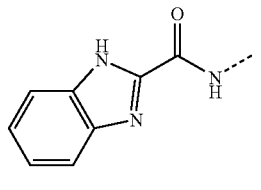 | 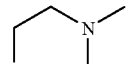 | 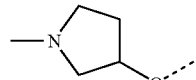 | 2.24 | 607 | 298 | B1 |
| 455 | 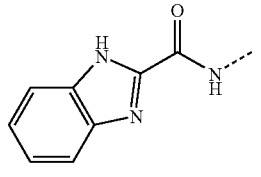 | 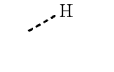 | ---H | 2.01 | 536 | 290 | B1 |
| 456 | ---H |  | 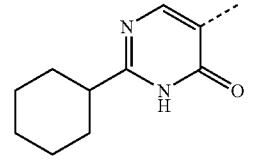 | 1.83 | 552 | 222; 366 | B1 |
| 457 | ---H | 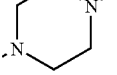 |  | 2.40 | 564 | 366 | B1 |
| 458 | ---H | 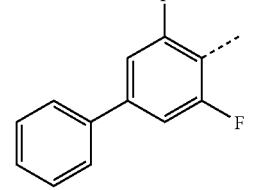 | 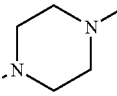 | 2.24 | 584/586 | 366 | B1 |

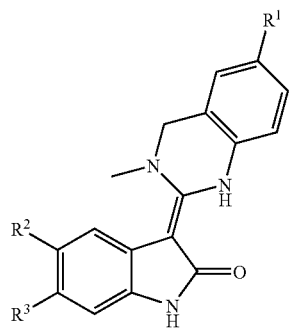

| Ex | R² | R³ | R¹ | t_ret [min] | [M+H]⁺ | UVmax [nm] | HPLC |
|---|---|---|---|---|---|---|---|
| 459 | PhS(O)₂- | CH₂-C≡C-CH₂-N(CO₂tBu)-CH₂CF₃ | H | 2.11 | 653 | 374 | E* |

*HPLC Method E corresponds to HPLC Method D, except that: column=Agilent Zorbax SBC8, 2.1×50 mm, 3.5μ; solvent: A=water with 0.2% formic acid added, B=acetonitrile with 0.2% formic acid added; gradient: 5% B, within 1.5 min to 95% B, then 0.5 min isocratically at 100% B and 1 min isocratically at 5% B, flow 1.2 mL/min.

Abbreviations Used

| | |
|---|---|
| equiv. | equivalent(s) |
| DCM | dichloromethane |
| DIPEA | N,N-diisopropylethylamine |
| DMF | N,N-dimethylformamide |
| DMSO | dimethylsulphoxide |
| Et | ethyl |
| EtOAc | ethyl acetate |
| h | hour |
| HCl | hydrochloric acid |
| HPLC | high performance liquid chromatography |
| conc. | concentrated |
| HMDS | hexamethyldisilazane |
| iPr | isopropyl |
| Me | methyl |
| MeOH | methanol |
| min | minute |
| mL | millilitre |
| MS | mass spectrometry |
| N | Normal |
| NMP | 1-methyl-2-pyrrolidone |
| NMR | Nuclear Magnetic Resonance spectroscopy |
| ppm | part per million |
| RP | reversed phase |
| RT | room temperature |
| TFA | trifluoroacetic acid |
| TBTU | O-benztriazol-1-yl-N,N,N',N'-tetramethyluronium tetrafluoroborate |
| tert | tertiary |
| THF | tetrahydrofuran |

HPLC-Methods

Method A

HPLC: Agilent 1100 Series

MS: Agilent LC/MSD SL (LCMS1: 1100 series LC/MSD)

Column: Waters, Xterra MS C18, 2.5 μm, 2.1×30 mm, Part. No. 186000592

Solvent: A: H₂O (Millipore purified purest water) with 0.1% HCOOH

B: acetonitrile (HPLC grade)

Detection: MS: Positive and negative

Mass range: 120-900 m/z

Fragmentor: 120

Gain EMV: 1

Threshold: 150

Stepsize: 0.25

UV: 254 nm

Bandwide: 1 (LCMS1: 2)

Reference: off

Spectrum: Range: 250-400 nm

Range step: 1.00 nm

Threshold: 4.00 mAU

Peakwidth: <0.01 min (LCMS1: >0.05 min)

Slit: 1 nm (LCMS1: 2 nm)

Injection: Inj. Vol.: 5 μL

Inj. Mode: Needle wash

Separation: Flow: 1.10 mL/min

Column temp.: 40° C.

Gradient: 0 min 5% solvent B 0-2.5 min 5%->95% solvent B 2.50-2.80 min 95% solvent B 2.81-3.10 min 95%->5% solvent B

Method B

HPLC: Agilent 1100 Series
MS: 1100 Series LC/MSD (API-ES +/−3000V, Quadrupol, G1946D)
MSD Signal Settings: Scan pos 120-900, Scan neg 120-900
Column: phenomenex; Part No. 00M-4439-BO-CE; Gemini 3µ C18 110 Å; 20·2.0 mm
Eluant: A: 5 mM $NH_4HCO_3$/20 mM $NH_3$ (pH=9.5)
B: acetonitrile HPLC grade
Detection: Signal: UV 254 nm (bandwide 1, reference off)
Spectrum: range: 250-400 nm; step: 1 nm
Peak width <0.01 min (0.1 s)
Injection: 10 µL standard injection

Method: B1

Flow: 1.0 mL/min
Column temperature: 40° C.

| Pump gradient: | 0.0-2.5 min | 5% -> 95% solvent B |
|---|---|---|
| | 2.5-2.8 min | 95% solvent B |
| | 2.8-3.1 min | 95% -> 5% solvent B |

Method C

HPLC: Agilent 1100 Series
MS: 1100 Series LC/MSD (Quadrupol, G1946D; API-ES)
MSD Signal Settings: Capillary Voltage +/−3000V
Scan pos 100-1200, Scan neg 100-1200
Column: Waters X Bridge; C18; 3.5 µm; 2.1·50 mm
Eluant: A: 5 mM $NH_4HCO_3$/20 mM $NH_3$ (pH=9.5)
B: acetonitrile (HPLC grade)
Detection:
Signal: UV 254 nm (Bandwide 8, Reference off)
UV 230 nm (Bandwide 8, Reference off)
Spectrum: range: 190-450 nm; step: 4 nm; Threshold 1 mAU
Peakbreite: >0.03 min
Injection: 2 µL standard injection
Flow: 1.2 mL/min
Column oven.: 35° C.

| Gradient: | 0.01 min | 5% B |
|---|---|---|
| | 1.25 min | 95% B |
| | 2.00 min | 95% B |
| | 2.01 min | 5% B |
| | Stop time: 3.00 min | |

Method D

HPLC: Agilent 1100 Series
MS: LC/MSD SL (Quadrupol, G1956B; MM−ES+APCI)
MSD Signal Settings: Capillary Voltage +/−2000V
Corona Current [µA] +/−8
Charging Voltage +/−2000
Scan pos 105-1200, Scan neg 105-1200
column: Waters X Bridge; C18; 3.5 µm; 2.1·50 mm
eluant: A: 5 mM $NH_4HCO_3$/20 mM $NH_3$ (pH=9.5)
B: acetonitrile HPLC grade
Detection:
Signal: UV 254 nm (Bandwide 4, Reference off)
UV 230 nm (Bandwide 4, Reference off)
Spectrum: range: 190-450 nm; step: 4 nm; Threshold 1 mAU
Peak width: >0.03 min
Injection: 2 µL standard injection
Flow: 1.2 mL/min
Column oven.: 35° C.

| Gradient: | 0.01 min | 5% B |
|---|---|---|
| | 1.25 min | 95% B |
| | 2.00 min | 95% B |
| | 2.01 min | 5% B |
| | Stop time: 3.00 min | |

The following Examples describe the biological activity of the compounds according to the invention without restricting the invention to these Examples.

As demonstrated by DNA staining followed by FACS or Cellomics Array Scan analysis, the inhibition of proliferation brought about by the majority of the compounds according to the invention is mediated above all by errors in chromosome segregation and/or cytokinesis. For this reason, massive polyploidia occurs in these cases, which may finally lead to inhibition of proliferation or even apoptosis. Moreover, many of the compounds according to the invention cause an inhibition of proliferation, by interfering with intracellular signal transduction pathways which are important to the survival of cells-primarily, but not exclusively, in cells which have become dependent on such signal pathways during their development Inhibiting these pathways in corresponding cells induces arrest in the G1 phase of the cell cycle and/or apoptosis.

On the basis of their biological properties the compounds of general formula (I) according to the invention, their isomers and the physiologically acceptable salts thereof are suitable for treating diseases characterised by excessive or abnormal cell proliferation or by the activation of survival-mediating signal pathways.

Example Aurora-B Kinase Assay

A radioactive enzyme inhibition assay was developed using *E. coli*-expressed recombinant *Xenopus laevis* Aurora B wild-type protein equipped at the N-terminal position with a GST tag (amino acids 60-361) in a complex with *Xenopus laevis* INCENP (amino acids 790-847), which is obtained from bacteria and purified. In equivalent manner a *Xenopus laevis* Aurora B mutant (G96V) in a complex with *Xenopus laevis* INCENP$^{790-847}$ may also be used.

Expression and Purification

The coding sequence for Aurora-B$^{60-361}$ from *Xenopus laevis* is cloned into a modified version of pGEX-6T (Amersham Biotech) via BamHI and SalI cutting sites. The vector contains two cloning cassettes which are separated by a ribosomal binding site, allowing bi-cistronic expression. In this configuration *Xenopus laevis* Aurora B is expressed by the first cassette, and the *Xenopus laevis* INCENP$^{790-847}$ is expressed by the second cassette. The resulting vector is pAUB-IN$^{847}$.

First of all the *E. coli* strain BL21 (DE3) is co-transformed with pUBS520 helper plasmid and pAUB-IN$^{847}$, after which protein expression is induced using 0.3 mM IPTG at an $OD_{600}$ of 0.45-0.7. The expression is then continued for approx. 12-16 h at 23-25° C. with agitation.

The bacteria are then removed by centrifuging and the pellet is lysed in lysis buffer (50 mM Tris/Cl pH 7.6, 300 mM NaCl, 1 mM DTT, 1 mM EDTA, 5% glycerol, Roche Complete Protease Inhibitor tablets) using ultrasound, using 20-30 mL lysis buffer per liter of E. coli culture. The lysed material is freed from debris by centrifugation (12000 rpm, 45-60 min, JA20 rotor). The supernatant is incubated with 300 µL of equilibrated GST Sepharose Fast Flow (Amersham Biosciences) per liter of E. coli culture for 4-5 h at 4° C. Then the column material is washed with 30 volumes of lysis buffer and then equilibrated with 30 volumes of cleavage buffer (50 mM Tris/Cl pH 7.6, 150 mM NaCl, 1 mM DTT, 1 mM EDTA). To cleave the GST tag from Aurora B, 10 units of Precision Protease (Amersham Biosciences) are used per milligram of substrate and the mixture is incubated for 16 h at 4° C. The supernatant which contains the cleavage product is loaded onto a 6 mL Resource Q column (Amersham Biosciences) equilibrated with ion exchange buffer (50 mM Tris/Cl pH 7.6, 150 mM NaCl, 1 mM DTT, 1 mM EDTA). The Aurora B/INCENP complex is caught as it flows through, then concentrated and loaded onto a Superdex 200 size exclusion chromatography (SEC) column equilibrated with SEC buffer (10 mM Tris/Cl pH 7.6, 150 mM NaCl, 1 mM DTT, 1 mM EDTA). Fractions which contain the AuroraB/INCENP complex are collected and concentrated using Vivaspin concentrators (molecular weight exclusion 3000-5000 Da) to a final concentration of 12 mg/mL. Aliquots (e.g. 240 ng/µL) for kinase assays are transferred from this stock solution into freezing buffer (50 mM Tris/Cl pH 8.0, 150 mM NaCl, 0.1 mM EDTA, 0.03% Brij-35, 10% glycerol, 1 mM DTT) and stored at −80° C.

Aurora B Kinase Assay

Test substances are placed in a polypropylene dish (96 wells, Greiner #655 201), in order to cover a concentration frame of 10 µM-0.0001 µM. The final concentration of DMSO in the assay is 5%. 30 µL of protein mix (50 mM tris/Cl pH 7.5, 25 mM $MgCl_2$, 25 mM NaCl, 167 µM ATP, 10 ng Xenopus laevis Aurora B/INCENP complex in freezing buffer) are pipetted into the 10 µL of test substance provided in 25% DMSO and this is incubated for 15 min at RT. Then 10 µL of peptide mix (100 mM tris/Cl pH 7.5, 50 mM $MgCl_2$, 50 mM NaCl, 5 µM NaCl, 5 µM DTT, 1 µCi gamma-P33-ATP [Amersham], 50 µM substrate peptide [biotin-EPLER-RLSLVPDS or multimers thereof, or biotin-EPLERRL SLVPKM or multimers thereof, or biotin-LRRWSLGLR-RWSLGLRRWSLGLRRWSLG]) are added. The reaction is incubated for 75 min (ambient temperature) and stopped by the addition of 180 µL of 6.4% trichloroacetic acid and incubated for 20 min on ice. A multiscreen filtration plate (Millipore, MAIP NOB10) is equilibrated first of all with 100 µL 70% ethanol and then with 180 µL trichloroacetic acid and the liquids are eliminated using a suitable suction apparatus. Then the stopped kinase reaction is applied. After 5 washing steps with 180 µL 1% trichloroacetic acid in each case the lower half of the dish is dried (10-20 min at 55° C.) and 25 µL scintillation cocktail (Microscint, Packard #6013611) is added. Incorporated gamma-phosphate is quantified using a Wallac 1450 Microbeta Liquid Scintillation Counter. Samples without test substance or without substrate peptide are used as controls. $IC_{50}$ values are obtained using Graph Pad Prism software.

The effect of the compounds according to the invention on kinases that inhibit signal transduction pathways, e.g. on Serine-Threonine Kinase PDK1, is determined in in vitro kinase assays with recombinantly produced protein. In this assay, the compounds exhibit good to very good efficacy, i.e. an $IC_{50}$ value of for example less than 1 µmmol/L, generally less than 0.1 µmol/L.

Example of PDK1 Kinase Assay

Recombinant human PDK1 enzyme (aa 52-556) linked at its N-terminal end to $His_6$ is isolated from baculovirus-infected insect cells. Purified enzyme may be obtained for example from the University of Dundee, Scotland. The following components are combined in a well of a 96-well round-based dish (Messrs. Greiner bio-one, No. 650101):

- 7.5 µL of compound to be tested in varying concentrations (e.g. Starting at 10 µM, and diluted 1:5) in 3.33% DMSO (final concentration 1% DMSO)/assay buffer (50 mM Tris pH 7.5, 0.05% β-mercaptoethanol, 10 mM Mg-acetate)
- 7.5 µL PDK1 (10 ng/well) and PDKtide (KTFCGTPEY-LAPEVRREPRILSEEEQEMF RDFDYIADWC, synthesised by Pepceuticals Limited, Nottingham, United Kingdom; 25 µM final concentration) PDK1 and PDKtide are together diluted accordingly in assay buffer; PDKtide is present in this mixture as an 83.3 µM solution.
- 10 µL ATP solution (25 µM ATP with 0.5 µCi/well gamma-P33-ATP)

The reaction is started by adding the ATP solution and the mixture is incubated for 30 min at ambient temperature; at the start of the reaction the dishes are shaken gently. The reaction is stopped by the addition of 5 µL/well 0.5 M phosphoric acid ($H_3PO_4$) and incubated for about 20 min at ambient temperature. The precipitate is transferred by harvesting onto filter plates (96-well microtitre filter plate: UniFilter GF/C; Messrs Perkin Elmer; No. 6005174), then washed 6 times with 50 mM $H_3PO_4$ and dried at 60° C. Then the plate is stuck down with sealing tape, 25 µL/well of scintillation solution (Microscint 0; Messrs. Perkin Elmer; No. 6013611) are added and the amount of P33 precipitated is measured using the Wallac Betacounter. The measured data are evaluated using Graphpad Prism software.

The antiproliferative activity of the compounds according to the invention is determined on cultivated human tumour cells, for example on NCI-H460 or PC-3 cells. The compounds exhibit good to very good activity, i.e. For example an $EC_{50}$ value in the PC-3 proliferation test of less than 5 µmol/L, generally less than 1 µmol/L.

Measurement of the Inhibition of Proliferation on Cultivated Human Tumour Cells To measure proliferation on cultivated human tumour cells, cells of lung tumour cell line NCI-H460 (obtained from American Type Culture Collection (ATCC)) are cultivated in RPMI 1640 medium (Gibco) and 10% foetal calf serum (Gibco) and harvested in the log growth phase. Then the NCI-H460 cells are placed in 96-well flat-bottomed plates (Falcon) at a density of 1000 cells per well in RPMI 1640 medium and incubated overnight in an incubator (at 37° C. and 5% $CO_2$). The active substances are added to the cells in various concentrations (dissolved in DMSO; DMSO final concentration: 0.1%). After 72 h incubation 20 µL Alamar-Blue reagent (AccuMed International) is added to each well, and the cells are incubated for a further 5-7 h. After incubation the colour change of the AlamarBlue reagent is determined in a Wallac Microbeta fluorescence spectrophotometer. $EC_{50}$ values are calculated using Standard Levenburg Marquard algorithms (GraphPadPrizm).

To measure proliferation on the prostate carcinoma tumour cell line PC-3 (obtained from American Type Culture Collection (ATCC)) the cells are cultivated in Ham's F12K (Gibco) and 10% foetal calf serum (Gibco) and harvested in the log growth phase. Then the PC-3 cells are placed in 96-well plates (Costar) at a density of 2000 cells per well and incubated overnight in an incubator (at 37° C. and 5% $CO_2$), while on each plate 16 wells are used as controls (8 wells with cells to which only DMSO solution has been added (should yield 30-50% maximum value of reduced AlamarBlue), 4 wells containing only medium (medium control, after the addition of oxidised AlamarBlue reagent the back-ground signal is obtained) and 4 wells where again only medium is added (after the addition of reduced AlamarBlue reagent it acts as a maximum value)). The active substances are added to the cells in various concentrations (dissolved in DMSO; DMSO final concentration: 0.2%) (in each case as a double or triple measurement). After 5 days incubation 20 µl AlamarBlue reagent (Serotec) are added to each well, and the cells are incubated for a further 5-7 h. As a control, 20 µL reduced AlamarBlue reagent is added to each of 4 wells (AlamarBlue reagent which is autoclaved for 30 min). After incubation the colour change of the AlamarBlue reagent in the individual wells is determined in a SpectraMax Photometer (Molecular Devices) (extinction 530 nm, emission 590 nm, 5 sec measuring time). The amount of AlamarBlue reagent reacted represents the metabolic activity of the cells. The relative cell activity is calculated in relation to the control (PC-3 cells without inhibitor) and the active substance concentration which inhibits the cell activity by 50% ($EC_{50}$) is derived. The values are calculated from the average of two or three individual measurements.

Cell cycle analyses are carried out for example using FACS analyses (Fluorescence Activated Cell Sorter) or by Cellomics Array Scan (CellCycle Analysis).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1.75 \times 10^6$ NCI-H460 cells are seeded onto a 75 $cm^2$ cell culture flask, and after 24 h either 0.1% DMSO is added as control or the substance is added in various concentrations (in 0.1% DMSO). The cells are incubated for 42 h with the substance or with DMSO. Then the cells are detached with trypsin and centrifuged. The cell pellet is washed with buffered saline solution (PBS) and the cells are then fixed with 80% ethanol at $-20°$ C. for at least 2 h. After another washing step with PBS the cells are permeabilised with Triton X-100 (Sigma; 0.25% in PBS) on ice for 5 min, and then incubated with a solution of PI (Sigma; 10 µg/ml) and RNAse (Serva; 1 mg/mL) in the ratio 9:1 for at least 20 min in the dark.

The DNA measurement is carried out in a Becton Dickinson FACS Analyzer, with an argon laser (500 mW, emission 488 nm); data are obtained and evaluated using the DNA Cell Quest Programme (BD).

Cellomics Array Scan

NCI-H460 cells are seeded into 96-well flat-bottomed dishes (Falcon) in RPMI 1640 medium (Gibco) with 10% foetal calf serum (Gibco) in a density of 2000 cells per well and incubated overnight in an incubator (at 37° C. and 5% $CO_2$). Analogously thereto, PC-3 cells are cultivated in Ham's F12K (Gibco) and 10% foetal calves' serum (Gibco) and harvested in the log growth phase. Then the PC-3 cells are placed in 96-well dishes (FALCON black/clear bottom (#353948)) at a density of 3000 cells per well and incubated overnight in an incubator (at 37° C. and 5% $CO_2$). The active substances are added to the cells in various concentrations (dissolved in DMSO; DMSO final concentration: 0.1%). After 42 h incubation the medium is suction filtered, the cells are fixed for 10 min with 4% formaldehyde solution and Triton X-100 (1:200 in PBS) at ambient temperature and simultaneously permeabilised, and then washed twice with a 0.3% BSA solution (Calbiochem). Then the DNA is stained by the addition of 50 µL/well of 4',6-diamidino-2-phenylindole (DAPI; Molecular Probes) in a final concentration of 300 nM for 1 h at ambient temperature, in the dark. Alternatively, 50 µL/well of Hoechst 33342 (Invitrogen) in PBS may be used for the DNA staining (1 h at RT, final concentration: 5 µg/mL). The preparations are then carefully washed twice with PBS, the dishes are stuck down with black adhesive film and analysed in the Cellomics ArrayScan using the CellCycle BioApplication programme and visualised and evaluated using Spotfire.

The substances of the present invention are Aurora B and/or PDK1 kinase inhibitors. On the basis of their biological properties the compounds of general formula (I) according to the invention, their isomers and the physiologically acceptable salts thereof are suitable for treating diseases characterised by excessive or abnormal cell proliferation or by aberrant activation of the phosphatidylinositol-3-kinase (PI3K)-PDK1-AKT signal pathway.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidermoid carcinoma and plate epithelial carcinoma of the skin; thymomas, cancer of the urethra and cancer of the vulva.

Apart from pathologically/morphologically manifested types of tumour, these compounds according to the invention may also be used to treat "biomarker-defined" cell anomalies or those characterised by other molecular-biological and/or genetic methods, primarily, but not exclusively, those which are characterised by changes stable over time (stable over at least 3 cell divisions), in the amount or state of activation of genes or their gene products such as the phosphatidylinositol-3-kinase family, PDK1, AKT/PK family, RAS family, tyrosine-kinase receptors, cytokine receptors, chemokine receptors.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortinsone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. Antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); anti-mitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. In amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. With the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I), (1)

wherein

Q denotes phenyl, optionally substituted by one or more identical or different $R^1$, and W denotes —$CR^6R^6$, and X denotes —$NR^4$—; and Z denotes —$NR^7$— and Y denotes a bond; and $R^1$, $R^2$, $R^3$, $R^4$, $R^6$ and $R^7$ each independently of one another denote a group selected from among $R^a$, $R^b$ and $R^a$ substituted by one or more identical or different $R^b$ and/or $R^c$; and each $R^a$ independently of one another denotes hydrogen or is selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, N[$S(O)_2R^c]_2$, —$N(R^g)S(O)_2OR^c$, —$N(R^g)S(O)_2NR^cR^c$, —$N(R^g)[S(O)_2]_2R^c$, $N(R^g)C(O)OR^c$, —$N(R^g)C(O)SR^c$, —$N(R^g)C(O)NR^cR^c$, —$N(R^g)C(O)NR^gNR^cR^c$, $N(R^g)N(R^g)C(O)NR^cR^c$, —$N(R^g)C(S)NR^cR^c$, —[$N(R^g)C(O)]_2R^c$, —$N(R^g)[C(O)]_2R^c$, $N\{[C(O)]_2R^c\}_2$, —$N(R^g)[C(O)]_2OR^c$, —$N(R^g)[C(O)]_2NR^cR^c$, —$\{[C(O)]_2OR^c\}_2$, —$N\{[C(O)]_2NR^cR^c\}_2$, —[$N(R^g)C(O)]_2OR^c$, —$N(R^g)C(NR^g)OR^c$, —$N(R^g)C(NOH)R^c$, $N(R^g)C(NR^g)SR^c$ and —$N(R^g)C(NR^g)NR^cR^c$, each $R^c$ independently of one another denotes hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —[$N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —[$N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group optionally substituted by one or more identical or different $R^f$ and/or $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^f$ is a suitable group and each is independently selected from among halogen and —$CF_3$; and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, a tautomer thereof, a racemate thereof, an enantiomer thereof, a diastereomer thereof, or a mixture of any of the foregoing, or a pharmacologically acceptable acid addition salt thereof.

2. The compound according to claim 1, wherein $R^7$ denotes hydrogen or $C_{1-6}$alkyl.

3. The compound according to claim 1, wherein $R^4$ denotes hydrogen.

4. A pharmaceutical preparation, comprising as active substance one or more compounds of formula (1) according to claim 1 with one or more conventional excipients or carriers.

* * * * *